US010533162B2

(12) United States Patent
Ishino et al.

(10) Patent No.: US 10,533,162 B2
(45) Date of Patent: Jan. 14, 2020

(54) DNA POLYMERASE

(71) Applicant: KYUSHU UNIVERSITY, NATIONAL UNIVERSITY CORPORATION, Fukuoka-shi, Fukuoka (JP)

(72) Inventors: Yoshizumi Ishino, Fukuoka (JP); Takeshi Yamagami, Fukuoka (JP); Hiroaki Matsukawa, Fukuoka (JP)

(73) Assignee: KYUSHI UNIVERSITY, NATIONAL UNIVERSITY CORPORATION, Fukuoka--Shi, Fukuoka (JP)

( * ) Notice: Subject to any disclaimer, the term of this patent is extended or adjusted under 35 U.S.C. 154(b) by 0 days.

(21) Appl. No.: 15/855,882

(22) Filed: Dec. 27, 2017

(65) Prior Publication Data

US 2019/0032031 A1 Jan. 31, 2019

Related U.S. Application Data

(63) Continuation of application No. 14/130,636, filed as application No. PCT/JP2012/067872 on Jul. 12, 2012, now abandoned.

(30) Foreign Application Priority Data

Jul. 12, 2011 (JP) ................. 2011-153410

(51) Int. Cl.
| | |
|---|---|
| *C12N 9/12* | (2006.01) |
| *C12N 1/00* | (2006.01) |
| *C12N 1/20* | (2006.01) |
| *C12N 15/63* | (2006.01) |
| *C12P 19/34* | (2006.01) |

(52) U.S. Cl.
CPC ............ *C12N 9/1252* (2013.01); *C12N 1/00* (2013.01); *C12N 1/20* (2013.01); *C12N 15/63* (2013.01); *C12P 19/34* (2013.01); *C12Y 207/07007* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 9,045,797 B2* | 6/2015 | Hosomi | C12Q 1/686 |
| 2003/0027296 A1 | 2/2003 | Chatterjee | |
| 2005/0250131 A1 | 11/2005 | Jestin et al. | |
| 2013/0017542 A1 | 1/2013 | Hosomi et al. | |
| 2013/0017543 A1 | 1/2013 | Hosomi et al. | |

FOREIGN PATENT DOCUMENTS

| | | |
|---|---|---|
| JP | H5-506364 A | 9/1993 |
| JP | H11-239492 A | 9/1999 |
| JP | 2000-502882 A | 3/2000 |
| JP | 2003-525603 A | 9/2003 |
| JP | 2006-101791 A | 4/2006 |
| JP | 2006-204267 A | 8/2006 |
| JP | 4193997 B1 | 12/2008 |
| JP | 2010-505434 A | 2/2010 |
| JP | 2013-17427 A | 1/2013 |
| JP | 5830286 B2 | 12/2015 |
| WO | WO 92/06200 A1 | 4/1992 |
| WO | WO 94/26766 A1 | 11/1994 |
| WO | WO 97/09451 A1 | 3/1997 |
| WO | WO 01/64838 A2 | 9/2001 |
| WO | WO 2006/038673 A1 | 4/2006 |
| WO | WO 2006/080525 A1 | 8/2006 |
| WO | WO 2007/137701 A1 | 12/2007 |
| WO | WO 2008/043765 A1 | 4/2008 |

OTHER PUBLICATIONS

Amblar et al., "Biochemical Analysis of Point Mutations in the 5'-3' Exonuclease of DNA Polymerase I of *Streptococcus pneumoniae*," J. Biol. Chem. (Jun. 1, 2001), vol. 276, No. 22, pp. 19172-19181.
English translation of International Preliminary Report on Patentability and Written Opinion dated Jan. 12, 2014, in PCT International Application No. PCT/JP2012/067872.
International Search Report dated Oct. 2, 2012, in PCT International Application No. PCT/JP2012/067872.
Kaneo et al., "Tanpakushitsu Kogaku ni yoru TaqNDA Polymerase no Kino Kaihen," Japan Society for Bioscience, Biotechnology, and Agrochemistry Nishi Nippon Shibu Taikai (Dai 284 Kai) Oyobi Tokubetsu Koen Symposium Koen Yoshishu (Sep. 17, 2010), p. 30.
Kim, Y. and J. C. Shin, "Roles of the Conserved Carboxylic Residues in the Active-Site of 5'-3' Exonuclease of Taq DNA Polymerase," J. Microbiol. Biotechnol. (1999), vol. 9, No. 4. 381-385.
Kranaster et al., "One-step RNA pathogen detection with reverse transcriptase activity of a mutated thermostable Thermus aquaticus DNA polymerase," Biotechnol. J. (2010), vol. 5, pp. 224-231.
Nabe et al., Protein Engineering of Taq DNA polymerase using genetic resources from the soil samples in the seas near Okinawa, Journal of Japanese Society for Extremophiles (2007), vol. 6, pp. 150-151.
Sano et al., "Mutations to create thermostable reverse transcriptase with bacterial family A DNA polymerase from Thermotoge petrophila K4," Journal of Bioscience and Bioengineering (2012), vol. 113, No. 3, pp. 315-321.
Ngo et al., "In Protein Folding Problem and Tertiary Structure Prediction", 1994, Merz et al. (ed.), Birkhauser, Boston, MA, pp. 433 and 492-495.

* cited by examiner

*Primary Examiner* — Richard G Hutson
(74) *Attorney, Agent, or Firm* — Birch, Stewart, Kolasch & Birch, LLP

(57) ABSTRACT

Provided are various novel DNA polymerases.
Provided are: a DNA polymerase comprising: an amino acid sequence modified from the amino acid sequence of SEQ ID NO: 12, which has a substitution of arginine at position 651 by an amino acid residue having a negatively charged side chain, preferably by asparatic acid or glutamic acid, more preferably by glutamic acid; and a DNA polymerase comprising an amino acid sequence modified from the amino acid sequence of SEQ ID NO: 14, which has a substitution of proline at position 653 by an amino acid residue having a negatively charged side chain, preferably by asparatic acid or glutamic acid, more preferably by glutamic acid.

5 Claims, 11 Drawing Sheets

Specification includes a Sequence Listing.

FIG. 1-1

```
Taq   MRGMLPLFEPKGRVLLVDGHHLAYRTFHALKGLTTSRGEPVQAVYGFAKSLLKALKED-G
Tth   MEAMLPLFEPKGRVLLVDGHHLAYRTFFALKGLTTSRGEPVQAVYGFAKSLLKALKEDGY
      *..***************************.****************************

Taq   DAVIVVFDAKAPSFRHEAYGGYKAGRAPTPEDFPRQLALIKELVDLLGLARLEVPGYEAD
Tth   KAVFVVFDAKAPSFRHEAYEAYKAGRAPTPEDFPRQLALIKELVDLLGFTRLEVPGYEAD
      .**:*************** .**************************::**********

Taq   DVLASLAKKAEKEGYEVRILTADKDLYQLLSDRIHALHPEGYLITPAWLWEKYGLRPDQW
Tth   DVLATLAKKAEKEGYEVRILTADRDLYQLVSDRVAVLHPEGHLITPEWLWEKYGLRPEQW
      ****:******************:*****:***: .*****:**** ***********:**

Taq   ADYRALTGDESDNLPGVKGIGEKTARKLLEEWGSLEALLKNLDRLKP-AIREKILAHMDD
Tth   VDFRALVGDPSDNLPGVKGIGEKTALKLLKEWGSLENLLKNLDRVKPENVREKIKAHLED
      .*:***.** ***************:***:****** ********:** :**** **:.:*

Taq   LKLSWDLAKVRTDLPLEVDFAKRREPDRERLRAFLERLEFGSLLHEFGLLESPKALEEAP
Tth   LRLSLELSRVRTDLPLEVDLAQGREPDREGLRAFLERLEFGSLLHEFGLLEAPAPLEEAP
      *:** :*::**********:*: ****** *********************:* .*****

Taq   WPPPEGAFVGFVLSRKEPMWADLLALAAARGGRVHRAPEPYKALRDLKEARGLLAKDLSV
Tth   WPPPEGAFVGFVLSRPEPMWAELKALAACRDGRVHRAADPLAGLKDLKEVRGLLAKDLAV
      *************** *****:* ****.*.******.:* .:*:****.********:*

Taq   LALREGLGLPPGDDPMLLAYLLDPSNTTPEGVARRYGGEWTEEAGERAALSERLFANLWG
Tth   LASREGLDLVPGDDPMLLAYLLDPSNTTPEGVARRYGGEWTEDAAHRALLSERLHRNLLK
      ** ****.* ********************************:*..** *****. **

Taq   RLEGEERLLWLYREVERPLSAVLAHMEATGVRLDVAYLRALSLEVAEEIARLEAEVFRLA
Tth   RLEGEEKLLWLYHEVEKPLSRVLAHMEATGVRRDVAYLQALSLELAEEIRRLEEEVFRLA
      ******:*****:***:*** ********** ******:****: ****  ** ******

Taq   GHPFNLNSRDQLERVLFDELGLPAIGKTEKTGKRSTSAAVLEALREAHPIVEKILQYREL
Tth   GHPFNLNSRDQLERVLFDELRLPALGKTQKTGKRSTSAAVLEALREAHPIVEKILQHREL
      ********************  ***:***:***:*****************************:***

Taq   TKLKSTYIDPLPDLIHPRTGRLHTRFNQTATATGRLSSSDPNLQNIPVRTPLGQRIRRAF
Tth   TKLKNTYVDPLPSLVHPRTGRLHTRFNQTATATGRLSSSDPNLQNIPVRTPLGQRIRRAF
      ****.**:****.*:*********************************************
                                                              ▽
Taq   IAEEGWLLVALDYSQIELRVLAHLSGDENLIRVFQEGRDIHTETASWMFGVPREAVDPLM
Tth   VAEAGWALVALDYSQIELRVLAHLSGDENLIRVFQEGKDIHTQTASWMFGVPPEAVDPLM
      :** ** *****************************:****:********* *******

Taq   RRAAKTINFGVLYGMSAHRLSQELAIPYEEAQAFIERYFQSFPKVRAWIEKTLEEGRRRG
Tth   RRAAKTVNFGVLYGMSAHRLSQELAIPYEEAVAFIERYFQSFPKVRAWIEKTLEEGRKRG
      ******:************************ ************************:**

Taq   YVETLFGRRRYVPDLEARVKSVREAAERMAFNMPVQGTAADLMKLAMVKLFPRLEEMGAR
Tth   YVETLFGRRRYVPDLNARVKSVREAAERMAFNMPVQGTAADLMKLAMVKLFPRLREMGAR
      ***************:*************************************. *****

Taq   MLLQVHDELVLEAPKERAEAVARLAKEVMEGVYPLAVPLEVEVGIGEDWLSAKE
Tth   MLLQVHDELLLEAPQARAEEVAALAKEAMEKAYPLAVPLEVEVGMGEDWLSAKG
      *********:****: *** **..*****:***********:********
```

FIG. 1-2

```
 1          11         21         31         41         50
 |          |          |          |          |          |
MRGMLPLFEP KGRVLLVDGH HLAYRTFHAL K-GLTTSRGE PVQAVYGFAK   49 Thermus aquaticus
M--------- -ARLFLFDGT ALAYRAYYAL DRSLSTSTGI PTNATYGVAR   40 Thermotoga maritima MSB8
MVSSYLKKIP KDTVILIDGS SFIYRAYFAI PGYLATTKGF PTKAIFGVTQ   50 Thermodesulfobacterium sp. OPB4
M--------- -KTLYILDGS SFVYRSFFAL P-PLSTSKGF PTNAIYGFLR   39 Aquifex aeolicus VF5
M--------- ---------- ---------- ---------- ----------    1 Aquifex aeolicus VF5

SLLKALKE-- --DGDAVIVV FDAKAPSFRH EAYGGYKAGR APTPEDFPRQ   95 Taq-Pol
MLVRFIKDHI IVGKDYVAVA FDKKAATFRH KLLETYKAQR PKTPDLLIQQ   90 gi|15644367|ref|NP_229419.1|
MVLKILKEW- --DPEYIIWF MDEKEPTFRH EIYENYKATR PKMPDDLKIQ   97 gi|337288350|ref|YP_004627822.1|
MLFSLIKKE- --RPQYLVVV FDAPAKTKRE KIYADYKKQR PKAPDPLKVQ   86 gi|15606735|ref|NP_214115.1|
---------- ---------- ---------- ---------- ----------    1 gi|15606966|ref|NP_214348.1|Aquifex LALIKELVDL LGLARLEVPG YEADDVLASL AKK-AEKEGY EVRILTADKD  144 Taq-Pol
LPYIKKLVEA LGMKVLEVEG YEADDIIATL AVK-GLPLFD EIFIVTGDKD  139 gi|15644367|ref|NP_229419.1|
IPYIRNIIHS LGIPVLSHPG YEGDDLIASF IKNIIKKQNL SAIIVAGDKD  147 gi|337288350|ref|YP_004627822.1|
IPVIKEILKL AGIPLLELPG YEADDVIAYL AEK-FSQKGF KVKIYSPDKD  135 gi|15606735|ref|NP_214115.1|
---------- ---------- ---------- ---------- ----------    1 gi|15606966|ref|NP_214348.1|Aquifex LYQLLSDRIH VLHP-----E GYLITPAWLW EKYGLRPDQW ADYRALTGDE  189 Taq-Pol
MLQLVNEKIK VWRIVKGISD LELYDAQKVK EKYGVEPQQI PDLLALTGDE  189 gi|15644367|ref|NP_229419.1|
LYSLIDKNIA IYDPVR---E -KFLDLDAFL EKYQFPPQVF PEFRALTGDP  193 gi|337288350|ref|YP_004627822.1|
LLQLVSENVL VINPMN---D -EVFTKERVI KKFGVEPQKI PDYLALVGDK  181 gi|15606735|ref|NP_214115.1|
---------- ---------- ---------- ---------- -DFEYVTGEE   10 gi|15606966|ref|NP_214348.1|Aquifex SDNLPGVKGI GEKTARKLLE EWGSLEALLK NLDRLK-PAI REKILAHMDD  238 Taq-Pol
IDNIPGVTGI GEKTAVQLLE KYKDLEDILN HVRELP-QKV RKALLRDREN  238 gi|15644367|ref|NP_229419.1|
SDNIPGVPGI GEKTAKELLI KFKNLENLYQ NIKQVSLSKL RESLLYKDQ   243 gi|337288350|ref|YP_004627822.1|
VDNVPGIEGV GPKTAINILK KYGSVENILK NWEKFQ---- REFPRAKKED  227 gi|15606735|ref|NP_214115.1|
---------- GLKKAIKRLE ---------- ---------- ----------   20 gi|15606966|ref|NP_214348.1|Aquifex LKLSWDLAKV RTDLPL-EVD FA--KRREPD RERLRAFLER LEFGSLLHEF  285 Taq-Pol
AILSKKLAIL ETNVPI-EIN WEELRYQGYD REKLLPLLKE LEFASIMKEL  287 gi|15644367|ref|NP_229419.1|
VLNNLSLLTL NYNAPLPSLD IIYYKRKEPD YSTLRKIFKE LEFRKLLSEI  293 gi|337288350|ref|YP_004627822.1|
LELSYKLVKL YTDLDI-ELS EEDLKIKRPD LNKLKQKLQE LEMKSLLKEV  276 gi|15606735|ref|NP_214115.1|
---------- --NSPYLYLD TE----TTGD RIRLVQIGDE ----------   44 gi|15606966|ref|NP_214348.1|Aquifex GLLESPKA-- ---------- ---------- ------LEEA PWPPPEGAFV  307 Taq-Pol
QLYEESEPVG YRIVKDLVEF EKLIEKLRES PSFAIDLETS SLDPFDCDIV  337 gi|15644367|ref|NP_229419.1|
KYTPP----- ---------- -EFKPLLIEN KDLSQIPERD YLSLFPLQYQ  327 gi|337288350|ref|YP_004627822.1|
---------- ---------- ---------- ---------- ----------  276 gi|15606735|ref|NP_214115.1|
---------- ---------- ---------- ---------- ----------   44 gi|15606966|ref|NP_214348.1|Aquifex GFVLSRKEPM WADLLALAAA RGGRVHRAPE PYKALRDLKE ARG--L----  351 Taq-Pol
GISVSFK-PK EAYYIPL-HH RNAQNLDEKE VLKKLKEILE DPGAKIVGQN  385 gi|15644367|ref|NP_229419.1|
GYIFNLAH-- -APEIAVAFS EKEAYKLSTS CLKDLISKFT KTK--F----  368 gi|337288350|ref|YP_004627822.1|
---------- ---------- ---------- ---------- ----------  276 gi|15606735|ref|NP_214115.1|
---------E NTYVIDL--- ------YEIQ DIEPLRKLIN ERG--IVGHN   74 gi|15606966|ref|NP_214348.1|Aquifex LAKDLSVLAL REGLGLPPGD DPMLLAYLLD PSNT--TPEG VARRYGG---  396 Taq-Pol
LKFDYKVLMV KGVEPVPPYF DTMIAAYLLE PNEKKFNLDD LALKFLGYKM  435 gi|15644367|ref|NP_229419.1|
ILHDYKNFLK LFGFSLNKVF DTKLASYLLN PSLKKYELEF LLQEYLDISL  418 gi|337288350|ref|YP_004627822.1|
---------- ---------- ---------- ---------- ----------  276 gi|15606735|ref|NP_214115.1|
LKFDLK-YLY RYGIFPSATF DTMIASYLL- -GYERHSLNH IVSNLLGYSM  121 gi|15606966|ref|NP_214348.1|Aquifex ---------- ---------- ----EWTEEA GERAALSERL F---ANLWGR  419 Taq-Pol
TSYQELMSFS FPLFGFSFAD VPVEKAANYS CEDADITYRL Y---KTLSLK  482 gi|15644367|ref|NP_229419.1|
GS-------- ---------- ----SKISED EEIAIKTCSL FLLGKELINR  446 gi|337288350|ref|YP_004627822.1|
---------- ---------- ---------- ---------- ----------  276 gi|15606735|ref|NP_214115.1|
DK-----SYQ TSDWGASVLS D---AQLKYA ANDVIVLREL FPKMRDMLNE  163 gi|15606966|ref|NP_214348.1|Aquifex LEGEE----- #NAME?     LWLYREVERP LSAVLAHMEA TGVRLDVA--  454 Taq-Pol
LH-EA----- #NAME?     ENVFYKIEMP LVNVLARMEL NGVYVDTE--  516 gi|15644367|ref|NP_229419.1|
IE-EE----- #NAME?     SEWLEKVEIP LSEVLFEMEK KGFKIDLE--  480 gi|337288350|ref|YP_004627822.1|
---------- ---------- ---------- ---------- ----------  276 gi|15606735|ref|NP_214115.1|
LDAERGEELL KTRTAKIFDL KSPVAIVEMA FVREVAKLEI NGFPVDVEEL  213 gi|15606966|ref|NP_214348.1|Aquifex
```

FIG. 1-3

```
--YLRALSLE VAEEIARLEA EVFRLAGHPF NLNSRDQLER VLFDELGLPA  502 Taq-Pol
--FLKKLSEE YGKKLEELAE EIYRIAGEPF NINSPKQVSR ILFEKLGIKP  564 gi|15644367|ref|NP_229419.1|
--YVRTLNQE YQKTLKELED KLFEIAGCRF NPKSSQEVSN ILFKKLNLPS  528 gi|337288350|ref|YP_004627822.1|
---------- ---------D KIFRQASQR- ---------- ----------  286 gi|15606735|ref|NP_214115.1|
TNKLKAVERE TQKRIQEFYI K------YRV DPLSPKQLAS LLTKKFKL-N  256 gi|15606966|ref|NP_214348.1|Aquifex IGKTEKTGKR STSAAVLEAL REAHPIVEKI LQYRELTKLK STYIDPLPDL  552 Taq-Pol
RGKTTKTGDY STRIEVLEEL AGEHEIIPLI LEYRKIQKLK STYIDALPKM  614 gi|15644367|ref|NP_229419.1|
IKKTPKSSLP STDAEVLEEL APLHPFVRLL IQYRTLYKIK STYLEAFLKY  578 gi|337288350|ref|YP_004627822.1|
---------- ---------- ---------- ---------- ----------  286 gi|15606735|ref|NP_214115.1|
LPKTPK-GNV STDDKALTSY QDVEP-VKLV LEIRKLKKIA ----DKLKEL  300 gi|15606966|ref|NP_214348.1|Aquifex I-HPRTGRLH TRFNQTATAT GRLSSSDPNL QNIPVRTPLG QRIRRAFIAE  601 Taq-Pol
V-NPKTGRIH ASFNQTGTAT GRLSSSDPNL QNLPTKSEEG KEIRKAIVPQ  663 gi|15644367|ref|NP_229419.1|
A-ETKTHRLH TEFNQTGTAT GRLSSQNPNL QNIPIKGEEG LSIRRAFIAE  627 gi|337288350|ref|YP_004627822.1|
---------- ---------- ---------- ---------- ----------  286 gi|15606735|ref|NP_214115.1|
KEHLKNGRVY PEFKQIGAVT GRMSSAHPNI QNI------H RDMRGIFKAE  344 gi|15606966|ref|NP_214348.1|Aquifex E-GWLLVALD YSQIELRVLA HLSGDENLIR VFQEGRDIHT ETASWMFGVP  650 Taq-Pol
DPNWWIVSAD YSQIELRILA HLSGDENLLR AFEEGIDVHT LTASRIFNVK  713 gi|15644367|ref|NP_229419.1|
D-GCMLCSLD YSQIELRILA HFSEDKNLIS AFEKGEDIHT FTACEVFGVT  676 gi|337288350|ref|YP_004627822.1|
---------- ---------- ---------- ---------- ----------  286 gi|15606735|ref|NP_214115.1|
E-GNTFVISD FSQIELRIAA EYVKDPLMLD AFKKGKDMHR YTASVVLGKK  393 gi|15606966|ref|NP_214348.1|Aquifex
▼
REAVDPLMRR AAKTINFGVL YGMSAHRLSQ ELA------I PYEEAQAFIE  694 Taq-Pol
PEEVTEEMRR AGKMVNFSII YGVTPYGLSV RLG------V PVKEAEKMIV  757 gi|15644367|ref|NP_229419.1|
PEKVTPEMRR MSKAINFGIA YGMSAYGLAK ELK------I SPKEAEIIIN  720 gi|337288350|ref|YP_004627822.1|
---------- ---------- ---------- ---------- ----------  286 gi|15606735|ref|NP_214115.1|
EEEITKEERQ LAKAINFGLI YGISAKGLAE YAKLGYGVEI SLEEAQVLRE  443 gi|15606966|ref|NP_214348.1|Aquifex RYFQSFPKVR AWIEKTLEEG RRRGYVE--T LFGRRRYVPD LEARGPRRAP  742 Taq-Pol
NYFVLYPKVR DYIQRVVSEA KEKGYVR--T LFGRKRDIPQ LMARD-----  800 gi|15644367|ref|NP_229419.1|
RYFSRYPGIK EYIQKTIEFA KENGYVK--T LVGRKRYIPE LFSPN-----  763 gi|337288350|ref|YP_004627822.1|
---------- ---------- --------S LF-------- ----------  289 gi|15606735|ref|NP_214115.1|
RFFKNFKAFK EWHDRVKKEL KEKGEVKGHT LLGRR----- ----------  478 gi|15606966|ref|NP_214348.1|Aquifex RRLVKSVREA AERMAFNMPV QGTAADLMKL AMVKLFPRLE E--MGARMLL  790 Taq-Pol
----RNTQAE GERIAINTPI QGTAADIIKL AMIEIDRELK ERKMRSKMII  846 gi|15644367|ref|NP_229419.1|
----KSIKEL GQRMAINTPI QGSAADLIKC AMVALQKELK RHNLKTAIIL  809 gi|337288350|ref|YP_004627822.1|
---------- ---------- ---------- ---------- ----------  289 gi|15606735|ref|NP_214115.1|
------FSAN TFNDAVNYPI QGTGADLLKL AVLLFDANLQ KKGIDAKLVN  522 gi|15606966|ref|NP_214348.1|Aquifex QVHDELVLEA PKERAEAVAR LAKEVMEGV- ------YPLA VPLEVEVGIG  833 Taq-Pol
QVHDELVFEV PNEEKDALVE LVKDRMTNV- ------VKLS VPLEVDVTIG  889 gi|15644367|ref|NP_229419.1|
QVHDELVLEV PEEEIEIIKE LAPKIMENPF KYLNLPYKLN VPIKVNFSFG  859 gi|337288350|ref|YP_004627822.1|
---------- ---------- ---------- ---------- ----------  289 gi|15606735|ref|NP_214115.1|
LVHDEIVVEC EKEKAEEVKE ILEKSMKTAG KI----ILKE VPVEVESVIN  568 gi|15606966|ref|NP_214348.1|Aquifex EDWLSAKE                                              841 Taq-Pol
KTWS----                                              893 gi|15644367|ref|NP_229419.1|
KNWAECK-                                              866 gi|337288350|ref|YP_004627822.1|
--------                                              289 gi|15606735|ref|NP_214115.1|
ERWT--KD                                              574 gi|15606966|ref|NP_214348.1|Aquifex
```

FIG. 6

Taq WT nucleotide sequence (2499 bp)  SEQ ID NO: 11

ATGAGGGGGATGCTGCCCCTCTTTGAGCCCAAGGGCCGGGTCCTCCTGGTGGACGGCCACCACCTGGCCTACCGCACCTTCCACGCC
CTGAAGGGCCTCACCACCAGCCGGGGGGAGCCGGTGCAGGCGGTCTACGGCTTCGCCAAGAGCCTCCTCAAGGCCCTCAAGGAGGAC
GGGGACGCGGTGATCGTGGTCTTTGACGCCAAGGCCCCCTCCTTCCGCCACGAGGCCTACGGGGGGTACAAGGCGGGCCGGGCCCCC
ACGCCGGAGGACTTTCCCCGGCAACTCGCCCTCATCAAGGAGCTGGTGGACCTCCTGGGGCTGGCGCGCCTCGAGGTCCCGGGCTAC
GAGGCGGACGACGTCCTGGCCAGCCTGGCCAAGAAGGCGGAAAAGGAGGGCTACGAGGTCCGCATCCTCACCGCCGACAAAGACCTT
TACCAGCTCCTTTCCGACCGCATCCACGTCCTCCACCCCGAGGGGTACCTCATCACCCCGGCCTGGCTTTGGGAAAAGTACGGCCTG
AGGCCCGACCAGTGGGCCGACTACCGGGCCCTGACCGGGGACGAGTCCGACAACCTTCCCGGGGTCAAGGGCATCGGGGAGAAGACG
GCGAGGAAGCTTCTGGAGGAGTGGGGGAGCCTGGAAGCCCTCCTCAAGAACCTGGACCGGCTGAAGCCCGCCATCCGGGAGAAGATC
CTGGCCCACATGGACGATCTGAAGCTCTCCTGGGACCTGGCCAAGGTGCGCACCGACCTGCCCCTGGAGGTGGACTTCGCCAAAAGG
CGGGAGCCCGACCGGGAGAGGCTTAGGGCCTTTCTGGAGAGGCTTGAGTTTGGCAGCCTCCTCCACGAGTTCGGCCTTCTGGAAAGC
CCCAAGGCCCTGGAGGAGGCCCCCTGGCCCCCGCCGGAAGGGGCCTTCGTGGGCTTTGTGCTTTCCCGCAAGGAGCCCATGTGGGCC
GATCTTCTGGCCCTGGCCGCCGCCAGGGGGGGCCGGGTCCACCGGGCCCCCGAGCCTTATAAAGCCCTCAGGGACCTGAAGGAGGCG
CGGGGGCTTCTCGCCAAAGACCTGAGCGTTCTGGCCCTGAGGGAAGGCCTTGGCCTCCCGCCCGGCGACGACCCCATGCTCCTCGCC
TACCTCCTGGACCCTTCCAACACCACCCCCGAGGGGGTGGCCCGGCGCTACGGCGGGGAGTGGACGGAGGAGGCGGGGGAGCGGGCC
GCCCTTTCCGAGAGGCTCTTCGCCAACCTGTGGGGGAGGCTTGAGGGGGAGGAGAGGCTCCTTTGGCTTTACCGGGAGGTGGAGAGG
CCCCTTTCCGCTGTCCTGGCCCACATGGAGGCCACGGGGGTGCGCCTGGACGTGGCCTATCTCAGGGCCTTGTCCCTGGAGGTGGCC
GAGGAGATCGCCCGCCTCGAGGCCGAGGTCTTCCGCCTGGCCGGCCACCCCTTCAACCTCAACTCCCGGGACCAGCTGGAAAGGGTC
CTCTTTGACGAGCTAGGGCTTCCCGCCATCGGCAAGACGGAGAAGACCGGCAAGCGCTCCACCAGCGCCGCCGTCCTGGAGGCCCTC
CGCGAGGCCCACCCCATCGTGGAGAAGATCCTGCAGTACCGGGAGCTCACCAAGCTGAAGAGCACCTACATTGACCCCTTGCCGGAC
CTCATCCACCCCAGGACGGGCCGCCTCCACACCCGCTTCAACCAGACGGCCACGGCCACGGGCAGGCTAAGTAGCTCCGATCCCAAC
CTCCAGAACATCCCCGTCCGCACCCCGCTTGGGCAGAGGATCCGCCGGGCCTTCATCGCCGAGGAGGGGTGGCTATTGGTGGCCCTG
GACTATAGCCAGATAGAGCTCAGGGTGCTGGCCCACCTCTCCGGCGACGAGAACCTGATCCGGGTCTTCCAGGAGGGGCGGGACATC
CACACGGAGACCGCCAGCTGGATGTTCGGCGTCCCCCGGGAGGCCGTGGACCCCCTGATGCGCCGGGCGGCCAAGACCATCAACTTC
GGGGTCCTCTACGGCATGTCGGCCCACCGCCTCTCCCAGGAGCTAGCCATCCCTTACGAGGAGGCCCAGGCCTTCATTGAGCGCTAC
TTTCAGAGCTTCCCCAAGGTGCGGGCCTGGATTGAGAAGACCCTGGAGGAGGGCAGGAGGCGGGGGTACGTGGAGACCCTCTTCGGC
CGCCGCCGCTACGTGCCAGACCTAGAGGCCCGGGTGAAGAGCGTGCGGGAGGCCGGCCGAGCGCATGGCCTTCAACATGCCCGTCCAG
GGCACCGCCGCCGACCTCATGAAGCTGGCTATGGTGAAGCTCTTCCCCAGGCTGGAGGAAATGGGGGCCAGGATGCTCCTTCAGGTC
CACGACGAGCTGGTCCTCGAGGCCCCAAAAGAGAGGGCGGAGGCCGTGGCCCGGCTGGCCAAGGAGGTCATGGAGGGGGTGTATCCC
CTGGCCGTGCCCCTGGAGGTGGAGGTGGGGATAGGGGAGGACTGGCTCTCCGCCAAGGAGTGA

Taq WT amino acid sequence (832 amino acids)  SEQ ID NO: 12

MRGMLPLFEPKGRVLLVDGHHLAYRTFHALKGLTTSRGEPVQAVYGFAKSLLKALKEDGDAVIVVFDAKAPSFRHEAYGGYKAGRAP
TPEDFPRQLALIKELVDLLGLARLEVPGYEADDVLASLAKKAEKEGYEVRILTADKDLYQLLSDRIHVLHPEGYLITPAWLWEKYGL
RPDQWADYRALTGDESDNLPGVKGIGEKTARKLLEEWGSLEALLKNLDRLKPAIREKILAHMDDLKLSWDLAKVRTDLPLEVDFAKR
REPDRERLRAFLERLEFGSLLHEFGLLESPKALEEAPWPPPEGAFVGFVLSRKEPMWADLLALAAARGGRVHRAPEPYKALRDLKEA
RGLLAKDLSVLALREGLGLPPGDDPMLLAYLLDPSNTTPEGVARRYGGEWTEEAGERAALSERLFANLWGRLEGEERLLWLYREVER
PLSAVLAHMEATGVRLDVAYLRALSLEVAEEIARLEAEVFRLAGHPFNLNSRDQLERVLFDELGLPAIGKTEKTGKRSTSAAVLEAL
REAHPIVEKILQYRELTKLKSTYIDPLPDLIHPRTGRLHTRFNQTATATGRLSSSDPNLQNIPVRTPLGQRIRRAFIAEEGWLLVAL
DYSQIELRVLAHLSGDENLIRVFQEGRDIHTETASWMFGVPREAVDPLMRRAAKTINFGVLYGMSAHRLSQELAIPYEEAQAFIERY
FQSFPKVRAWIEKTLEEGRRRGYVETLFGRRRYVPDLEARVKSVREAAERMAFNMPVQGTAADLMKLAMVKLFPRLEEMGARMLLQV
HDELVLEAPKERAEAVARLAKEVMEGVYPLAVPLEVEVGIGEDWLSAKE

FIG. 7

Tth WT nucleotide sequence (2505 bp)  SEQ ID NO: 13

ATGGAGGCGATGCTTCCGCTCTTTGAACCCAAAGGCCGGGTCCTCCTGGTGGACGGCCACCACCTGGCCTACCGCACCTTCTTCGCC
CTGAAGGGCCTCACCACGAGCCGGGGCGAACCGGTGCAGGCGGTCTACGGCTTCGCCAAGAGCCTCCTCAAGGCCCTGAAGGAGGAC
GGGTACAAGGCCGTCTTCGTGGTCTTTGACGCCAAGGCCCCCTCCTTCCGCCACGAGGCCTACGAGGCCTACAAGGCGGGGAGGGCC
CCGACCCCCGAGGACTTCCCCCGGCAGCTCGCCCTCATCAAGGAGCTGGTGGACCTCCTGGGGTTTACCCGCCTCGAGGTCCCCGGC
TACGAGGCGGACGACGTTCTCGCCACCCTGGCCAAGAAGGCGGAAAAGGAGGGGTACGAGGTGCGCATCCTCACCGCCGACCGCGAC
CTCTACCAACTCGTCTCCGACCGCGTCGCCGTCCTCCACCCCGAGGGCCACCTCATCACCCCGGAGTGGCTTTGGGAGAAGTACGGC
CTCAGGCCGGAGCAGTGGGTGGACTTCCGCGCCCTCGTGGGGGACCCCTCCGACAACCTCCCCGGGGTCAAGGGCATCGGGGAGAAG
ACCGCCCTCAAGCTCCTCAAGGAGTGGGGAAGCCTGGAAAACCTCCTCAAGAACCTGGACCGGGTAAAGCCAGAAAACGTCCGGGAG
AAGATCAAGGCCCACCTGGAAGACCTCAGGCTCTCCTTGGAGCTCTCCCGGGTGCGCACCGACCTCCCCCTGGAGGTGGACCTCGCC
CAGGGGCGGGAGCCCGACCGGGAGGGGCTTAGGGCCTTCCTGGAGAGGCTGGAGTTCGGCAGCCTCCTCCACGAGTTCGGCCTCCTG
GAGGCCCCCGCCCCCCTGGAGGAGGCCCCCTGGCCCCCGCCGGAAGGGGCCTTCGTGGGCTTCGTCCTCTCCCGCCCCGAGCCCATG
TGGGCGGAGCTTAAAGCCCTGGCCGCCTGCAGGGACGGCCGGGTGCACCGGGCAGCAGACCCCTTGGCGGGGCTAAAGGACCTCAAG
GAGGTCCGGGGCCTCCTCGCCAAGGACCTCGCCGTCTTGGCCTCGAGGGAGGGGCTAGACCTCGTGCCCGGGGACGACCCCATGCTC
CTCGCCTACCTCCTGGACCCCTCCAACACCACCCCCGAGGGGGTGGCGCGGCGCTACGGGGGGGAGTGGACGGAGGACGCCGCCCAC
CGGGCCCTCCTCTCGGAGAGGCTCCATCGGAACCTCCTTAAGCGCCTCGAGGGGGAGGAGAAGCTCCTTTGGCTCTACCACGAGGTG
GAAAAGCCCCTCTCCCGGGTCCTGGCCCACATGGAGGCCACCGGGGTACGGCGGGACGTGGCCTACCTTCAGGCCCCTTTCCCTGGAG
CTTGCGGAGGAGATCCGCCGCCTCGAGGAGGAGGTCTTCCGCTTGGCGGGCCACCCCTTCAACCTCAACTCCCGGGACCAGCTGGAA
AGGGTGCTCTTTGACGAGCTTAGGCTTCCCGCCTTGGGGAAGACGCAAAAGACAGGCAAGCGCTCCACCAGCGCCGCGGTGCTGGAG
GCCCTACGGGAGGCCCACCCCATCGTGGAGAAGATCCTCCAGCACCGGGAGCTCACCAAGCTCAAGAACACCTACGTGGACCCCCTC
CCAAGCCTCGTCCACCCGAGGACGGGCCGCCTCCACACCCGCTTCAACCAGACGGCCACGGCCACGGGGAGGCTTAGTAGCTCCGAC
CCCAACCTGCAGAACATCCCCGTCCGCACCCCCTTGGGCCAGAGGATCCGCCGGGCCTTCGTGGCCGAGGCGGGTTGGGCGTTGGTG
GCCCTGGACTATAGCCAGATAGAGCTCCGCGTCCTCGCCCACCTCTCCGGGGACGAAAACCTGATCAGGGTCTTCCAGGAGGGGAAG
GACATCCACACCCAGACCGCAAGCTGGATGTTCGGCGTCCCCCCGGAGGCCGTGGACCCCCTGATGCGCCGGGCGGCCAAGACGGTG
AACTTCGGCGTCCTCTACGGCATGTCCGCCCATAGGCTCTCCCAGGAGCTTGCCATCCCCTACGAGGAGGCGGTGGCCTTTATAGAG
CGCTACTTCCAAAGCTTCCCCAAGGTGCGGGCCTGGATAGAAAAGACCCTGGAGGAGGGGAGGAAGCGGGGCTACGTGGAAACCCTC
TTCGGAAGAAGGCGCTACGTGCCCGACCTCAACGCCCGGGTGAAGAGCGTCAGGGAGGCCGCGGAGCGCATGGCCTTCAACATGCCC
GTCCAGGGCACCGCCGCCGACCTCATGAAGCTCGCCATGGTGAAGCTCTTCCCCCGCCTCCGGGAGATGGGGGCCCGCATGCTCCTC
CAGGTCCACGACGAGCTCCTCCTGGAGGCCCCCCAAGCGCGGGCCGAGGAGGTGGCGGCTTTGGCCAAGGAGGCCATGGAGAAGGCC
TATCCCCTCGCCGTGCCCCTGGAGGTGGAGGTGGGGATGGGGGAGGACTGGCTTTCCGCCAAGGGTTAG

Tth WT amino acid sequence (834 amino acids)  SEQ ID NO: 14

MEAMLPLFEPKGRVLLVDGHHLAYRTFFALKGLTTSRGEPVQAVYGFAKSLLKALKEDGYKAVFVVFDAKAPSFRHEAYEAYKAGRA
PTPEDFPRQLALIKELVDLLGFTRLEVPGYEADDVLATLAKKAEKEGYEVRILTADRDLYQLVSDRVAVLHPEGHLITPEWLWEKYG
LRPEQWVDFRALVGDPSDNLPGVKGIGEKTALKLLKEWGSLENLLKNLDRVKPENVREKIKAHLEDLRLSLELSRVRTDLPLEVDLA
QGREPDREGLRAFLERLEFGSLLHEFGLLEAPAPLEEAPWPPPEGAFVGFVLSRPEPMWAELKALAACRDGRVHRAADPLAGLKDLK
EVRGLLAKDLAVLASREGLDLVPGDDPMLLAYLLDPSNTTPEGVARRYGGEWTEDAAHRALLSERLHRNLLKRLEGEEKLLWLYHEV
EKPLSRVLAHMEATGVRRDVAYLQALSLELAEEIRRLEEEVFRLAGHPFNLNSRDQLERVLFDELRLPALGKTQKTGKRSTSAAVLE
ALREAHPIVEKILQHRELTKLKNTYVDPLPSLVHPRTGRLHTRFNQTATATGRLSSSDPNLQNIPVRTPLGQRIRRAFVAEAGWALV
ALDYSQIELRVLAHLSGDENLIRVFQEGKDIHTQTASWMFGVPPEAVDPLMRRAAKTVNFGVLYGMSAHRLSQELAIPYEEAVAFIE
RYFQSFPKVRAWIEKTLEEGRKRGYVETLFGRRRYVPDLNARVKSVREAAERMAFNMPVQGTAADLMKLAMVKLFPRLREMGARMLL
QVHDELLLEAPQARAEEVAALAKEAMEKAYPLAVPLEVEVGMGEDWLSAKG

FIG. 8

Taq Exo⁻ nucleotide sequence　　　　　　　　　　　　SEQ ID NO: 15
ATGAGGGGGATGCTGCCCCTCTTTGAGCCCAAGGGCCGGGTCCTCCTGGTGGACGGCCACCACCTGGCCTACCGCACCTTCCACGCC
CTGAAGGGCCTCACCACCAGCCGGGGGGAGCCGGTGCAGGCGGTCTACGGCTTCGCCAAGAGCCTCCTCAAGGCCCTCAAGGAGGAC
GGGGACGCGGTGATCGTGGTCTTTGACGCCAAGGCCCCCTCCTTCCGCCACGAGGCCTACGGGGGGTACAAGGCGGGCCGGGCCCCC
ACGCCGGAGGACTTTCCCCGGCAACTCGCCCTCATCAAGGAGCTGGTGGACCTCCTGGGGCTGGCGCGCCTCGAGGTCCCGGGCTAC
GCGGCGGCCGACGTCCTGGCCAGCCTGGCCAAGAAGGCGGAAAAGGAGGGCTACGAGGTCCGCATCCTCACCGCCGCCAAAGCCCTT
TACCAGCTCCTTTCCGACCGCATCCACGTCCTCCACCCCGAGGGGTACCTCATCACCCCGGCCTGGCTTTGGGAAAAGTACGGCCTG
AGGCCCGACCAGTGGGCCGACTACCGGGCCCTGACCGGGGACGAGTCCGACAACCTTCCCGGGGTCAAGGGCATCGGGGAGAAGACG
GCGAGGAAGCTTCTGGAGGAGTGGGGGAGCCTGGAAGCCCTCCTCAAGAACCTGGACCGGCTGAAGCCCGCCATCCGGGAGAAGATC
CTGGCCCACATGGACGATCTGAAGCTCTCCTGGGACCTGGCCAAGGTGCGCACCGACCTGCCCCTGGAGGTGGACTTCGCCAAAAGG
CGGGAGCCCGACCGGGAGAGGCTTAGGGCCTTTCTGGAGAGGCTTGAGTTTGGCAGCCTCCTCCACGAGTTCGGCCTTCTGGAAAGC
CCCAAGGCCCTGGAGGAGGCCCCCTGGCCCCCGCCGGAAGGGGCCTTCGTGGGCTTTGTGCTTTCCCGCAAGGAGCCCATGTGGGCC
GATCTTCTGGCCCTGGCCGCCGCCAGGGGGGGCCGGGTCCACCGGGCCCCCGAGCCTTATAAAGCCCTCAGGGACCTGAAGGAGGCG
CGGGGGCTTCTCGCCAAAGACCTGAGCGTTCTGGCCCTGAGGGAAGGCCTTGGCCTCCCGCCCGGCGACGACCCCATGCTCCTCGCC
TACCTCCTGGACCCTTCCAACACCACCCCCGAGGGGGTGGCCCGGCGCTACGGCGGGGAGTGGACGGAGGAGGCGGGGAGCGGGCC
GCCCTTTCCGAGAGGCTCTTCGCCAACCTGTGGGGGAGGCTTGAGGGGGAGGAGAGGCTCCTTTGGCTTTACCGGGAGGTGGAGAGG
CCCCTTTCCGCTGTCCTGGCCCACATGGAGGCCACGGGGGTGCGCCTGGACGTGGCCTATCTCAGGGCCTTGTCCCTGGAGGTGGCC
GAGGAGATCGCCCGCCTCGAGGCCGAGGTCTTCCGCCTGGCCGGCCACCCCTTCAACCTCAACTCCCGGGACCAGCTGGAAAGGGTC
CTCTTTGACGAGCTAGGGCTTCCCGCCATCGGCAAGACGGAGAAGACCGGCAAGCGCTCCACCAGCGCCGCCGTCCTGGAGGCCCTC
CGCGAGGCCCACCCCATCGTGGAGAAGATCCTGCAGTACCGGGAGCTCACCAAGCTGAAGAGCACCTACATTGACCCCTTGCCGGAC
CTCATCCACCCCAGGACGGGCCGCCTCCACACCCGCTTCAACCAGACGGCCACGGCCACGGGCAGGCTAAGTAGCTCCGATCCCAAC
CTCCAGAACATCCCCGTCCGCACCCCGCTTGGGCAGAGGATCCGCCGGGCCTTCATCGCCGAGGAGGGGTGGCTATTGGTGGCCCTG
GACTATAGCCAGATAGAGCTCAGGGTGCTGGCCCACCTCTCCGGCGACGAGAACCTGATCCGGGTCTTCCAGGAGGGGCGGGACATC
CACACGGAGACCGCCAGCTGGATGTTCGGCGTCCCCCGGGAGGCCGTGGACCCCCTGATGCGCCGGGCGGCCAAGACCATCAACTTC
GGGGTCCTCTACGGCATGTCGGCCCACCGCCTCTCCCAGGAGCTAGCCATCCCTTACGAGGAGGCCCAGGCCTTCATTGAGCGCTAC
TTTCAGAGCTTCCCCAAGGTGCGGGCCTGGATTGAGAAGACCCTGGAGGAGGGCAGGAGGCGGGGGTACGTGGAGACCCTCTTCGGC
CGCCGCCGCTACGTGCCAGACCTAGAGGCCCGGGTGAAGAGCGTGCGGGAGGCGGCCGAGCGCATGGCCTTCAACATGCCCGTCCAG
GGCACCGCCGCCGACCTCATGAAGCTGGCTATGGTGAAGCTCTTCCCCAGGCTGGAGGAAATGGGGGCCAGGATGCTCCTTCAGGTC
CACGACGAGCTGGTCCTCGAGGCCCCAAAAGAGAGGGCGGAGGCCGTGGCCCGGCTGGCCAAGGAGGTCATGGAGGGGGTGTATCCC
CTGGCCGTGCCCCTGGAGGTGGAGGTGGGGATAGGGGAGGACTGGCTCTCCGCCAAGGAGTGA

Taq Exo⁻ amino acid sequence　　　　　　　　　　　　SEQ ID NO: 16
MRGMLPLFEPKGRVLLVDGHHLAYRTFHALKGLTTSRGEPVQAVYGFAKSLLKALKEDGDAVIVVFDAKAPSFRHEAYGGYKAGRAP
TPEDFPRQLALIKELVDLLGLARLEVPGYAAADVLASLAKKAEKEGYEVRILTAAKALYQLLSDRIHVLHPEGYLITPAWLWEKYGL
RPDQWADYRALTGDESDNLPGVKGIGEKTARKLLEEWGSLEALLKNLDRLKPAIREKILAHMDDLKLSWDLAKVRTDLPLEVDFAKR
REPDRERLRAFLERLEFGSLLHEFGLLESPKALEEAPWPPPEGAFVGFVLSRKEPMWADLLALAAARGGRVHRAPEPYKALRDLKEA
RGLLAKDLSVLALREGLGLPPGDDPMLLAYLLDPSNTTPEGVARRYGGEWTEEAGERAALSERLFANLWGRLEGEERLLWLYREVER
PLSAVLAHMEATGVRLDVAYLRALSLEVAEEIARLEAEVFRLAGHPFNLNSRDQLERVLFDELGLPAIGKTEKTGKRSTSAAVLEAL
REAHPIVEKILQYRELTKLKSTYIDPLPDLIHPRTGRLHTRFNQTATATGRLSSSDPNLQNIPVRTPLGQRIRRAFIAEEGWLLVAL
DYSQIELRVLAHLSGDENLIRVFQEGRDIHTETASWMFGVPREAVDPLMRRAAKTINFGVLYGMSAHRLSQELAIPYEEAQAFIERY
FQSFPKVRAWIEKTLEEGRRRGYVETLFGRRRYVPDLEARVKSVREAAERMAFNMPVQGTAADLMKLAMVKLFPRLEEMGARMLLQV
HDELVLEAPKERAEAVARLAKEVMEGVYPLAVPLEVEVGIGEDWLSAKE

FIG. 9

Taq Exo⁻ + E742A nucleotide sequence                 SEQ ID NO: 17

ATGAGGGGGATGCTGCCCCTCTTTGAGCCCAAGGGCCGGGTCCTCCTGGTGGACGGCCACCACCTGGCCTACCGCACCTTCCACGCC
CTGAAGGGCCTCACCACCAGCCGGGGGGAGCCGGTGCAGGCGGTCTACGGCTTCGCCAAGAGCCTCCTCAAGGCCCTCAAGGAGGAC
GGGGACGCGGTGATCGTGGTCTTTGACGCCAAGGCCCCCTCCTTCCGCCACGAGGCCTACGGGGGGTACAAGGCGGGCCGGGCCCCC
ACGCCGGAGGACTTTCCCCGGCAACTCGCCCTCATCAAGGAGCTGGTGGACCTCCTGGGGCTGGCGCGCCTCGAGGTCCGGGCTAC
GCGGCGGCCGACGTCCTGGCCAGCCTGGCCAAGAAGGCGGAAAAGGAGGGCTACGAGGTCCGCATCCTCACCGCCGCCAAAGCCCTT
TACCAGCTCCTTTCCGACCGCATCCACGTCCTCCACCCCGAGGGGTACCTCATCACCCCGGCCTGGCTTTGGGAAAAGTACGGCCTG
AGGCCCGACCAGTGGGCCGACTACCGGGCCCTGACCGGGGACGAGTCCGACAACCTTCCCGGGGTCAAGGGCATCGGGGAGAAGACG
GCGAGGAAGCTTCTGGAGGAGTGGGGGAGCCTGGAAGCCCTCCTCAAGAACCTGGACCGGCTGAAGCCCGCCATCCGGGAGAAGATC
CTGGCCCACATGGACGATCTGAAGCTCTCCTGGGACCTGGCCAAGGTGCGCACCGACCTGCCCCTGGAGGTGGACTTCGCCAAAAGG
CGGGAGCCCGACCGGGAGAGGCTTAGGGCCTTTCTGGAGAGGCTTGAGTTTGGCAGCCTCCTCCACGAGTTCGGCCTTCTGGAAAGC
CCCAAGGCCCTGGAGGAGGCCCCCTGGCCCCCGCCGGAAGGGGCCTTCGTGGGCTTTGTGCTTTCCCGCAAGGAGCCCATGTGGGCC
GATCTTCTGGCCCTGGCCGCCGCCAGGGGGGGCCGGGTCCACCGGGCCCCCGAGCCTTATAAAGCCCTCAGGGACCTGAAGGAGGCG
CGGGGGCTTCTCGCCAAAGACCTGAGCGTTCTGGCCCTGAGGGAAGGCCTTGGCCTCCCGCCCGGCGACGACCCCATGCTCCTCGCC
TACCTCCTGGACCCTTCCAACACCACCCCCGAGGGGGTGGCCCGGCGCTACGGCGGGGAGTGGACGGAGGAGGCGGGGGAGCGGGCC
GCCCTTTCCGAGAGGCTCTTCGCCAACCTGTGGGGGAGGCTTGAGGGGGAGGAGAGGCTCCTTTGGCTTTACCGGGAGGTGGAGAGG
CCCCTTTCCGCTGTCCTGGCCCACATGGAGGCCACGGGGGTGCGCCTGGACGTGGCCTATCTCAGGGCCTTGTCCCTGGAGGTGGCC
GAGGAGATCGCCCGCCTCGAGGCCGAGGTCTTCCGCCTGGCCGGCCACCCCTTCAACCTCAACTCCCGGGACCAGCTGGAAAGGGTC
CTCTTTGACGAGCTAGGGCTTCCCGCCATCGGCAAGACGGAGAAGACCGGCAAGCGCTCCACCAGCGCCGCCGTCCTGGAGGCCCTC
CGCGAGGCCCACCCCATCGTGGAGAAGATCCTGCAGTACCGGGAGCTCACCAAGCTGAAGAGCACCTACATTGACCCCTTGCCGGAC
CTCATCCACCCCAGGACGGGCCGCCTCCACACCCGCTTCAACCAGACGGCCACGGCCACGGGCAGGCTAAGTAGCTCCGATCCCAAC
CTCCAGAACATCCCCGTCCGCACCCCGCTTGGGCAGAGGATCCGCCGGGCCTTCATCGCCGAGGAGGGGTGGCTATTGGTGGCCCTG
GACTATAGCCAGATAGAGCTCAGGGTGCTGGCCCACCTCTCCGGCGACGAGAACCTGATCCGGGTCTTCCAGGAGGGGCGGGACATC
CACACGGAGACCGCCAGCTGGATGTTCGGCGTCCCCGGGAGGCCGTGGACCCCCTGATGCGCCGGGCGGCCAAGACCATCAACTTC
GGGGTCCTCTACGGCATGTCGGCCCACCGCCTCTCCCAGGAGCTAGCCATCCCTTACGAGGAGGCCCAGGCCTTCATTGAGCGCTAC
TTTCAGAGCTTCCCCAAGGTGCGGGCCTGGATTGAGAAGACCCTGGAGGAGGGCAGGAGGCGGGGGTACGTGGAGACCCTCTTCGGC
CGCCGCCGCTACGTGCCAGACCTAGAGGCCCGGGTGAAGAGCGTGCGGGCGGCGGCCGAGCGCATGGCCTTCAACATGCCCGTCCAG
GGCACCGCCGCCGACCTCATGAAGCTGGCTATGGTGAAGCTCTTCCCCAGGCTGGAGGAAATGGGGGCCAGGATGCTCCTTCAGGTC
CACGACGAGCTGGTCCTCGAGGCCCCAAAAGAGAGGGCGGAGGCCGTGGCCCGGCTGGCCAAGGAGGTCATGGAGGGGGTGTATCCC
CTGGCCGTGCCCCTGGAGGTGGAGGTGGGGATAGGGGAGGACTGGCTCTCCGCCAAGGAGTGA

Taq Exo⁻ + E742A amino acid sequence                SEQ ID NO: 18

MRGMLPLFEPKGRVLLVDGHHLAYRTFHALKGLTTSRGEPVQAVYGFAKSLLKALKEDGDAVIVVFDAKAPSFRHEAYGGYKAGRAP
TPEDFPRQLALIKELVDLLGLARLEVPGYAAADVLASLAKKAEKEGYEVRILTAAKALYQLLSDRIHVLHPEGYLITPAWLWEKYGL
RPDQWADYRALTGDESDNLPGVKGIGEKTARKLLEEWGSLEALLKNLDRLKPAIREKILAHMDDLKLSWDLAKVRTDLPLEVDFAKR
REPDRERLRAFLERLEFGSLLHEFGLLESPKALEEAPWPPPEGAFVGFVLSRKEPMWADLLALAAARGGRVHRAPEPYKALRDLKEA
RGLLAKDLSVLALREGLGLPPGDDPMLLAYLLDPSNTTPEGVARRYGGEWTEEAGERAALSERLFANLWGRLEGEERLLWLYREVER
PLSAVLAHMEATGVRLDVAYLRALSLEVAEEIARLEAEVFRLAGHPFNLNSRDQLERVLFDELGLPAIGKTEKTGKRSTSAAVLEAL
REAHPIVEKILQYRELTKLKSTYIDPLPDLIHPRTGRLHTRFNQTATATGRLSSSDPNLQNIPVRTPLGQRIRRAFIAEEGWLLVAL
DYSQIELRVLAHLSGDENLIRVFQEGRDIHTETASWMFGVPREAVDPLMRRAAKTINFGVLYGMSAHRLSQELAIPYEEAQAFIERY
FQSFPKVRAWIEKTLEEGRRRGYVETLFGRRRYVPDLEARVKSVRAAAERMAFNMPVQGTAADLMKLAMVKLFPRLEEMGARMLLQV
HDELVLEAPKERAEAVARLAKEVMEGVYPLAVPLEVEVGIEDWLSAKE

FIG. 10

Taq R651E nucleotide sequence          SEQ ID NO: 19

ATGAGGGGGATGCTGCCCCTCTTTGAGCCCAAGGGCCGGGTCCTCCTGGTGGACGGCCACCACCTGGCCTACCGCACCTTCCACGCC
CTGAAGGGCCTCACCACCAGCCGGGGGGAGCCGGTGCAGGCGGTCTACGGCTTCGCCAAGAGCCTCCTCAAGGCCCTCAAGGAGGAC
GGGGACGCGGTGATCGTGGTCTTTGACGCCAAGGCCCCCTCCTTCCGCCACGAGGCCTACGGGGGGTACAAGGCGGGCCGGGCCCCC
ACGCCGGAGGACTTTCCCCGGCAACTCGCCCTCATCAAGGAGCTGGTGGACCTCCTGGGGCTGGCGCGCCTCGAGGTCCCGGGCTAC
GAGGCGGACGACGTCCTGGCCAGCCTGGCCAAGAAGGCGGAAAAGGAGGGCTACGAGGTCCGCATCCTCACCGCCGACAAGGACCTT
TACCAGCTCCTTTCCGACCGCATCCACGTCCTCCACCCCGAGGGGTACCTCATCACCCCGGCCTGGCTTTGGGAAAAGTACGGCCTG
AGGCCCGACCAGTGGGCCGACTACCGGGCCCTGACCGGGGACGAGTCCGACAACCTTCCCGGGGTCAAGGGCATCGGGGAGAAGACG
GCGAGGAAGCTTCTGGAGGAGTGGGGGAGCCTGGAAGCCCTCCTCAAGAACCTGGACCGGCTGAAGCCCGCCATCCGGGAGAAGATC
CTGGCCCACATGGACGATCTGAAGCTCTCCTGGGACCTGGCCAAGGTGCGCACCGACCTGCCCCTGGAGGTGGACTTCGCCAAAAGG
CGGGAGCCCGACCGGGAGAGGCTTAGGGCCTTTCTGGAGAGGCTTGAGTTTGGCAGCCTCCTCCACGAGTTCGGCCTTCTGGAAAGC
CCCAAGGCCCTGGAGGAGGCCCCCTGGCCCCCGCCGGAAGGGGCCTTCGTGGGCTTTGTGCTTTCCCGCAAGGAGCCCATGTGGGCC
GATCTTCTGGCCCTGGCCGCCGCCAGGGGGGGCCGGGTCCACCGGGCCCCCGAGCCTTATAAAGCCCTCAGGGACCTGAAGGAGGCG
CGGGGGCTTCTCGCCAAAGACCTGAGCGTTCTGGCCCTGAGGGAAGGCCTTGGCCTCCCGCCCGGCGACGACCCCATGCTCCTCGCC
TACCTCCTGGACCCTTCCAACACCACCCCCGAGGGGGTGGCCCGGCGCTACGGCGGGGAGTGGACGGAGGAGGCGGGGGAGCGGGCC
GCCCTTTCCGAGAGGCTCTTCGCCAACCTGTGGGGGAGGCTTGAGGGGAGGAGAGGCTCCTTTGGCTTTACCGGGAGGTGGAGAGG
CCCCTTTCCGCTGTCCTGGCCCACATGGAGGCCACGGGGGTGCGCCTGGACGTGGCCTATCTCAGGGCCTTGTCCCTGGAGGTGGCC
GAGGAGATCGCCCGCCTCGAGGCCGAGGTCTTCCGCCTGGCCGGCCACCCCTTCAACCTCAACTCCCGGGACCAGCTGGAAAGGGTC
CTCTTTGACGAGCTAGGGCTTCCCGCCATCGGCAAGACGGAGAAGACCGGCAAGCGCTCCACCAGCGCCGCCGTCCTGGAGGCCCTC
CGCGAGGCCCACCCCATCGTGGAGAAGATCCTGCAGTACCGGGAGCTCACCAAGCTGAAGAGCACCTACATTGACCCCTTGCCGGAC
CTCATCCACCCCAGGACGGGCCGCCTCCACACCCGCTTCAACCAGACGGCCACGGCCACGGGCAGGCTAAGTAGCTCCGATCCCAAC
CTCCAGAACATCCCCGTCCGCACCCCGCTTGGGCAGAGGATCCGCCGGGCCTTCATCGCCGAGGAGGGGTGGCTATTGGTGGCCCTG
GACTATAGCCAGATAGAGCTCAGGGTGCTGGCCCACCTCTCCGGCGACGAGAACCTGATCCGGGTCTTCCAGGAGGGGCGGGACATC
CACACGGAGACCGCCAGCTGGATGTTCGGCGTCCCCGAGGAGGCCGTGGACCCCCTGATGCGCCGGGCGGCCAAGACCATCAACTTC
GGGGTCCTCTACGGCATGTCGGCCCACCGCCTCTCCCAGGAGCTAGCCATCCCTTACGAGGAGGCCCAGGCCTTCATTGAGCGCTAC
TTTCAGAGCTTCCCCAAGGTGCGGGCCTGGATTGAGAAGACCCTGGAGGAGGGCAGGAGGCGGGGGTACGTGGAGACCCTCTTCGGC
CGCCGCCGCTACGTGCCAGACCTAGAGGCCCGGGTGAAGAGCGTGCGGGAGGCGGCCGAGCGCATGGCCTTCAACATGCCCGTCCAG
GGCACCGCCGCCGACCTCATGAAGCTGGCTATGGTGAAGCTCTTCCCCAGGCTGGAGGAAATGGGGGCCAGGATGCTCCTTCAGGTC
CACGACGAGCTGGTCCTCGAGGCCCCAAAAGAGAGGGCGGAGGCCGTGGCCCGGCTGGCCAAGGAGGTCATGGAGGGGGTGTATCCC
CTGGCCGTGCCCCTGGAGGTGGAGGTGGGGATAGGGGAGGACTGGCTCTCCGCCAAGGAGTGA

Taq R651E amino acid sequence          SEQ ID NO: 20

MRGMLPLFEPKGRVLLVDGHHLAYRTFHALKGLTTSRGEPVQAVYGFAKSLLKALKEDGDAVIVVFDAKAPSFRHEAYGGYKAGRAP
TPEDFPRQLALIKELVDLLGLARLEVPGYEADDVLASLAKKAEKEGYEVRILTADKDLYQLLSDRIHVLHPEGYLITPAWLWEKYGL
RPDQWADYRALTGDESDNLPGVKGIGEKTARKLLEEWGSLEALLKNLDRLKPAIREKILAHMDDLKLSWDLAKVRTDLPLEVDFAKR
REPDRERLRAFLERLEFGSLLHEFGLLESPKALEEAPWPPPEGAFVGFVLSRKEPMWADLLALAAARGGRVHRAPEPYKALRDLKEA
RGLLAKDLSVLAREGLGLPPGDDPMLLAYLLDPSNTPEGVARRYGGEWTEEAGERAALSERLFANLWGRLEGEERLLWLYREVER
PLSAVLAHMEATGVRLDVAYLRALSLEVAEEIARLEAEVFRLAGHPFNLNSRDQLERVLFDELGLPAIGKTEKTGKRSTSAAVLEAL
REAHPIVEKILQYRELTKLKSTYIDPLPDLIHPRTGRLHTRFNQTATATGRLSSSDPNLQNIPVRTPLGQRIRRAFIAEEGWLLVAL
DYSQIELRVLAHLSGDENLIRVFQEGRDIHTETASWMFGVPEEAVDPLMRRAAKTINFGVLYGMSAHRLSQELAIPYEEAQAFIERY
FQSFPKVRAWIEKTLEEGRRRGYVETLFGRRRYVPDLEARVKSVREAAERMAFNMPVQGTAADLMKLAMVKLFPRLEEMGARMLLQV
HDELVLEAPKERAEAVARLAKEVMEGVYPLAVPLEVEVGIGEDWLSAKE

FIG. 11

Tth P653E nucleotide sequence  SEQ ID NO: 21

ATGGAGGCGATGCTTCCGCTCTTTGAACCCAAAGGCCGGGTCCTCCTGGTGGACGGCCACCACCTGGCCTACCGCACCTTCTTCGCC
CTGAAGGGCCTCACCACGAGCCGGGGCGAACCGGTGCAGGCGGTCTACGGCTTCGCCAAGAGCCTCCTCAAGGCCCTGAAGGAGGAC
GGGTACAAGGCCGTCTTCGTGGTCTTTGACGCCAAGGCCCCCTCCTTCCGCCACGAGGCCTACGAGGCCTACAAGGCGGGGAGGGCC
CCGACCCCCGAGGACTTCCCCCGGCAGCTCGCCCTCATCAAGGAGCTGGTGGACCTCCTGGGGTTTACCCGCCTCGAGGTCCCCGGC
TACGAGGCGGACGACGTTCTCGCCACCCTGGCCAAGAAGGCGGAAAAGGAGGGGTACGAGGTGCGCATCCTCACCGCCGACCGCGAC
CTCTACCAACTCGTCTCCGACCGCGTCGCCGTCCTCCACCCCGAGGGCCACCTCATCACCCCGGAGTGGCTTTGGGAGAAGTACGGC
CTCAGGCCGGAGCAGTGGGTGGACTTCCGCGCCCTCGTGGGGGACCCCTCCGACAACCTCCCCGGGGTCAAGGGCATCGGGGAGAAG
ACCGCCCTCAAGCTCCTCAAGGAGTGGGGAAGCCTGGAAAACCTCCTCAAGAACCTGGACCGGGTAAAGCCAGAAAACGTCCGGGAG
AAGATCAAGGCCCACCTGGAAGACCTCAGGCTCTCCTTGGAGCTCTCCCGGGTGCGCACCGACCTCCCCCTGGAGGTGGACCTCGCC
CAGGGGCGGGAGCCCGACCGGGAGGGGCTTAGGGCCTTCCTGGAGAGGCTGGAGTTCGGCAGCCTCCTCCACGAGTTCGGCCTCCTG
GAGGCCCCCGCCCCCCTGGAGGAGGCCCCCTGGCCCCCGCCGGAAGGGGCCTTCGTGGGCTTCGTCCTCTCCCGCCCCGAGCCCATG
TGGGCGGAGCTTAAAGCCCTGGCCGCCTGCAGGGACGGCCGGGTGCACCGGGCAGCAGACCCCTTGGCGGGGCTAAAGGACCTCAAG
GAGGTCCGGGGCCTCCTCGCCAAGGACCTCGCCGTCTTGGCCTCGAGGGAGGGGCTAGACCTCGTGCCCGGGGACGACCCCATGCTC
CTCGCCTACCTCCTGGACCCCTCCAACACCACCCCCGAGGGGGTGGCGCGGCGCTACGGGGGGGAGTGGACGGAGGACGCCGCCCAC
CGGGCCCTCCTCTCGGAGAGGCTCCATCGGAACCTCCTTAAGCGCCTCGAGGGGGAGGAGAAGCTCCTTTGGCTCTACCACGAGGTG
GAAAAGCCCCTCTCCCGGGTCCTGGCCCACATGGAGGCCACCGGGGTACGGCGGGACGTGGCCTACCTTCAGGCCCTTTCCCTGGAG
CTTGCGGAGGAGATCCGCCGCCTCGAGGAGGAGGTCTTCCGCTTGGCGGGCCACCCCTTCAACCTCAACTCCCGGGACCAGCTGGAA
AGGGTGCTCTTTGACGAGCTTAGGCTTCCCGCCTTGGGGAAGACGCAAAGACAGGCAAGCGCTCCACCAGCGCCGCGGTGCTGGAG
GCCCTACGGGAGGCCCACCCCATCGTGGAGAAGATCCTCCAGCACCGGGAGCTCACCAAGCTCAAGAACACCTACGTGGACCCCCTC
CCAAGCCTCGTCCACCCGAGGACGGGCCGCCTCCACACCCGCTTCAACCAGACGGCCACGGCCACGGGGAGGCTTAGTAGCTCCGAC
CCCAACCTGCAGAACATCCCCGTCCGCACCCCCTTGGGCCAGAGGATCCGCCGGGCCTTCGTGGCCGAGGCGGGTTGGGCGTTGGTG
GCCCTGGACTATAGCCAGATAGAGCTCCGCGTCCTCGCCCACCTCTCCGGGGACGAAAACCTGATCAGGGTCTTCCAGGAGGGGAAG
GACATCCACACCCAGACCGCAAGCTGGATGTTCGGCGTCCCCGAGGAGGCCGTGGACCCCCTGATGCGCCGGGCGGCCAAGACGGTG
AACTTCGGCGTCCTCTACGGCATGTCCGCCCATAGGCTCTCCCAGGAGCTTGCCATCCCCTACGAGGAGGCGGTGGCCTTTATAGAG
CGCTACTTCCAAAGCTTCCCCAAGGTGCGGGCCTGGATAGAAAAGACCCTGGAGGAGGGGAGGAAGCGGGGCTACGTGGAAACCCTC
TTCGGAAGAAGGCGCTACGTGCCCGACCTCAACGCCCGGGTGAAGAGCGTCAGGGAGGCCGCGGAGCGCATGGCCTTCAACATGCCC
GTCCAGGGCACCGCCGCCGACCTCATGAAGCTCGCCATGGTGAAGCTCTTCCCCCGCCTCCGGGAGATGGGGGCCCGCATGCTCCTC
CAGGTCCACGACGAGCTCCTCCTGGAGGCCCCCCAAGCGCGGGCCGAGGAGGTGGCGGCTTTGGCCAAGGAGGCCATGGAGAAGGCC
TATCCCCTCGCCGTGCCCCTGGAGGTGGAGGTGGGGATGGGGGAGGACTGGCTTTCCGCCAAGGGTTAG

Tth P653E amino acid sequence  SEQ ID NO: 22

MEAMLPLFEPKGRVLLVDGHHLAYRTFFALKGLTTSRGEPVQAVYGFAKSLLKALKEDGYKAVFVVFDAKAPSFRHEAYEAYKAGRA
PTPEDFPRQLALIKELVDLLGFTRLEVPGYEADDVLATLAKKAEKEGYEVRILTADRDLYQLVSDRVAVLHPEGHLITPEWLWEKYG
LRPEQWVDFRALVGDPSDNLPGVKGIGEKTALKLLKEWGSLENLLKNLDRVKPENVREKIKAHLEDLRLSLELSRVRTDLPLEVDLA
QGREPDREGLRAFLERLEFGSLLHEFGLLEAPAPLEEAPWPPPEGAFVGFVLSRPEPMWAELKALAACRDGRVHRAADPLAGLKDLK
EVRGLLAKDLAVLASREGLDLVPGDDPMLLAYLLDPSNTTPEGVARRYGGEWTEDAAHRALLSERLHRNLLKRLEGEEKLLWLYHEV
EKPLSRVLAHMEATGVRRDVAYLQALSLELAEEIRRLEEEVFRLAGHPFNLNSRDQLERVLFDELRLPALGKTQKTGKRSTSAAVLE
ALREAHPIVEKILQHRELTKLKNTYVDPLPSLVHPRTGRLHTRFNQTATATGRLSSSDPNLQNIPVRTPLGQRIRRAFVAEAGWALV
ALDYSQIELRVLAHLSGDENLIRVFQEGKDIHTQTASWMFGVPEEAVDPLMRRAAKTVNFGVLYGMSAHRLSQELAIPYEEAVAFIE
RYFQSFPKVRAWIEKTLEEGRKRGYVETLFGRRRYVPDLNARVKSVREAAERMAFNMPVQGTAADLMKLAMVKLFPRLREMGARMLL
QVHDELLLEAPQARAEEVAALAKEAMEKAYPLAVPLEVEVGMGEDWLSAKG

SEQUENCE LISTING

<160> NUMBER OF SEQ ID NOS: 29

<210> SEQ ID NO 1
<211> LENGTH: 45
<212> TYPE: DNA
<213> ORGANISM: Artificial sequence
<220> FEATURE:
<223> OTHER INFORMATION: Taq117119A-F primer

<400> SEQUENCE: 1
ctcgaggtcc cgggctacgc ggcggccgac gtcctggcca gcctg          45

<210> SEQ ID NO 2
<211> LENGTH: 45
<212> TYPE: DNA
<213> ORGANISM: Artificial sequence
<220> FEATURE:
<223> OTHER INFORMATION: Taq117119A-R primer

<400> SEQUENCE: 2
caggctggcc aggacgtcgg ccgccgcgta gcccgggacc tcgag          45

<210> SEQ ID NO 3
<211> LENGTH: 45
<212> TYPE: DNA
<213> ORGANISM: Artificial sequence
<220> FEATURE:
<223> OTHER INFORMATION: Taq142144A-F primer

<400> SEQUENCE: 3
gtccgcatcc tcaccgccgc caaagccctt taccagctcc tttcc          45

<210> SEQ ID NO 4
<211> LENGTH: 45
<212> TYPE: DNA
<213> ORGANISM: Artificial sequence
<220> FEATURE:
<223> OTHER INFORMATION: Taq142144A-R primer

<400> SEQUENCE: 4
ggaaaggagc tggtaaaggg ctttggcggc ggtgaggatg cggac          45

<210> SEQ ID NO 5
<211> LENGTH: 33
<212> TYPE: DNA
<213> ORGANISM: Artificial Sequence
<220> FEATURE:
<223> OTHER INFORMATION: E742A-F primer

<400> SEQUENCE: 5
gtgaagagcg tgcgggcggc ggccgagcgc atg          33

<210> SEQ ID NO 6
<211> LENGTH: 33
<212> TYPE: DNA
<213> ORGANISM: Artificial Sequence
<220> FEATURE:
<223> OTHER INFORMATION: E742A-R primer

<400> SEQUENCE: 6
catgcgctcg gccgccgccc gcacgctctt cac          33

<210> SEQ ID NO 7
<211> LENGTH: 30
<212> TYPE: DNA
<213> ORGANISM: Artificial Sequence

```
<220> FEATURE:
<223> OTHER INFORMATION: R651E-F primer

<400> SEQUENCE: 7
atgttcggcg tccccgagga ggccgtggac                                    30

<210> SEQ ID NO 8
<211> LENGTH: 30
<212> TYPE: DNA
<213> ORGANISM: Artificial Sequence
<220> FEATURE:
<223> OTHER INFORMATION: R651E-R primer

<400> SEQUENCE: 8
gtccacggcc tcctcgggga cgccgaacat                                    30

<210> SEQ ID NO 9
<211> LENGTH: 30
<212> TYPE: DNA
<213> ORGANISM: Artificial Sequence
<220> FEATURE:
<223> OTHER INFORMATION: P653E-F primer

<400> SEQUENCE: 9
atgttcggcg tccccgagga ggccgtggac                                    30

<210> SEQ ID NO 10
<211> LENGTH: 30
<212> TYPE: DNA
<213> ORGANISM: Artificial Sequence
<220> FEATURE:
<223> OTHER INFORMATION: P653E-R primer

<400> SEQUENCE: 10
gtccacggcc tcctcgggga cgccgaacat                                    30

<210> SEQ ID NO 11
<211> LENGTH: 2499
<212> TYPE: DNA
<213> ORGANISM: Thermus aquaticus
<220> FEATURE:
<221> NAME/KEY: CDS
<222> LOCATION: (1)..(2499)

<400> SEQUENCE: 11 atg agg ggg atg ctg ccc ctc ttt gag ccc aag ggc cgg gtc ctc ctg      48
Met Arg Gly Met Leu Pro Leu Phe Glu Pro Lys Gly Arg Val Leu Leu
1               5                   10                  15 gtg gac ggc cac cac ctg gcc tac cgc acc ttc cac gcc ctg aag ggc      96
Val Asp Gly His His Leu Ala Tyr Arg Thr Phe His Ala Leu Lys Gly
                20                  25                  30 ctc acc acc agc cgg ggg gag ccg gtg cag gcg gtc tac ggc ttc gcc     144
Leu Thr Thr Ser Arg Gly Glu Pro Val Gln Ala Val Tyr Gly Phe Ala
            35                  40                  45 aag agc ctc ctc aag gcc ctc aag gag gac ggg gac gcg gtg atc gtg     192
Lys Ser Leu Leu Lys Ala Leu Lys Glu Asp Gly Asp Ala Val Ile Val
        50                  55                  60 gtc ttt gac gcc aag gcc ccc tcc ttc cgc cac gag gcc tac ggg ggg     240
Val Phe Asp Ala Lys Ala Pro Ser Phe Arg His Glu Ala Tyr Gly Gly
65                  70                  75                  80 tac aag gcg ggc cgg gcc ccc acg ccg gag gac ttt ccc cgg caa ctc     288
Tyr Lys Ala Gly Arg Ala Pro Thr Pro Glu Asp Phe Pro Arg Gln Leu
                85                  90                  95
```

-continued

```
gcc ctc atc aag gag ctg gtg gac ctc ctg ggg ctg gcg cgc ctc gag        336
Ala Leu Ile Lys Glu Leu Val Asp Leu Leu Gly Leu Ala Arg Leu Glu
        100                 105                 110 gtc ccg ggc tac gag gcg gac gac gtc ctg gcc agc ctg gcc aag aag        384
Val Pro Gly Tyr Glu Ala Asp Asp Val Leu Ala Ser Leu Ala Lys Lys
        115                 120                 125 gcg gaa aag gag ggc tac gag gtc cgc atc ctc acc gcc gac aaa gac        432
Ala Glu Lys Glu Gly Tyr Glu Val Arg Ile Leu Thr Ala Asp Lys Asp
        130                 135                 140 ctt tac cag ctc ctt tcc gac cgc atc cac gtc ctc cac ccc gag ggg        480
Leu Tyr Gln Leu Leu Ser Asp Arg Ile His Val Leu His Pro Glu Gly
145                 150                 155                 160 tac ctc atc acc ccg gcc tgg ctt tgg gaa aag tac ggc ctg agg ccc        528
Tyr Leu Ile Thr Pro Ala Trp Leu Trp Glu Lys Tyr Gly Leu Arg Pro
                165                 170                 175 gac cag tgg gcc gac tac cgg gcc ctg acc ggg gac gag tcc gac aac        576
Asp Gln Trp Ala Asp Tyr Arg Ala Leu Thr Gly Asp Glu Ser Asp Asn
            180                 185                 190 ctt ccc ggg gtc aag ggc atc ggg gag aag acg gcg agg aag ctt ctg        624
Leu Pro Gly Val Lys Gly Ile Gly Glu Lys Thr Ala Arg Lys Leu Leu
        195                 200                 205 gag gag tgg ggg agc ctg gaa gcc ctc ctc aag aac ctg gac cgg ctg        672
Glu Glu Trp Gly Ser Leu Glu Ala Leu Leu Lys Asn Leu Asp Arg Leu
210                 215                 220 aag ccc gcc atc cgg gag aag atc ctg gcc cac atg gac gat ctg aag        720
Lys Pro Ala Ile Arg Glu Lys Ile Leu Ala His Met Asp Asp Leu Lys
225                 230                 235                 240 ctc tcc tgg gac ctg gcc aag gtg cgc acc gac ctg ccc ctg gag gtg        768
Leu Ser Trp Asp Leu Ala Lys Val Arg Thr Asp Leu Pro Leu Glu Val
                245                 250                 255 gac ttc gcc aaa agg cgg gag ccc gac cgg gag agg ctt agg gcc ttt        816
Asp Phe Ala Lys Arg Arg Glu Pro Asp Arg Glu Arg Leu Arg Ala Phe
            260                 265                 270 ctg gag agg ctt gag ttt ggc agc ctc ctc cac gag ttc ggc ctt ctg        864
Leu Glu Arg Leu Glu Phe Gly Ser Leu Leu His Glu Phe Gly Leu Leu
        275                 280                 285 gaa agc ccc aag gcc ctg gag gag gcc ccc tgg ccc ccg ccg gaa ggg        912
Glu Ser Pro Lys Ala Leu Glu Glu Ala Pro Trp Pro Pro Pro Glu Gly
        290                 295                 300 gcc ttc gtg ggc ttt gtg ctt tcc cgc aag gag ccc atg tgg gcc gat        960
Ala Phe Val Gly Phe Val Leu Ser Arg Lys Glu Pro Met Trp Ala Asp
305                 310                 315                 320 ctt ctg gcc ctg gcc gcc gcc agg ggg ggc cgg gtc cac cgg gcc ccc       1008
Leu Leu Ala Leu Ala Ala Ala Arg Gly Gly Arg Val His Arg Ala Pro
                325                 330                 335 gag cct tat aaa gcc ctc agg gac ctg aag gag gcg cgg ggg ctt ctc       1056
Glu Pro Tyr Lys Ala Leu Arg Asp Leu Lys Glu Ala Arg Gly Leu Leu
            340                 345                 350 gcc aaa gac ctg agc gtt ctg gcc ctg agg gaa ggc ctt ggc ctc ccg       1104
Ala Lys Asp Leu Ser Val Leu Ala Leu Arg Glu Gly Leu Gly Leu Pro
        355                 360                 365 ccc ggc gac gac ccc atg ctc ctc gcc tac ctc ctg gac cct tcc aac       1152
Pro Gly Asp Asp Pro Met Leu Leu Ala Tyr Leu Leu Asp Pro Ser Asn
        370                 375                 380 acc acc ccc gag ggg gtg gcc cgg cgc tac ggc ggg gag tgg acg gag       1200
Thr Thr Pro Glu Gly Val Ala Arg Arg Tyr Gly Gly Glu Trp Thr Glu
385                 390                 395                 400 gag gcg ggg gag cgg gcc gcc ctt tcc gag agg ctc ttc gcc aac ctg       1248
Glu Ala Gly Glu Arg Ala Ala Leu Ser Glu Arg Leu Phe Ala Asn Leu
                405                 410                 415
```

```
tgg ggg agg ctt gag ggg gag gag agg ctc ctt tgg ctt tac cgg gag    1296
Trp Gly Arg Leu Glu Gly Glu Glu Arg Leu Leu Trp Leu Tyr Arg Glu
            420                 425                 430 gtg gag agg ccc ctt tcc gct gtc ctg gcc cac atg gag gcc acg ggg    1344
Val Glu Arg Pro Leu Ser Ala Val Leu Ala His Met Glu Ala Thr Gly
        435                 440                 445 gtg cgc ctg gac gtg gcc tat ctc agg gcc ttg tcc ctg gag gtg gcc    1392
Val Arg Leu Asp Val Ala Tyr Leu Arg Ala Leu Ser Leu Glu Val Ala
    450                 455                 460 gag gag atc gcc cgc ctc gag gcc gag gtc ttc cgc ctg gcc ggc cac    1440
Glu Glu Ile Ala Arg Leu Glu Ala Glu Val Phe Arg Leu Ala Gly His
465                 470                 475                 480 ccc ttc aac ctc aac tcc cgg gac cag ctg gaa agg gtc ctc ttt gac    1488
Pro Phe Asn Leu Asn Ser Arg Asp Gln Leu Glu Arg Val Leu Phe Asp
                485                 490                 495 gag cta ggg ctt ccc gcc atc ggc aag acg gag aag acc ggc aag cgc    1536
Glu Leu Gly Leu Pro Ala Ile Gly Lys Thr Glu Lys Thr Gly Lys Arg
            500                 505                 510 tcc acc agc gcc gcc gtc ctg gag gcc ctc cgc gag gcc cac ccc atc    1584
Ser Thr Ser Ala Ala Val Leu Glu Ala Leu Arg Glu Ala His Pro Ile
        515                 520                 525 gtg gag aag atc ctg cag tac cgg gag ctc acc aag ctg aag agc acc    1632
Val Glu Lys Ile Leu Gln Tyr Arg Glu Leu Thr Lys Leu Lys Ser Thr
    530                 535                 540 tac att gac ccc ttg ccg gac ctc atc cac ccc agg acg ggc cgc ctc    1680
Tyr Ile Asp Pro Leu Pro Asp Leu Ile His Pro Arg Thr Gly Arg Leu
545                 550                 555                 560 cac acc cgc ttc aac cag acg gcc acg gcc acg ggc agg cta agt agc    1728
His Thr Arg Phe Asn Gln Thr Ala Thr Ala Thr Gly Arg Leu Ser Ser
                565                 570                 575 tcc gat ccc aac ctc cag aac atc ccc gtc cgc acc ccg ctt ggg cag    1776
Ser Asp Pro Asn Leu Gln Asn Ile Pro Val Arg Thr Pro Leu Gly Gln
            580                 585                 590 agg atc cgc cgg gcc ttc atc gcc gag gag ggg tgg cta ttg gtg gcc    1824
Arg Ile Arg Arg Ala Phe Ile Ala Glu Glu Gly Trp Leu Leu Val Ala
        595                 600                 605 ctg gac tat agc cag ata gag ctc agg gtg ctg gcc cac ctc tcc ggc    1872
Leu Asp Tyr Ser Gln Ile Glu Leu Arg Val Leu Ala His Leu Ser Gly
    610                 615                 620 gac gag aac ctg atc cgg gtc ttc cag gag ggg cgg gac atc cac acg    1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc    1968
Glu Thr Ala Ser Trp Met Phe Gly Val Pro Arg Glu Ala Val Asp Pro
                645                 650                 655 ctg atg cgc cgg gcg gcc aag acc atc aac ttc ggg gtc ctc tac ggc    2016
Leu Met Arg Arg Ala Ala Lys Thr Ile Asn Phe Gly Val Leu Tyr Gly
            660                 665                 670 atg tcg gcc cac cgc ctc tcc cag gag cta gcc atc cct tac gag gag    2064
Met Ser Ala His Arg Leu Ser Gln Glu Leu Ala Ile Pro Tyr Glu Glu
        675                 680                 685 gcc cag gcc ttc att gag cgc tac ttt cag agc ttc ccc aag gtg cgg    2112
Ala Gln Ala Phe Ile Glu Arg Tyr Phe Gln Ser Phe Pro Lys Val Arg
    690                 695                 700 gcc tgg att gag aag acc ctg gag gag ggc agg agg cgg ggg tac gtg    2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg    2208
Glu Thr Leu Phe Gly Arg Arg Arg Tyr Val Pro Asp Leu Glu Ala Arg
```

```
                      725                 730                 735
gtg aag agc gtg cgg gag gcg gcc gag cgc atg gcc ttc aac atg ccc      2256
Val Lys Ser Val Arg Glu Ala Ala Glu Arg Met Ala Phe Asn Met Pro
            740                 745                 750 gtc cag ggc acc gcc gcc gac ctc atg aag ctg gct atg gtg aag ctc      2304
Val Gln Gly Thr Ala Ala Asp Leu Met Lys Leu Ala Met Val Lys Leu
        755                 760                 765 ttc ccc agg ctg gag gaa atg ggg gcc agg atg ctc ctt cag gtc cac      2352
Phe Pro Arg Leu Glu Glu Met Gly Ala Arg Met Leu Leu Gln Val His
    770                 775                 780 gac gag ctg gtc ctc gag gcc cca aaa gag agg gcg gag gcc gtg gcc      2400
Asp Glu Leu Val Leu Glu Ala Pro Lys Glu Arg Ala Glu Ala Val Ala
785                 790                 795                 800 cgg ctg gcc aag gag gtc atg gag ggg gtg tat ccc ctg gcc gtg ccc      2448
Arg Leu Ala Lys Glu Val Met Glu Gly Val Tyr Pro Leu Ala Val Pro
                805                 810                 815 ctg gag gtg gag gtg ggg ata ggg gag gac tgg ctc tcc gcc aag gag      2496
Leu Glu Val Glu Val Gly Ile Gly Glu Asp Trp Leu Ser Ala Lys Glu
            820                 825                 830 tga                                                                  2499

<210> SEQ ID NO 12
<211> LENGTH: 832
<212> TYPE: PRT
<213> ORGANISM: Thermus aquaticus

<400> SEQUENCE: 12

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
```

```
                225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Pro Lys Ala Leu Glu Glu Ala Pro Trp Pro Pro Glu Gly
            290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
                450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
```

```
Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 13
<211> LENGTH: 2505
<212> TYPE: DNA
<213> ORGANISM: Thermus thermophilus
<220> FEATURE:
<221> NAME/KEY: CDS
<222> LOCATION: (1)..(2505)

<400> SEQUENCE: 13 atg gag gcg atg ctt ccg ctc ttt gaa ccc aaa ggc cgg gtc ctc ctg      48
Met Glu Ala Met Leu Pro Leu Phe Glu Pro Lys Gly Arg Val Leu Leu
1               5                   10                  15 gtg gac ggc cac cac ctg gcc tac cgc acc ttc ttc gcc ctg aag ggc      96
Val Asp Gly His His Leu Ala Tyr Arg Thr Phe Phe Ala Leu Lys Gly
            20                  25                  30 ctc acc acg agc cgg ggc gaa ccg gtg cag gcg gtc tac ggc ttc gcc     144
Leu Thr Thr Ser Arg Gly Glu Pro Val Gln Ala Val Tyr Gly Phe Ala
        35                  40                  45 aag agc ctc ctc aag gcc ctg aag gag gac ggg tac aag gcc gtc ttc     192
Lys Ser Leu Leu Lys Ala Leu Lys Glu Asp Gly Tyr Lys Ala Val Phe
    50                  55                  60 gtg gtc ttt gac gcc aag gcc ccc tcc ttc cgc cac gag gcc tac gag     240
Val Val Phe Asp Ala Lys Ala Pro Ser Phe Arg His Glu Ala Tyr Glu
65                  70                  75                  80 gcc tac aag gcg ggg agg gcc ccg acc ccc gag gac ttc ccc cgg cag     288
Ala Tyr Lys Ala Gly Arg Ala Pro Thr Pro Glu Asp Phe Pro Arg Gln
                85                  90                  95 ctc gcc ctc atc aag gag ctg gtg gac ctc ctg ggg ttt acc cgc ctc     336
Leu Ala Leu Ile Lys Glu Leu Val Asp Leu Leu Gly Phe Thr Arg Leu
            100                 105                 110 gag gtc ccc ggc tac gag gcg gac gac gtt ctc gcc acc ctg gcc aag     384
Glu Val Pro Gly Tyr Glu Ala Asp Asp Val Leu Ala Thr Leu Ala Lys
        115                 120                 125 aag gcg gaa aag gag ggg tac gag gtg cgc atc ctc acc gcc gac cgc     432
Lys Ala Glu Lys Glu Gly Tyr Glu Val Arg Ile Leu Thr Ala Asp Arg
    130                 135                 140
```

|  |  |  |  |  |  |  |  |  |  |  |  |  |  |  |  |
|---|---|---|---|---|---|---|---|---|---|---|---|---|---|---|---|
| 130 | | | | | 135 | | | | | 140 | | | | | |

```
gac ctc tac caa ctc gtc tcc gac cgc gtc gcc gtc ctc cac ccc gag     480
Asp Leu Tyr Gln Leu Val Ser Asp Arg Val Ala Val Leu His Pro Glu
145                 150                 155                 160 ggc cac ctc atc acc ccg gag tgg ctt tgg gag aag tac ggc ctc agg     528
Gly His Leu Ile Thr Pro Glu Trp Leu Trp Glu Lys Tyr Gly Leu Arg
            165                 170                 175 ccg gag cag tgg gtg gac ttc cgc gcc ctc gtg ggg gac ccc tcc gac     576
Pro Glu Gln Trp Val Asp Phe Arg Ala Leu Val Gly Asp Pro Ser Asp
                180                 185                 190 aac ctc ccc ggg gtc aag ggc atc ggg gag aag acc gcc ctc aag ctc     624
Asn Leu Pro Gly Val Lys Gly Ile Gly Glu Lys Thr Ala Leu Lys Leu
            195                 200                 205 ctc aag gag tgg gga agc ctg gaa aac ctc ctc aag aac ctg gac cgg     672
Leu Lys Glu Trp Gly Ser Leu Glu Asn Leu Leu Lys Asn Leu Asp Arg
        210                 215                 220 gta aag cca gaa aac gtc cgg gag aag atc aag gcc cac ctg gaa gac     720
Val Lys Pro Glu Asn Val Arg Glu Lys Ile Lys Ala His Leu Glu Asp
225                 230                 235                 240 ctc agg ctc tcc ttg gag ctc tcc cgg gtg cgc acc gac ctc ccc ctg     768
Leu Arg Leu Ser Leu Glu Leu Ser Arg Val Arg Thr Asp Leu Pro Leu
            245                 250                 255 gag gtg gac ctc gcc cag ggg cgg gag ccc gac cgg gag ggg ctt agg     816
Glu Val Asp Leu Ala Gln Gly Arg Glu Pro Asp Arg Glu Gly Leu Arg
                260                 265                 270 gcc ttc ctg gag agg ctg gag ttc ggc agc ctc ctc cac gag ttc ggc     864
Ala Phe Leu Glu Arg Leu Glu Phe Gly Ser Leu Leu His Glu Phe Gly
            275                 280                 285 ctc ctg gag gcc ccc gcc ccc ctg gag gag gcc ccc tgg ccc ccg ccg     912
Leu Leu Glu Ala Pro Ala Pro Leu Glu Glu Ala Pro Trp Pro Pro Pro
        290                 295                 300 gaa ggg gcc ttc gtg ggc ttc gtc ctc tcc cgc ccc gag ccc atg tgg     960
Glu Gly Ala Phe Val Gly Phe Val Leu Ser Arg Pro Glu Pro Met Trp
305                 310                 315                 320 gcg gag ctt aaa gcc ctg gcc gcc tgc agg gac ggc cgg gtg cac cgg    1008
Ala Glu Leu Lys Ala Leu Ala Ala Cys Arg Asp Gly Arg Val His Arg
            325                 330                 335 gca gca gac ccc ttg gcg ggg cta aag gac ctc aag gag gtc cgg ggc    1056
Ala Ala Asp Pro Leu Ala Gly Leu Lys Asp Leu Lys Glu Val Arg Gly
                340                 345                 350 ctc ctc gcc aag gac ctc gcc gtc ttg gcc tcg agg gag ggg cta gac    1104
Leu Leu Ala Lys Asp Leu Ala Val Leu Ala Ser Arg Glu Gly Leu Asp
            355                 360                 365 ctc gtg ccc ggg gac gac ccc atg ctc ctc gcc tac ctc ctg gac ccc    1152
Leu Val Pro Gly Asp Asp Pro Met Leu Leu Ala Tyr Leu Leu Asp Pro
        370                 375                 380 tcc aac acc acc ccc gag ggg gtg gcg cgg cgc tac ggg ggg gag tgg    1200
Ser Asn Thr Thr Pro Glu Gly Val Ala Arg Arg Tyr Gly Gly Glu Trp
385                 390                 395                 400 acg gag gac gcc gcc cac cgg gcc ctc ctc tcg gag agg ctc cat cgg    1248
Thr Glu Asp Ala Ala His Arg Ala Leu Leu Ser Glu Arg Leu His Arg
            405                 410                 415 aac ctc ctt aag cgc ctc gag ggg gag gag aag ctc ctt tgg ctc tac    1296
Asn Leu Leu Lys Arg Leu Glu Gly Glu Glu Lys Leu Leu Trp Leu Tyr
        420                 425                 430 cac gag gtg gaa aag ccc ctc tcc cgg gtc ctg gcc cac atg gag gcc    1344
His Glu Val Glu Lys Pro Leu Ser Arg Val Leu Ala His Met Glu Ala
            435                 440                 445 acc ggg gta cgg cgg gac gtg gcc tac ctt cag gcc ctt tcc ctg gag    1392
Thr Gly Val Arg Arg Asp Val Ala Tyr Leu Gln Ala Leu Ser Leu Glu
```

```
                                                         -continued

Thr Gly Val Arg Arg Asp Val Ala Tyr Leu Gln Ala Leu Ser Leu Glu
    450                 455                 460 ctt gcg gag gag atc cgc cgc ctc gag gag gag gtc ttc cgc ttg gcg     1440
Leu Ala Glu Glu Ile Arg Arg Leu Glu Glu Glu Val Phe Arg Leu Ala
465                 470                 475                 480 ggc cac ccc ttc aac ctc aac tcc cgg gac cag ctg gaa agg gtg ctc     1488
Gly His Pro Phe Asn Leu Asn Ser Arg Asp Gln Leu Glu Arg Val Leu
                    485                 490                 495 ttt gac gag ctt agg ctt ccc gcc ttg ggg aag acg caa aag aca ggc     1536
Phe Asp Glu Leu Arg Leu Pro Ala Leu Gly Lys Thr Gln Lys Thr Gly
                500                 505                 510 aag cgc tcc acc agc gcc gcg gtg ctg gag gcc cta cgg gag gcc cac     1584
Lys Arg Ser Thr Ser Ala Ala Val Leu Glu Ala Leu Arg Glu Ala His
            515                 520                 525 ccc atc gtg gag aag atc ctc cag cac cgg gag ctc acc aag ctc aag     1632
Pro Ile Val Glu Lys Ile Leu Gln His Arg Glu Leu Thr Lys Leu Lys
        530                 535                 540 aac acc tac gtg gac ccc ctc cca agc ctc gtc cac ccg agg acg ggc     1680
Asn Thr Tyr Val Asp Pro Leu Pro Ser Leu Val His Pro Arg Thr Gly
545                 550                 555                 560 cgc ctc cac acc cgc ttc aac cag acg gcc acg gcc acg ggg agg ctt     1728
Arg Leu His Thr Arg Phe Asn Gln Thr Ala Thr Ala Thr Gly Arg Leu
                    565                 570                 575 agt agc tcc gac ccc aac ctg cag aac atc ccc gtc cgc acc ccc ttg     1776
Ser Ser Ser Asp Pro Asn Leu Gln Asn Ile Pro Val Arg Thr Pro Leu
                580                 585                 590 ggc cag agg atc cgc cgg gcc ttc gtg gcc gag gcg ggt tgg gcg ttg     1824
Gly Gln Arg Ile Arg Arg Ala Phe Val Ala Glu Ala Gly Trp Ala Leu
            595                 600                 605 gtg gcc ctg gac tat agc cag ata gag ctc cgc gtc ctc gcc cac ctc     1872
Val Ala Leu Asp Tyr Ser Gln Ile Glu Leu Arg Val Leu Ala His Leu
        610                 615                 620 tcc ggg gac gaa aac ctg atc agg gtc ttc cag gag ggg aag gac atc     1920
Ser Gly Asp Glu Asn Leu Ile Arg Val Phe Gln Glu Gly Lys Asp Ile
625                 630                 635                 640 cac acc cag acc gca agc tgg atg ttc ggc gtc ccc ccg gag gcc gtg     1968
His Thr Gln Thr Ala Ser Trp Met Phe Gly Val Pro Pro Glu Ala Val
                    645                 650                 655 gac ccc ctg atg cgc cgg gcg gcc aag acg gtg aac ttc ggc gtc ctc     2016
Asp Pro Leu Met Arg Arg Ala Ala Lys Thr Val Asn Phe Gly Val Leu
                660                 665                 670 tac ggc atg tcc gcc cat agg ctc tcc cag gag ctt gcc atc ccc tac     2064
Tyr Gly Met Ser Ala His Arg Leu Ser Gln Glu Leu Ala Ile Pro Tyr
            675                 680                 685 gag gag gcg gtg gcc ttt ata gag cgc tac ttc caa agc ttc ccc aag     2112
Glu Glu Ala Val Ala Phe Ile Glu Arg Tyr Phe Gln Ser Phe Pro Lys
        690                 695                 700 gtg cgg gcc tgg ata gaa aag acc ctg gag gag ggg agg aag cgg ggc     2160
Val Arg Ala Trp Ile Glu Lys Thr Leu Glu Glu Gly Arg Lys Arg Gly
705                 710                 715                 720 tac gtg gaa acc ctc ttc gga aga agg cgc tac gtg ccc gac ctc aac     2208
Tyr Val Glu Thr Leu Phe Gly Arg Arg Arg Tyr Val Pro Asp Leu Asn
                    725                 730                 735 gcc cgg gtg aag agc gtc agg gag gcc gcg gag cgc atg gcc ttc aac     2256
Ala Arg Val Lys Ser Val Arg Glu Ala Ala Glu Arg Met Ala Phe Asn
                740                 745                 750 atg ccc gtc cag ggc acc gcc gcc gac ctc atg aag ctc gcc atg gtg     2304
Met Pro Val Gln Gly Thr Ala Ala Asp Leu Met Lys Leu Ala Met Val
            755                 760                 765
```

```
aag ctc ttc ccc cgc ctc cgg gag atg ggg gcc cgc atg ctc ctc cag    2352
Lys Leu Phe Pro Arg Leu Arg Glu Met Gly Ala Arg Met Leu Leu Gln
    770             775                 780 gtc cac gac gag ctc ctc ctg gag gcc ccc caa gcg cgg gcc gag gag    2400
Val His Asp Glu Leu Leu Leu Glu Ala Pro Gln Ala Arg Ala Glu Glu
785             790                 795                 800 gtg gcg gct ttg gcc aag gag gcc atg gag aag gcc tat ccc ctc gcc    2448
Val Ala Ala Leu Ala Lys Glu Ala Met Glu Lys Ala Tyr Pro Leu Ala
                805                 810                 815 gtg ccc ctg gag gtg gag gtg ggg atg ggg gag gac tgg ctt tcc gcc    2496
Val Pro Leu Glu Val Glu Val Gly Met Gly Glu Asp Trp Leu Ser Ala
        820                 825                 830 aag ggt tag                                                        2505
Lys Gly

<210> SEQ ID NO 14
<211> LENGTH: 834
<212> TYPE: PRT
<213> ORGANISM: Thermus thermophilus

<400> SEQUENCE: 14

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
```

-continued

```
                275                 280                 285
Leu Leu Glu Ala Pro Ala Pro Leu Glu Glu Ala Pro Trp Pro Pro
    290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
                340                 345                 350
Leu Leu Ala Lys Asp Leu Ala Val Leu Ala Ser Arg Glu Gly Leu Asp
                355                 360                 365
Leu Val Pro Gly Asp Pro Met Leu Leu Ala Tyr Leu Leu Asp Pro
    370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Glu Gly Glu Glu Lys Leu Leu Trp Leu Tyr
                420                 425                 430
His Glu Val Glu Lys Pro Leu Ser Arg Val Leu Ala His Met Glu Ala
                435                 440                 445
Thr Gly Val Arg Arg Asp Val Ala Tyr Leu Gln Ala Leu Ser Leu Glu
                450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
                500                 505                 510
Lys Arg Ser Thr Ser Ala Ala Val Leu Glu Ala Leu Arg Glu Ala His
                515                 520                 525
Pro Ile Val Glu Lys Ile Leu Gln His Arg Glu Leu Thr Lys Leu Lys
    530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
                580                 585                 590
Gly Gln Arg Ile Arg Arg Ala Phe Val Ala Glu Ala Gly Trp Ala Leu
                595                 600                 605
Val Ala Leu Asp Tyr Ser Gln Ile Glu Leu Arg Val Leu Ala His Leu
                610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Phe Gly Val Leu
                660                 665                 670
Tyr Gly Met Ser Ala His Arg Leu Ser Gln Glu Leu Ala Ile Pro Tyr
                675                 680                 685
Glu Glu Ala Val Ala Phe Ile Glu Arg Tyr Phe Gln Ser Phe Pro Lys
    690                 695                 700
```

-continued

```
Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
            725                 730                 735

Ala Arg Val Lys Ser Val Arg Glu Ala Ala Glu Arg Met Ala Phe Asn
        740                 745                 750

Met Pro Val Gln Gly Thr Ala Ala Asp Leu Met Lys Leu Ala Met Val
    755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 15
<211> LENGTH: 2499
<212> TYPE: DNA
<213> ORGANISM: Artificial sequence
<220> FEATURE:
<223> OTHER INFORMATION: Taq Exo-
<220> FEATURE:
<221> NAME/KEY: CDS
<222> LOCATION: (1)..(2499)

<400> SEQUENCE: 15 atg agg ggg atg ctg ccc ctc ttt gag ccc aag ggc cgg gtc ctc ctg      48
Met Arg Gly Met Leu Pro Leu Phe Glu Pro Lys Gly Arg Val Leu Leu
1               5                   10                  15 gtg gac ggc cac cac ctg gcc tac cgc acc ttc cac gcc ctg aag ggc      96
Val Asp Gly His His Leu Ala Tyr Arg Thr Phe His Ala Leu Lys Gly
            20                  25                  30 ctc acc acc agc cgg ggg gag ccg gtg cag gcg gtc tac ggc ttc gcc     144
Leu Thr Thr Ser Arg Gly Glu Pro Val Gln Ala Val Tyr Gly Phe Ala
        35                  40                  45 aag agc ctc ctc aag gcc ctc aag gag gac ggg gac gcg gtg atc gtg     192
Lys Ser Leu Leu Lys Ala Leu Lys Glu Asp Gly Asp Ala Val Ile Val
    50                  55                  60 gtc ttt gac gcc aag gcc ccc tcc ttc cgc cac gag gcc tac ggg ggg     240
Val Phe Asp Ala Lys Ala Pro Ser Phe Arg His Glu Ala Tyr Gly Gly
65                  70                  75                  80 tac aag gcg ggc cgg gcc ccc acg ccg gag gac ttt ccc cgg caa ctc     288
Tyr Lys Ala Gly Arg Ala Pro Thr Pro Glu Asp Phe Pro Arg Gln Leu
                85                  90                  95 gcc ctc atc aag gag ctg gtg gac ctc ctg ggg ctg gcg cgc ctc gag     336
Ala Leu Ile Lys Glu Leu Val Asp Leu Leu Gly Leu Ala Arg Leu Glu
            100                 105                 110 gtc ccg ggc tac gcg gcg gcc gac gtc ctg gcc agc ctg gcc aag aag     384
Val Pro Gly Tyr Ala Ala Ala Asp Val Leu Ala Ser Leu Ala Lys Lys
        115                 120                 125 gcg gaa aag gag ggc tac gag gtc cgc atc ctc acc gcc gcc aaa gcc     432
Ala Glu Lys Glu Gly Tyr Glu Val Arg Ile Leu Thr Ala Ala Lys Ala
    130                 135                 140 ctt tac cag ctc ctt tcc gac cgc atc cac gtc ctc cac ccc gag ggg     480
Leu Tyr Gln Leu Leu Ser Asp Arg Ile His Val Leu His Pro Glu Gly
145                 150                 155                 160
```

-continued

| | |
|---|---|
| tac ctc atc acc ccg gcc tgg ctt tgg gaa aag tac ggc ctg agg ccc<br>Tyr Leu Ile Thr Pro Ala Trp Leu Trp Glu Lys Tyr Gly Leu Arg Pro<br>                165                    170                    175 | 528 |
| gac cag tgg gcc gac tac cgg gcc ctg acc ggg gac gag tcc gac aac<br>Asp Gln Trp Ala Asp Tyr Arg Ala Leu Thr Gly Asp Glu Ser Asp Asn<br>        180                    185                    190 | 576 |
| ctt ccc ggg gtc aag ggc atc ggg gag aag acg gcg agg aag ctt ctg<br>Leu Pro Gly Val Lys Gly Ile Gly Glu Lys Thr Ala Arg Lys Leu Leu<br>            195                    200                    205 | 624 |
| gag gag tgg ggg agc ctg gaa gcc ctc ctc aag aac ctg gac cgg ctg<br>Glu Glu Trp Gly Ser Leu Glu Ala Leu Leu Lys Asn Leu Asp Arg Leu<br>        210                    215                    220 | 672 |
| aag ccc gcc atc cgg gag aag atc ctg gcc cac atg gac gat ctg aag<br>Lys Pro Ala Ile Arg Glu Lys Ile Leu Ala His Met Asp Asp Leu Lys<br>225                    230                    235                    240 | 720 |
| ctc tcc tgg gac ctg gcc aag gtg cgc acc gac ctg ccc ctg gag gtg<br>Leu Ser Trp Asp Leu Ala Lys Val Arg Thr Asp Leu Pro Leu Glu Val<br>                245                    250                    255 | 768 |
| gac ttc gcc aaa agg cgg gag ccc gac cgg gag agg ctt agg gcc ttt<br>Asp Phe Ala Lys Arg Arg Glu Pro Asp Arg Glu Arg Leu Arg Ala Phe<br>        260                    265                    270 | 816 |
| ctg gag agg ctt gag ttt ggc agc ctc ctc cac gag ttc ggc ctt ctg<br>Leu Glu Arg Leu Glu Phe Gly Ser Leu Leu His Glu Phe Gly Leu Leu<br>            275                    280                    285 | 864 |
| gaa agc ccc aag gcc ctg gag gag gcc ccc tgg ccc ccg ccg gaa ggg<br>Glu Ser Pro Lys Ala Leu Glu Glu Ala Pro Trp Pro Pro Pro Glu Gly<br>        290                    295                    300 | 912 |
| gcc ttc gtg ggc ttt gtg ctt tcc cgc aag gag ccc atg tgg gcc gat<br>Ala Phe Val Gly Phe Val Leu Ser Arg Lys Glu Pro Met Trp Ala Asp<br>305                    310                    315                    320 | 960 |
| ctt ctg gcc ctg gcc gcc gcc agg ggg ggc cgg gtc cac cgg gcc ccc<br>Leu Leu Ala Leu Ala Ala Ala Arg Gly Gly Arg Val His Arg Ala Pro<br>                325                    330                    335 | 1008 |
| gag cct tat aaa gcc ctc agg gac ctg aag gag gcg cgg ggg ctt ctc<br>Glu Pro Tyr Lys Ala Leu Arg Asp Leu Lys Glu Ala Arg Gly Leu Leu<br>        340                    345                    350 | 1056 |
| gcc aaa gac ctg agc gtt ctg gcc ctg agg gaa ggc ttg gcc ctc ccg<br>Ala Lys Asp Leu Ser Val Leu Ala Leu Arg Glu Gly Leu Gly Leu Pro<br>            355                    360                    365 | 1104 |
| ccc ggc gac gac ccc atg ctc ctc gcc tac ctc ctg gac cct tcc aac<br>Pro Gly Asp Asp Pro Met Leu Leu Ala Tyr Leu Leu Asp Pro Ser Asn<br>        370                    375                    380 | 1152 |
| acc acc ccc gag ggg gtg gcc cgg cgc tac ggc ggg gag tgg acg gag<br>Thr Thr Pro Glu Gly Val Ala Arg Arg Tyr Gly Gly Glu Trp Thr Glu<br>385                    390                    395                    400 | 1200 |
| gag gcg ggg gag cgg gcc gcc ctt tcc gag agg ctc ttc gcc aac ctg<br>Glu Ala Gly Glu Arg Ala Ala Leu Ser Glu Arg Leu Phe Ala Asn Leu<br>                405                    410                    415 | 1248 |
| tgg ggg agg ctt gag ggg gag gag agg ctc ctt tgg ctt tac cgg gag<br>Trp Gly Arg Leu Glu Gly Glu Glu Arg Leu Leu Trp Leu Tyr Arg Glu<br>            420                    425                    430 | 1296 |
| gtg gag agg ccc ctt tcc gct gtc ctg gcc cac atg gag gcc acg ggg<br>Val Glu Arg Pro Leu Ser Ala Val Leu Ala His Met Glu Ala Thr Gly<br>        435                    440                    445 | 1344 |
| gtg cgc ctg gac gtg gcc tat ctc agg gcc ttg tcc ctg gag gtg gcc<br>Val Arg Leu Asp Val Ala Tyr Leu Arg Ala Leu Ser Leu Glu Val Ala<br>        450                    455                    460 | 1392 |
| gag gag atc gcc cgc ctc gag gcc gag gtc ttc cgc ctg gcc ggc cac<br>Glu Glu Ile Ala Arg Leu Glu Ala Glu Val Phe Arg Leu Ala Gly His | 1440 |

```
            465                 470                 475                 480
ccc ttc aac ctc aac tcc cgg gac cag ctg gaa agg gtc ctc ttt gac       1488
Pro Phe Asn Leu Asn Ser Arg Asp Gln Leu Glu Arg Val Leu Phe Asp
                        485                 490                 495 gag cta ggg ctt ccc gcc atc ggc aag acg gag aag acc ggc aag cgc       1536
Glu Leu Gly Leu Pro Ala Ile Gly Lys Thr Glu Lys Thr Gly Lys Arg
                500                 505                 510 tcc acc agc gcc gcc gtc ctg gag gcc ctc cgc gag gcc cac ccc atc       1584
Ser Thr Ser Ala Ala Val Leu Glu Ala Leu Arg Glu Ala His Pro Ile
            515                 520                 525 gtg gag aag atc ctg cag tac cgg gag ctc acc aag ctg aag agc acc       1632
Val Glu Lys Ile Leu Gln Tyr Arg Glu Leu Thr Lys Leu Lys Ser Thr
        530                 535                 540 tac att gac ccc ttg ccg gac ctc atc cac ccc agg acg ggc cgc ctc       1680
Tyr Ile Asp Pro Leu Pro Asp Leu Ile His Pro Arg Thr Gly Arg Leu
545                 550                 555                 560 cac acc cgc ttc aac cag acg gcc acg gcc acg ggc agg cta agt agc       1728
His Thr Arg Phe Asn Gln Thr Ala Thr Ala Thr Gly Arg Leu Ser Ser
                        565                 570                 575 tcc gat ccc aac ctc cag aac atc ccc gtc cgc acc ccg ctt ggg cag       1776
Ser Asp Pro Asn Leu Gln Asn Ile Pro Val Arg Thr Pro Leu Gly Gln
                580                 585                 590 agg atc cgc cgg gcc ttc atc gcc gag gag ggg tgg cta ttg gtg gcc       1824
Arg Ile Arg Arg Ala Phe Ile Ala Glu Glu Gly Trp Leu Leu Val Ala
            595                 600                 605 ctg gac tat agc cag ata gag ctc agg gtg ctg gcc cac ctc tcc ggc       1872
Leu Asp Tyr Ser Gln Ile Glu Leu Arg Val Leu Ala His Leu Ser Gly
        610                 615                 620 gac gag aac ctg atc cgg gtc ttc cag gag ggg cgg gac atc cac acg       1920
Asp Glu Asn Leu Ile Arg Val Phe Gln Glu Gly Arg Asp Ile His Thr
625                 630                 635                 640 gag acc gcc agc tgg atg ttc ggc gtc ccc cgg gag gcc gtg gac ccc       1968
Glu Thr Ala Ser Trp Met Phe Gly Val Pro Arg Glu Ala Val Asp Pro
                        645                 650                 655 ctg atg cgc cgg gcg gcc aag acc atc aac ttc ggg gtc ctc tac ggc       2016
Leu Met Arg Arg Ala Ala Lys Thr Ile Asn Phe Gly Val Leu Tyr Gly
                660                 665                 670 atg tcg gcc cac cgc ctc tcc cag gag cta gcc atc cct tac gag gag       2064
Met Ser Ala His Arg Leu Ser Gln Glu Leu Ala Ile Pro Tyr Glu Glu
            675                 680                 685 gcc cag gcc ttc att gag cgc tac ttt cag agc ttc ccc aag gtg cgg       2112
Ala Gln Ala Phe Ile Glu Arg Tyr Phe Gln Ser Phe Pro Lys Val Arg
        690                 695                 700 gcc tgg att gag aag acc ctg gag gag ggc agg agg cgg ggg tac gtg       2160
Ala Trp Ile Glu Lys Thr Leu Glu Glu Gly Arg Arg Arg Gly Tyr Val
705                 710                 715                 720 gag acc ctc ttc ggc cgc cgc cgc tac gtg cca gac cta gag gcc cgg       2208
Glu Thr Leu Phe Gly Arg Arg Arg Tyr Val Pro Asp Leu Glu Ala Arg
                        725                 730                 735 gtg aag agc gtg cgg gag gcg gcc gag cgc atg gcc ttc aac atg ccc       2256
Val Lys Ser Val Arg Glu Ala Ala Glu Arg Met Ala Phe Asn Met Pro
                740                 745                 750 gtc cag ggc acc gcc gcc gac ctc atg aag ctg gct atg gtg aag ctc       2304
Val Gln Gly Thr Ala Ala Asp Leu Met Lys Leu Ala Met Val Lys Leu
            755                 760                 765 ttc ccc agg ctg gag gaa atg ggg gcc agg atg ctc ctt cag gtc cac       2352
Phe Pro Arg Leu Glu Glu Met Gly Ala Arg Met Leu Leu Gln Val His
        770                 775                 780 gac gag ctg gtc ctc gag gcc cca aaa gag agg gcg gag gcc gtg gcc       2400
```

-continued

```
Asp Glu Leu Val Leu Glu Ala Pro Lys Glu Arg Ala Glu Ala Val Ala
785                 790                 795                 800 cgg ctg gcc aag gag gtc atg gag ggg gtg tat ccc ctg gcc gtg ccc     2448
Arg Leu Ala Lys Glu Val Met Glu Gly Val Tyr Pro Leu Ala Val Pro
                805                 810                 815 ctg gag gtg gag gtg ggg ata ggg gag gac tgg ctc tcc gcc aag gag     2496
Leu Glu Val Glu Val Gly Ile Gly Glu Asp Trp Leu Ser Ala Lys Glu
            820                 825                 830 tga                                                                  2499
```

<210> SEQ ID NO 16
<211> LENGTH: 832
<212> TYPE: PRT
<213> ORGANISM: Artificial sequence
<220> FEATURE:
<223> OTHER INFORMATION: Synthetic Construct

<400> SEQUENCE: 16

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Ala Ala Asp Val Leu Ala Ser Leu Ala Lys Lys
        115                 120                 125

Ala Glu Lys Glu Gly Tyr Glu Val Arg Ile Leu Thr Ala Ala Lys Ala
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300
```

```
Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Gly Tyr Val
705                 710                 715                 720
```

-continued

```
Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

```
<210> SEQ ID NO 17
<211> LENGTH: 2499
<212> TYPE: DNA
<213> ORGANISM: Artificial Sequence
<220> FEATURE:
<223> OTHER INFORMATION: Taq Exo- + E742A
<220> FEATURE:
<221> NAME/KEY: CDS
<222> LOCATION: (1)..(2499)

<400> SEQUENCE: 17
```

| | | |
|---|---|---|
| atg agg ggg atg ctg ccc ctc ttt gag ccc aag ggc cgg gtc ctc ctg<br>Met Arg Gly Met Leu Pro Leu Phe Glu Pro Lys Gly Arg Val Leu Leu<br>1               5                   10                  15 | 48 |
| gtg gac ggc cac cac ctg gcc tac cgc acc ttc cac gcc ctg aag ggc<br>Val Asp Gly His His Leu Ala Tyr Arg Thr Phe His Ala Leu Lys Gly<br>            20                  25                  30 | 96 |
| ctc acc acc agc cgg ggg gag ccg gtg cag gcg gtc tac ggc ttc gcc<br>Leu Thr Thr Ser Arg Gly Glu Pro Val Gln Ala Val Tyr Gly Phe Ala<br>        35                  40                  45 | 144 |
| aag agc ctc ctc aag gcc ctc aag gag gac ggg gac gcg gtg atc gtg<br>Lys Ser Leu Leu Lys Ala Leu Lys Glu Asp Gly Asp Ala Val Ile Val<br>    50                  55                  60 | 192 |
| gtc ttt gac gcc aag gcc ccc tcc ttc gcc cac gag gcc tac ggg ggg<br>Val Phe Asp Ala Lys Ala Pro Ser Phe Arg His Glu Ala Tyr Gly Gly<br>65                  70                  75                  80 | 240 |
| tac aag gcg ggc cgg gcc ccc acg ccg gag gac ttt ccc cgg caa ctc<br>Tyr Lys Ala Gly Arg Ala Pro Thr Pro Glu Asp Phe Pro Arg Gln Leu<br>                85                  90                  95 | 288 |
| gcc ctc atc aag gag ctg gtg gac ctc ctg ggg ctg gcg cgc ctc gag<br>Ala Leu Ile Lys Glu Leu Val Asp Leu Leu Gly Leu Ala Arg Leu Glu<br>            100                 105                 110 | 336 |
| gtc ccg ggc tac gcg gcg gcc gac gtc ctg gcc agc ctg gcc aag aag<br>Val Pro Gly Tyr Ala Ala Ala Asp Val Leu Ala Ser Leu Ala Lys Lys<br>        115                 120                 125 | 384 |
| gcg gaa aag gag ggc tac gag gtc cgc atc ctc acc gcc gcc aaa gcc<br>Ala Glu Lys Glu Gly Tyr Glu Val Arg Ile Leu Thr Ala Ala Lys Ala<br>    130                 135                 140 | 432 |
| ctt tac cag ctc ctt tcc gac cgc atc cac gtc ctc cac ccc gag ggg<br>Leu Tyr Gln Leu Leu Ser Asp Arg Ile His Val Leu His Pro Glu Gly<br>145                 150                 155                 160 | 480 |
| tac ctc atc acc ccg gcc tgg ctt tgg gaa aag tac ggc ctg agg ccc<br>Tyr Leu Ile Thr Pro Ala Trp Leu Trp Glu Lys Tyr Gly Leu Arg Pro<br>                165                 170                 175 | 528 |
| gac cag tgg gcc gac tac cgg gcc ctg acc ggg gac gag tcc gac aac<br>  | 576 |

```
                Asp Gln Trp Ala Asp Tyr Arg Ala Leu Thr Gly Asp Glu Ser Asp Asn
                            180                 185                 190 ctt ccc ggg gtc aag ggc atc ggg gag aag acg gcg agg aag ctt ctg                624
Leu Pro Gly Val Lys Gly Ile Gly Glu Lys Thr Ala Arg Lys Leu Leu
            195                 200                 205 gag gag tgg ggg agc ctg gaa gcc ctc ctc aag aac ctg gac cgg ctg                672
Glu Glu Trp Gly Ser Leu Glu Ala Leu Leu Lys Asn Leu Asp Arg Leu
        210                 215                 220 aag ccc gcc atc cgg gag aag atc ctg gcc cac atg gac gat ctg aag                720
Lys Pro Ala Ile Arg Glu Lys Ile Leu Ala His Met Asp Asp Leu Lys
225                 230                 235                 240 ctc tcc tgg gac ctg gcc aag gtg cgc acc gac ctg ccc ctg gag gtg                768
Leu Ser Trp Asp Leu Ala Lys Val Arg Thr Asp Leu Pro Leu Glu Val
            245                 250                 255 gac ttc gcc aaa agg cgg gag ccc gac cgg gag agg ctt agg gcc ttt                816
Asp Phe Ala Lys Arg Arg Glu Pro Asp Arg Glu Arg Leu Arg Ala Phe
        260                 265                 270 ctg gag agg ctt gag ttt ggc agc ctc ctc cac gag ttc ggc ctt ctg                864
Leu Glu Arg Leu Glu Phe Gly Ser Leu Leu His Glu Phe Gly Leu Leu
    275                 280                 285 gaa agc ccc aag gcc ctg gag gag gcc ccc tgg ccc ccg ccg gaa ggg                912
Glu Ser Pro Lys Ala Leu Glu Glu Ala Pro Trp Pro Pro Pro Glu Gly
290                 295                 300 gcc ttc gtg ggc ttt gtg ctt tcc cgc aag gag ccc atg tgg gcc gat                960
Ala Phe Val Gly Phe Val Leu Ser Arg Lys Glu Pro Met Trp Ala Asp
305                 310                 315                 320 ctt ctg gcc ctg gcc gcc gcc agg ggg ggc cgg gtc cac cgg gcc ccc               1008
Leu Leu Ala Leu Ala Ala Ala Arg Gly Gly Arg Val His Arg Ala Pro
            325                 330                 335 gag cct tat aaa gcc ctc agg gac ctg aag gag gcg cgg ggg ctt ctc               1056
Glu Pro Tyr Lys Ala Leu Arg Asp Leu Lys Glu Ala Arg Gly Leu Leu
        340                 345                 350 gcc aaa gac ctg agc gtt ctg gcc ctg agg gaa ggc ttg ggc ctc ccg               1104
Ala Lys Asp Leu Ser Val Leu Ala Leu Arg Glu Gly Leu Gly Leu Pro
    355                 360                 365 ccc ggc gac gac ccc atg ctc ctc gcc tac ctc ctg gac cct tcc aac               1152
Pro Gly Asp Asp Pro Met Leu Leu Ala Tyr Leu Leu Asp Pro Ser Asn
370                 375                 380 acc acc ccc gag ggg gtg gcc cgg cgc tac ggc ggg gag tgg acg gag               1200
Thr Thr Pro Glu Gly Val Ala Arg Arg Tyr Gly Gly Glu Trp Thr Glu
385                 390                 395                 400 gag gcg ggg gag cgg gcc gcc ctt tcc gag agg ctc ttc gcc aac ctg               1248
Glu Ala Gly Glu Arg Ala Ala Leu Ser Glu Arg Leu Phe Ala Asn Leu
            405                 410                 415 tgg ggg agg ctt gag ggg gag gag agg ctc ctt tgg ctt tac cgg gag               1296
Trp Gly Arg Leu Glu Gly Glu Glu Arg Leu Leu Trp Leu Tyr Arg Glu
        420                 425                 430 gtg gag agg ccc ctt tcc gct gtc ctg gcc cac atg gag gcc acg ggg               1344
Val Glu Arg Pro Leu Ser Ala Val Leu Ala His Met Glu Ala Thr Gly
    435                 440                 445 gtg cgc ctg gac gtg gcc tat ctc agg gcc ttg tcc ctg gag gtg gcc               1392
Val Arg Leu Asp Val Ala Tyr Leu Arg Ala Leu Ser Leu Glu Val Ala
450                 455                 460 gag gag atc gcc cgc ctc gag gcc gag gtc ttc cgc ctg gcc ggc cac               1440
Glu Glu Ile Ala Arg Leu Glu Ala Glu Val Phe Arg Leu Ala Gly His
465                 470                 475                 480 ccc ttc aac ctc aac tcc cgg gac cag ctg gaa agg gtc ctc ttt gac               1488
Pro Phe Asn Leu Asn Ser Arg Asp Gln Leu Glu Arg Val Leu Phe Asp
            485                 490                 495
```

-continued

| | | |
|---|---|---|
| gag cta ggg ctt ccc gcc atc ggc aag acg gag aag acc ggc aag cgc<br>Glu Leu Gly Leu Pro Ala Ile Gly Lys Thr Glu Lys Thr Gly Lys Arg<br>500 505 510 | 1536 |
| tcc acc agc gcc gcc gtc ctg gag gcc ctc cgc gag gcc cac ccc atc<br>Ser Thr Ser Ala Ala Val Leu Glu Ala Leu Arg Glu Ala His Pro Ile<br>515 520 525 | 1584 |
| gtg gag aag atc ctg cag tac cgg gag ctc acc aag ctg aag agc acc<br>Val Glu Lys Ile Leu Gln Tyr Arg Glu Leu Thr Lys Leu Lys Ser Thr<br>530 535 540 | 1632 |
| tac att gac ccc ttg ccg gac ctc atc cac ccc agg acg ggc cgc ctc<br>Tyr Ile Asp Pro Leu Pro Asp Leu Ile His Pro Arg Thr Gly Arg Leu<br>545 550 555 560 | 1680 |
| cac acc cgc ttc aac cag acg gcc acg gcc acg ggc agg cta agt agc<br>His Thr Arg Phe Asn Gln Thr Ala Thr Ala Thr Gly Arg Leu Ser Ser<br>565 570 575 | 1728 |
| tcc gat ccc aac ctc cag aac atc ccc gtc cgc acc ccg ctt ggg cag<br>Ser Asp Pro Asn Leu Gln Asn Ile Pro Val Arg Thr Pro Leu Gly Gln<br>580 585 590 | 1776 |
| agg atc cgc cgg gcc ttc atc gcc gag gag ggg tgg cta ttg gtg gcc<br>Arg Ile Arg Arg Ala Phe Ile Ala Glu Glu Gly Trp Leu Leu Val Ala<br>595 600 605 | 1824 |
| ctg gac tat agc cag ata gag ctc agg gtg ctg gcc cac ctc tcc ggc<br>Leu Asp Tyr Ser Gln Ile Glu Leu Arg Val Leu Ala His Leu Ser Gly<br>610 615 620 | 1872 |
| gac gag aac ctg atc cgg gtc ttc cag gag ggg cgg gac atc cac acg<br>Asp Glu Asn Leu Ile Arg Val Phe Gln Glu Gly Arg Asp Ile His Thr<br>625 630 635 640 | 1920 |
| gag acc gcc agc tgg atg ttc ggc gtc ccc cgg gag gcc gtg gac ccc<br>Glu Thr Ala Ser Trp Met Phe Gly Val Pro Arg Glu Ala Val Asp Pro<br>645 650 655 | 1968 |
| ctg atg cgc cgg gcg gcc aag acc atc aac ttc ggg gtc ctc tac ggc<br>Leu Met Arg Arg Ala Ala Lys Thr Ile Asn Phe Gly Val Leu Tyr Gly<br>660 665 670 | 2016 |
| atg tcg gcc cac cgc ctc tcc cag gag cta gcc atc cct tac gag gag<br>Met Ser Ala His Arg Leu Ser Gln Glu Leu Ala Ile Pro Tyr Glu Glu<br>675 680 685 | 2064 |
| gcc cag gcc ttc att gag cgc tac ttt cag agc ttc ccc aag gtg cgg<br>Ala Gln Ala Phe Ile Glu Arg Tyr Phe Gln Ser Phe Pro Lys Val Arg<br>690 695 700 | 2112 |
| gcc tgg att gag aag acc ctg gag gag ggc agg agg cgg ggg tac gtg<br>Ala Trp Ile Glu Lys Thr Leu Glu Glu Gly Arg Arg Arg Gly Tyr Val<br>705 710 715 720 | 2160 |
| gag acc ctc ttc ggc cgc cgc cgc tac gtg cca gac cta gag gcc cgg<br>Glu Thr Leu Phe Gly Arg Arg Arg Tyr Val Pro Asp Leu Glu Ala Arg<br>725 730 735 | 2208 |
| gtg aag agc gtg cgg gcg gcg gcc gag cgc atg gcc ttc aac atg ccc<br>Val Lys Ser Val Arg Ala Ala Ala Glu Arg Met Ala Phe Asn Met Pro<br>740 745 750 | 2256 |
| gtc cag ggc acc gcc gcc gac ctc atg aag ctg gct atg gtg aag ctc<br>Val Gln Gly Thr Ala Ala Asp Leu Met Lys Leu Ala Met Val Lys Leu<br>755 760 765 | 2304 |
| ttc ccc agg ctg gag gaa atg ggg gcc agg atg ctc ctt cag gtc cac<br>Phe Pro Arg Leu Glu Glu Met Gly Ala Arg Met Leu Leu Gln Val His<br>770 775 780 | 2352 |
| gac gag ctg gtc ctc gag gcc cca aaa gag agg gcg gag gcc gtg gcc<br>Asp Glu Leu Val Leu Glu Ala Pro Lys Glu Arg Ala Glu Ala Val Ala<br>785 790 795 800 | 2400 |
| cgg ctg gcc aag gag gtc atg gag ggg gtg tat ccc ctg gcc gtg ccc<br>Arg Leu Ala Lys Glu Val Met Glu Gly Val Tyr Pro Leu Ala Val Pro<br>805 810 815 | 2448 |

```
ctg gag gtg gag gtg ggg ata ggg gag gac tgg ctc tcc gcc aag gag    2496
Leu Glu Val Glu Val Gly Ile Gly Glu Asp Trp Leu Ser Ala Lys Glu
            820                 825                 830 tga                                                                 2499
```

<210> SEQ ID NO 18
<211> LENGTH: 832
<212> TYPE: PRT
<213> ORGANISM: Artificial Sequence
<220> FEATURE:
<223> OTHER INFORMATION: Synthetic Construct

<400> SEQUENCE: 18

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Ala Ala Ala Asp Val Leu Ala Ser Leu Ala Lys Lys
        115                 120                 125

Ala Glu Lys Glu Gly Tyr Glu Val Arg Ile Leu Thr Ala Ala Lys Ala
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335
```

```
Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Ala Ala Ala Glu Arg Met Ala Phe Asn Met Pro
            740                 745                 750
```

```
Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 19
<211> LENGTH: 2499
<212> TYPE: DNA
<213> ORGANISM: Artificial Sequence
<220> FEATURE:
<223> OTHER INFORMATION: Taq R651E
<220> FEATURE:
<221> NAME/KEY: CDS
<222> LOCATION: (1)..(2499)

<400> SEQUENCE: 19
```

| | | |
|---|---|---|
| atg agg ggg atg ctg ccc ctc ttt gag ccc aag ggc cgg gtc ctc ctg | | 48 |
| Met Arg Gly Met Leu Pro Leu Phe Glu Pro Lys Gly Arg Val Leu Leu | | |
| 1               5                   10                  15 | | |
| gtg gac ggc cac cac ctg gcc tac cgc acc ttc cac gcc ctg aag ggc | | 96 |
| Val Asp Gly His His Leu Ala Tyr Arg Thr Phe His Ala Leu Lys Gly | | |
|             20                  25                  30 | | |
| ctc acc acc agc cgg ggg gag ccg gtg cag gcg gtc tac ggc ttc gcc | | 144 |
| Leu Thr Thr Ser Arg Gly Glu Pro Val Gln Ala Val Tyr Gly Phe Ala | | |
|         35                  40                  45 | | |
| aag agc ctc ctc aag gcc ctc aag gag gac ggg gac gcg gtg atc gtg | | 192 |
| Lys Ser Leu Leu Lys Ala Leu Lys Glu Asp Gly Asp Ala Val Ile Val | | |
|     50                  55                  60 | | |
| gtc ttt gac gcc aag gcc ccc tcc ttc cgc cac gag gcc tac ggg ggg | | 240 |
| Val Phe Asp Ala Lys Ala Pro Ser Phe Arg His Glu Ala Tyr Gly Gly | | |
| 65                  70                  75                  80 | | |
| tac aag gcg ggc cgg gcc ccc acg ccg gag gac ttt ccc cgg caa ctc | | 288 |
| Tyr Lys Ala Gly Arg Ala Pro Thr Pro Glu Asp Phe Pro Arg Gln Leu | | |
|                 85                  90                  95 | | |
| gcc ctc atc aag gag ctg gtg gac ctc ctg ggg ctg gcg cgc ctc gag | | 336 |
| Ala Leu Ile Lys Glu Leu Val Asp Leu Leu Gly Leu Ala Arg Leu Glu | | |
|             100                 105                 110 | | |
| gtc ccg ggc tac gag gcg gac gac gtc ctg gcc agc ctg gcc aag aag | | 384 |
| Val Pro Gly Tyr Glu Ala Asp Asp Val Leu Ala Ser Leu Ala Lys Lys | | |
|         115                 120                 125 | | |
| gcg gaa aag gag ggc tac gag gtc cgc atc ctc acc gcc gac aaa gac | | 432 |
| Ala Glu Lys Glu Gly Tyr Glu Val Arg Ile Leu Thr Ala Asp Lys Asp | | |
|     130                 135                 140 | | |
| ctt tac cag ctc ctt tcc gac cgc atc cac gtc ctc cac ccc gag ggg | | 480 |
| Leu Tyr Gln Leu Leu Ser Asp Arg Ile His Val Leu His Pro Glu Gly | | |
| 145                 150                 155                 160 | | |
| tac ctc atc acc ccg gcc tgg ctt tgg gaa aag tac ggc ctg agg ccc | | 528 |
| Tyr Leu Ile Thr Pro Ala Trp Leu Trp Glu Lys Tyr Gly Leu Arg Pro | | |
|                 165                 170                 175 | | |
| gac cag tgg gcc gac tac cgg gcc ctg acc ggg gac gag tcc gac aac | | 576 |
| Asp Gln Trp Ala Asp Tyr Arg Ala Leu Thr Gly Asp Glu Ser Asp Asn | | |
|             180                 185                 190 | | |
| ctt ccc ggg gtc aag ggc atc ggg gag aag acg gcg agg aag ctt ctg | | 624 |
| Leu Pro Gly Val Lys Gly Ile Gly Glu Lys Thr Ala Arg Lys Leu Leu | | |
|         195                 200                 205 | | |

-continued

| | | |
|---|---|---|
| gag gag tgg ggg agc ctg gaa gcc ctc ctc aag aac ctg gac cgg ctg<br>Glu Glu Trp Gly Ser Leu Glu Ala Leu Leu Lys Asn Leu Asp Arg Leu<br>210                       215                       220 | | 672 |
| aag ccc gcc atc cgg gag aag atc ctg gcc cac atg gac gat ctg aag<br>Lys Pro Ala Ile Arg Glu Lys Ile Leu Ala His Met Asp Asp Leu Lys<br>225                    230                  235                  240 | | 720 |
| ctc tcc tgg gac ctg gcc aag gtg cgc acc gac ctg ccc ctg gag gtg<br>Leu Ser Trp Asp Leu Ala Lys Val Arg Thr Asp Leu Pro Leu Glu Val<br>                   245                  250                  255 | | 768 |
| gac ttc gcc aaa agg cgg gag ccc gac cgg gag agg ctt agg gcc ttt<br>Asp Phe Ala Lys Arg Arg Glu Pro Asp Arg Glu Arg Leu Arg Ala Phe<br>            260                  265                  270 | | 816 |
| ctg gag agg ctt gag ttt ggc agc ctc ctc cac gag ttc ggc ctt ctg<br>Leu Glu Arg Leu Glu Phe Gly Ser Leu Leu His Glu Phe Gly Leu Leu<br>275                       280                     285 | | 864 |
| gaa agc ccc aag gcc ctg gag gag gcc ccc tgg ccc ccg ccg gaa ggg<br>Glu Ser Pro Lys Ala Leu Glu Glu Ala Pro Trp Pro Pro Pro Glu Gly<br>290                       295                     300 | | 912 |
| gcc ttc gtg ggc ttt gtg ctt tcc cgc aag gag ccc atg tgg gcc gat<br>Ala Phe Val Gly Phe Val Leu Ser Arg Lys Glu Pro Met Trp Ala Asp<br>305                    310                  315                  320 | | 960 |
| ctt ctg gcc ctg gcc gcc gcc agg ggg ggc cgg gtc cac cgg gcc ccc<br>Leu Leu Ala Leu Ala Ala Ala Arg Gly Gly Arg Val His Arg Ala Pro<br>                   325                  330                  335 | | 1008 |
| gag cct tat aaa gcc ctc agg gac ctg aag gag gcg cgg ggg ctt ctc<br>Glu Pro Tyr Lys Ala Leu Arg Asp Leu Lys Glu Ala Arg Gly Leu Leu<br>            340                  345                  350 | | 1056 |
| gcc aaa gac ctg agc gtt ctg gcc ctg agg gaa ggc ctt ggc ctc ccg<br>Ala Lys Asp Leu Ser Val Leu Ala Leu Arg Glu Gly Leu Gly Leu Pro<br>355                       360                  365 | | 1104 |
| ccc ggc gac gac ccc atg ctc ctc gcc tac ctc ctg gac cct tcc aac<br>Pro Gly Asp Asp Pro Met Leu Leu Ala Tyr Leu Leu Asp Pro Ser Asn<br>            370                  375                  380 | | 1152 |
| acc acc ccc gag ggg gtg gcc cgg cgc tac ggc ggg gag tgg acg gag<br>Thr Thr Pro Glu Gly Val Ala Arg Arg Tyr Gly Gly Glu Trp Thr Glu<br>385                    390                  395                  400 | | 1200 |
| gag gcg ggg gag cgg gcc gcc ctt tcc gag agg ctc ttc gcc aac ctg<br>Glu Ala Gly Glu Arg Ala Ala Leu Ser Glu Arg Leu Phe Ala Asn Leu<br>                   405                  410                  415 | | 1248 |
| tgg ggg agg ctt gag ggg gag gag agg ctc ctt tgg ctt tac cgg gag<br>Trp Gly Arg Leu Glu Gly Glu Glu Arg Leu Leu Trp Leu Tyr Arg Glu<br>            420                  425                  430 | | 1296 |
| gtg gag agg ccc ctt tcc gct gtc ctg gcc cac atg gag gcc acg ggg<br>Val Glu Arg Pro Leu Ser Ala Val Leu Ala His Met Glu Ala Thr Gly<br>435                       440                     445 | | 1344 |
| gtg cgc ctg gac gtg gcc tat ctc agg gcc ttg tcc ctg gag gtg gcc<br>Val Arg Leu Asp Val Ala Tyr Leu Arg Ala Leu Ser Leu Glu Val Ala<br>450                       455                     460 | | 1392 |
| gag gag atc gcc cgc ctc gag gcc gag gtc ttc cgc ctg gcc ggc cac<br>Glu Glu Ile Ala Arg Leu Glu Ala Glu Val Phe Arg Leu Ala Gly His<br>465                    470                  475                  480 | | 1440 |
| ccc ttc aac ctc aac tcc cgg gac cag ctg gaa agg gtc ctc ttt gac<br>Pro Phe Asn Leu Asn Ser Arg Asp Gln Leu Glu Arg Val Leu Phe Asp<br>                   485                  490                  495 | | 1488 |
| gag cta ggg ctt ccc gcc atc ggc aag acg gag aag acc ggc aag cgc<br>Glu Leu Gly Leu Pro Ala Ile Gly Lys Thr Glu Lys Thr Gly Lys Arg<br>            500                  505                  510 | | 1536 |
| tcc acc agc gcc gcc gtc ctg gag gcc ctc cgc gag gcc cac ccc atc<br>Ser Thr Ser Ala Ala Val Leu Glu Ala Leu Arg Glu Ala His Pro Ile | | 1584 |

-continued

```
              515                 520                 525
gtg gag aag atc ctg cag tac cgg gag ctc acc aag ctg aag agc acc     1632
Val Glu Lys Ile Leu Gln Tyr Arg Glu Leu Thr Lys Leu Lys Ser Thr
    530                 535                 540 tac att gac ccc ttg ccg gac ctc atc cac ccc agg acg ggc cgc ctc     1680
Tyr Ile Asp Pro Leu Pro Asp Leu Ile His Pro Arg Thr Gly Arg Leu
545                 550                 555                 560 cac acc cgc ttc aac cag acg gcc acg gcc acg ggc agg cta agt agc     1728
His Thr Arg Phe Asn Gln Thr Ala Thr Ala Thr Gly Arg Leu Ser Ser
                565                 570                 575 tcc gat ccc aac ctc cag aac atc ccc gtc cgc acc ccg ctt ggg cag     1776
Ser Asp Pro Asn Leu Gln Asn Ile Pro Val Arg Thr Pro Leu Gly Gln
            580                 585                 590 agg atc cgc cgg gcc ttc atc gcc gag gag ggg tgg cta ttg gtg gcc     1824
Arg Ile Arg Arg Ala Phe Ile Ala Glu Glu Gly Trp Leu Leu Val Ala
        595                 600                 605 ctg gac tat agc cag ata gag ctc agg gtg ctg gcc cac ctc tcc ggc     1872
Leu Asp Tyr Ser Gln Ile Glu Leu Arg Val Leu Ala His Leu Ser Gly
    610                 615                 620 gac gag aac ctg atc cgg gtc ttc cag gag ggg cgg gac atc cac acg     1920
Asp Glu Asn Leu Ile Arg Val Phe Gln Glu Gly Arg Asp Ile His Thr
625                 630                 635                 640 gag acc gcc agc tgg atg ttc ggc gtc ccc gag gag gcc gtg gac ccc     1968
Glu Thr Ala Ser Trp Met Phe Gly Val Pro Glu Glu Ala Val Asp Pro
                645                 650                 655 ctg atg cgc cgg gcg gcc aag acc atc aac ttc ggg gtc ctc tac ggc     2016
Leu Met Arg Arg Ala Ala Lys Thr Ile Asn Phe Gly Val Leu Tyr Gly
            660                 665                 670 atg tcg gcc cac cgc ctc tcc cag gag cta gcc atc cct tac gag gag     2064
Met Ser Ala His Arg Leu Ser Gln Glu Leu Ala Ile Pro Tyr Glu Glu
        675                 680                 685 gcc cag gcc ttc att gag cgc tac ttt cag agc ttc ccc aag gtg cgg     2112
Ala Gln Ala Phe Ile Glu Arg Tyr Phe Gln Ser Phe Pro Lys Val Arg
    690                 695                 700 gcc tgg att gag aag acc ctg gag gag ggc agg agg cgg ggg tac gtg     2160
Ala Trp Ile Glu Lys Thr Leu Glu Glu Gly Arg Arg Arg Gly Tyr Val
705                 710                 715                 720 gag acc ctc ttc ggc cgc cgc tac gtg cca gac cta gag gcc cgg         2208
Glu Thr Leu Phe Gly Arg Arg Arg Tyr Val Pro Asp Leu Glu Ala Arg
                725                 730                 735 gtg aag agc gtg cgg gag gcg gcc gag cgc atg gcc ttc aac atg ccc     2256
Val Lys Ser Val Arg Glu Ala Ala Glu Arg Met Ala Phe Asn Met Pro
            740                 745                 750 gtc cag ggc acc gcc gcc gac ctc atg aag ctg gct atg gtg aag ctc     2304
Val Gln Gly Thr Ala Ala Asp Leu Met Lys Leu Ala Met Val Lys Leu
        755                 760                 765 ttc ccc agg ctg gag gaa atg ggg gcc agg atg ctc ctt cag gtc cac     2352
Phe Pro Arg Leu Glu Glu Met Gly Ala Arg Met Leu Leu Gln Val His
    770                 775                 780 gac gag ctg gtc ctc gag gcc cca aaa gag agg gcg gag gcc gtg gcc     2400
Asp Glu Leu Val Leu Glu Ala Pro Lys Glu Arg Ala Glu Ala Val Ala
785                 790                 795                 800 cgg ctg gcc aag gag gtc atg gag ggg gtg tat ccc ctg gcc gtg ccc     2448
Arg Leu Ala Lys Glu Val Met Glu Gly Val Tyr Pro Leu Ala Val Pro
                805                 810                 815 ctg gag gtg gag gtg ggg ata ggg gag gac tgg ctc tcc gcc aag gag     2496
Leu Glu Val Glu Val Gly Ile Gly Glu Asp Trp Leu Ser Ala Lys Glu
            820                 825                 830 tga                                                                 2499
```

<210> SEQ ID NO 20
<211> LENGTH: 832
<212> TYPE: PRT
<213> ORGANISM: Artificial Sequence
<220> FEATURE:
<223> OTHER INFORMATION: Synthetic Construct

<400> SEQUENCE: 20

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365
```

```
Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Glu Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
    770                 775                 780
```

```
Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 21
<211> LENGTH: 2505
<212> TYPE: DNA
<213> ORGANISM: Artificial Sequence
<220> FEATURE:
<223> OTHER INFORMATION: Tth P653E
<220> FEATURE:
<221> NAME/KEY: CDS
<222> LOCATION: (1)..(2505)

<400> SEQUENCE: 21 atg gag gcg atg ctt ccg ctc ttt gaa ccc aaa ggc cgg gtc ctc ctg    48
Met Glu Ala Met Leu Pro Leu Phe Glu Pro Lys Gly Arg Val Leu Leu
1               5                   10                  15 gtg gac ggc cac cac ctg gcc tac cgc acc ttc ttc gcc ctg aag ggc    96
Val Asp Gly His His Leu Ala Tyr Arg Thr Phe Phe Ala Leu Lys Gly
            20                  25                  30 ctc acc acg agc cgg ggc gaa ccg gtg cag gcg gtc tac ggc ttc gcc   144
Leu Thr Thr Ser Arg Gly Glu Pro Val Gln Ala Val Tyr Gly Phe Ala
        35                  40                  45 aag agc ctc ctc aag gcc ctg aag gag gac ggg tac aag gcc gtc ttc   192
Lys Ser Leu Leu Lys Ala Leu Lys Glu Asp Gly Tyr Lys Ala Val Phe
    50                  55                  60 gtg gtc ttt gac gcc aag gcc ccc tcc ttc cgc cac gag gcc tac gag   240
Val Val Phe Asp Ala Lys Ala Pro Ser Phe Arg His Glu Ala Tyr Glu
65                  70                  75                  80 gcc tac aag gcg ggg agg gcc ccg acc ccc gag gac ttc ccc cgg cag   288
Ala Tyr Lys Ala Gly Arg Ala Pro Thr Pro Glu Asp Phe Pro Arg Gln
                85                  90                  95 ctc gcc ctc atc aag gag ctg gtg gac ctc ctg ggg ttt acc cgc ctc   336
Leu Ala Leu Ile Lys Glu Leu Val Asp Leu Leu Gly Phe Thr Arg Leu
            100                 105                 110 gag gtc ccc ggc tac gag gcg gac gac gtt ctc gcc acc ctg gcc aag   384
Glu Val Pro Gly Tyr Glu Ala Asp Asp Val Leu Ala Thr Leu Ala Lys
        115                 120                 125 aag gcg gaa aag gag ggg tac gag gtg cgc atc ctc acc gcc gac cgc   432
Lys Ala Glu Lys Glu Gly Tyr Glu Val Arg Ile Leu Thr Ala Asp Arg
    130                 135                 140 gac ctc tac caa ctc gtc tcc gac cgc gtc gcc gtc ctc cac ccc gag   480
Asp Leu Tyr Gln Leu Val Ser Asp Arg Val Ala Val Leu His Pro Glu
145                 150                 155                 160 ggc cac ctc atc acc ccg gag tgg ctt tgg gag aag tac ggc ctc agg   528
Gly His Leu Ile Thr Pro Glu Trp Leu Trp Glu Lys Tyr Gly Leu Arg
                165                 170                 175 ccg gag cag tgg gtg gac ttc cgc gcc ctc gtg ggg gac ccc tcc gac   576
Pro Glu Gln Trp Val Asp Phe Arg Ala Leu Val Gly Asp Pro Ser Asp
            180                 185                 190 aac ctc ccc ggg gtc aag ggc atc ggg gag aag acc gcc ctc aag ctc   624
Asn Leu Pro Gly Val Lys Gly Ile Gly Glu Lys Thr Ala Leu Lys Leu
        195                 200                 205 ctc aag gag tgg gga agc ctg gaa aac ctc ctc aag aac ctg gac cgg   672
Leu Lys Glu Trp Gly Ser Leu Glu Asn Leu Leu Lys Asn Leu Asp Arg
    210                 215                 220 gta aag cca gaa aac gtc cgg gag aag atc aag gcc cac ctg gaa gac   720
```

| | | | | | | | | | | | | | | |
|---|---|---|---|---|---|---|---|---|---|---|---|---|---|---|
| Val | Lys | Pro | Glu | Asn | Val | Arg | Glu | Lys | Ile | Lys | Ala | His | Leu | Glu | Asp |
| 225 | | | | 230 | | | | 235 | | | | 240 | | |

| ctc | agg | ctc | tcc | ttg | gag | ctc | tcc | cgg | gtg | cgc | acc | gac | ctc | ccc | ctg | 768 |
|---|---|---|---|---|---|---|---|---|---|---|---|---|---|---|---|---|
| Leu | Arg | Leu | Ser | Leu | Glu | Leu | Ser | Arg | Val | Arg | Thr | Asp | Leu | Pro | Leu | |
| | | | | 245 | | | | | 250 | | | | | 255 | | |

| gag | gtg | gac | ctc | gcc | cag | ggg | cgg | gag | ccc | gac | cgg | gag | ggg | ctt | agg | 816 |
|---|---|---|---|---|---|---|---|---|---|---|---|---|---|---|---|---|
| Glu | Val | Asp | Leu | Ala | Gln | Gly | Arg | Glu | Pro | Asp | Arg | Glu | Gly | Leu | Arg | |
| | | | 260 | | | | | 265 | | | | | 270 | | | |

| gcc | ttc | ctg | gag | agg | ctg | gag | ttc | ggc | agc | ctc | ctc | cac | gag | ttc | ggc | 864 |
|---|---|---|---|---|---|---|---|---|---|---|---|---|---|---|---|---|
| Ala | Phe | Leu | Glu | Arg | Leu | Glu | Phe | Gly | Ser | Leu | Leu | His | Glu | Phe | Gly | |
| | | 275 | | | | | 280 | | | | | 285 | | | | |

| ctc | ctg | gag | gcc | ccc | gcc | ccc | ctg | gag | gag | gcc | ccc | tgg | ccc | ccg | ccg | 912 |
|---|---|---|---|---|---|---|---|---|---|---|---|---|---|---|---|---|
| Leu | Leu | Glu | Ala | Pro | Ala | Pro | Leu | Glu | Glu | Ala | Pro | Trp | Pro | Pro | Pro | |
| 290 | | | | | 295 | | | | | 300 | | | | | | |

| gaa | ggg | gcc | ttc | gtg | ggc | ttc | gtc | ctc | tcc | cgc | ccc | gag | ccc | atg | tgg | 960 |
|---|---|---|---|---|---|---|---|---|---|---|---|---|---|---|---|---|
| Glu | Gly | Ala | Phe | Val | Gly | Phe | Val | Leu | Ser | Arg | Pro | Glu | Pro | Met | Trp | |
| 305 | | | | 310 | | | | | 315 | | | | | 320 | | |

| gcg | gag | ctt | aaa | gcc | ctg | gcc | gcc | tgc | agg | gac | ggc | cgg | gtg | cac | cgg | 1008 |
|---|---|---|---|---|---|---|---|---|---|---|---|---|---|---|---|---|
| Ala | Glu | Leu | Lys | Ala | Leu | Ala | Ala | Cys | Arg | Asp | Gly | Arg | Val | His | Arg | |
| | | | 325 | | | | | 330 | | | | | 335 | | | |

| gca | gca | gac | ccc | ttg | gcg | ggg | cta | aag | gac | ctc | aag | gag | gtc | cgg | ggc | 1056 |
|---|---|---|---|---|---|---|---|---|---|---|---|---|---|---|---|---|
| Ala | Ala | Asp | Pro | Leu | Ala | Gly | Leu | Lys | Asp | Leu | Lys | Glu | Val | Arg | Gly | |
| | | | 340 | | | | | 345 | | | | | 350 | | | |

| ctc | ctc | gcc | aag | gac | ctc | gcc | gtc | ttg | gcc | tcg | agg | gag | ggg | cta | gac | 1104 |
|---|---|---|---|---|---|---|---|---|---|---|---|---|---|---|---|---|
| Leu | Leu | Ala | Lys | Asp | Leu | Ala | Val | Leu | Ala | Ser | Arg | Glu | Gly | Leu | Asp | |
| | | | 355 | | | | | 360 | | | | | 365 | | | |

| ctc | gtg | ccc | ggg | gac | gac | ccc | atg | ctc | ctc | gcc | tac | ctc | ctg | gac | ccc | 1152 |
|---|---|---|---|---|---|---|---|---|---|---|---|---|---|---|---|---|
| Leu | Val | Pro | Gly | Asp | Asp | Pro | Met | Leu | Leu | Ala | Tyr | Leu | Leu | Asp | Pro | |
| | 370 | | | | | 375 | | | | | 380 | | | | | |

| tcc | aac | acc | acc | ccc | gag | ggg | gtg | gcg | cgg | cgc | tac | ggg | ggg | gag | tgg | 1200 |
|---|---|---|---|---|---|---|---|---|---|---|---|---|---|---|---|---|
| Ser | Asn | Thr | Thr | Pro | Glu | Gly | Val | Ala | Arg | Arg | Tyr | Gly | Gly | Glu | Trp | |
| 385 | | | | | 390 | | | | | 395 | | | | | 400 | |

| acg | gag | gac | gcc | gcc | cac | cgg | gcc | ctc | ctc | tcg | gag | agg | ctc | cat | cgg | 1248 |
|---|---|---|---|---|---|---|---|---|---|---|---|---|---|---|---|---|
| Thr | Glu | Asp | Ala | Ala | His | Arg | Ala | Leu | Leu | Ser | Glu | Arg | Leu | His | Arg | |
| | | | | 405 | | | | | 410 | | | | | 415 | | |

| aac | ctc | ctt | aag | cgc | ctc | gag | ggg | gag | gag | aag | ctc | ctt | tgg | ctc | tac | 1296 |
|---|---|---|---|---|---|---|---|---|---|---|---|---|---|---|---|---|
| Asn | Leu | Leu | Lys | Arg | Leu | Glu | Gly | Glu | Glu | Lys | Leu | Leu | Trp | Leu | Tyr | |
| | | | 420 | | | | | 425 | | | | | 430 | | | |

| cac | gag | gtg | gaa | aag | ccc | ctc | tcc | cgg | gtc | ctg | gcc | cac | atg | gag | gcc | 1344 |
|---|---|---|---|---|---|---|---|---|---|---|---|---|---|---|---|---|
| His | Glu | Val | Glu | Lys | Pro | Leu | Ser | Arg | Val | Leu | Ala | His | Met | Glu | Ala | |
| | | | 435 | | | | | 440 | | | | | 445 | | | |

| acc | ggg | gta | cgg | cgg | gac | gtg | gcc | tac | ctt | cag | gcc | ctt | tcc | ctg | gag | 1392 |
|---|---|---|---|---|---|---|---|---|---|---|---|---|---|---|---|---|
| Thr | Gly | Val | Arg | Arg | Asp | Val | Ala | Tyr | Leu | Gln | Ala | Leu | Ser | Leu | Glu | |
| 450 | | | | | 455 | | | | | 460 | | | | | | |

| ctt | gcg | gag | gag | atc | cgc | cgc | ctc | gag | gag | gag | gtc | ttc | cgc | ttg | gcg | 1440 |
|---|---|---|---|---|---|---|---|---|---|---|---|---|---|---|---|---|
| Leu | Ala | Glu | Glu | Ile | Arg | Arg | Leu | Glu | Glu | Glu | Val | Phe | Arg | Leu | Ala | |
| 465 | | | | 470 | | | | | 475 | | | | | 480 | | |

| ggc | cac | ccc | ttc | aac | ctc | aac | tcc | cgg | gac | cag | ctg | gaa | agg | gtg | ctc | 1488 |
|---|---|---|---|---|---|---|---|---|---|---|---|---|---|---|---|---|
| Gly | His | Pro | Phe | Asn | Leu | Asn | Ser | Arg | Asp | Gln | Leu | Glu | Arg | Val | Leu | |
| | | | 485 | | | | | 490 | | | | | 495 | | | |

| ttt | gac | gag | ctt | agg | ctt | ccc | gcc | ttg | ggg | aag | acg | caa | aag | aca | ggc | 1536 |
|---|---|---|---|---|---|---|---|---|---|---|---|---|---|---|---|---|
| Phe | Asp | Glu | Leu | Arg | Leu | Pro | Ala | Leu | Gly | Lys | Thr | Gln | Lys | Thr | Gly | |
| | | | 500 | | | | | 505 | | | | | 510 | | | |

| aag | cgc | tcc | acc | agc | gcc | gcg | gtg | ctg | gag | gcc | cta | cgg | gag | gcc | cac | 1584 |
|---|---|---|---|---|---|---|---|---|---|---|---|---|---|---|---|---|
| Lys | Arg | Ser | Thr | Ser | Ala | Ala | Val | Leu | Glu | Ala | Leu | Arg | Glu | Ala | His | |
| | | | | 515 | | | | | 520 | | | | | 525 | | |

| ccc | atc | gtg | gag | aag | atc | ctc | cag | cac | cgg | gag | ctc | acc | aag | ctc | aag | 1632 |
|---|---|---|---|---|---|---|---|---|---|---|---|---|---|---|---|---|
| Pro | Ile | Val | Glu | Lys | Ile | Leu | Gln | His | Arg | Glu | Leu | Thr | Lys | Leu | Lys | |
| | | | 530 | | | | | 535 | | | | | 540 | | | |

```
aac acc tac gtg gac ccc ctc cca agc ctc gtc cac ccg agg acg ggc    1680
Asn Thr Tyr Val Asp Pro Leu Pro Ser Leu Val His Pro Arg Thr Gly
545                 550                 555                 560 cgc ctc cac acc cgc ttc aac cag acg gcc acg gcc acg ggg agg ctt    1728
Arg Leu His Thr Arg Phe Asn Gln Thr Ala Thr Ala Thr Gly Arg Leu
            565                 570                 575 agt agc tcc gac ccc aac ctg cag aac atc ccc gtc cgc acc ccc ttg    1776
Ser Ser Ser Asp Pro Asn Leu Gln Asn Ile Pro Val Arg Thr Pro Leu
                580                 585                 590 ggc cag agg atc cgc cgg gcc ttc gtg gcc gag gcg gtg tgg gcg ttg    1824
Gly Gln Arg Ile Arg Arg Ala Phe Val Ala Glu Ala Val Trp Ala Leu
            595                 600                 605 gtg gcc ctg gac tat agc cag ata gag ctc cgc gtc ctc gcc cac ctc    1872
Val Ala Leu Asp Tyr Ser Gln Ile Glu Leu Arg Val Leu Ala His Leu
        610                 615                 620 tcc ggg gac gaa aac ctg atc agg gtc ttc cag gag ggg aag gac atc    1920
Ser Gly Asp Glu Asn Leu Ile Arg Val Phe Gln Glu Gly Lys Asp Ile
625                 630                 635                 640 cac acc cag acc gca agc tgg atg ttc ggc gtc ccc gag gag gcc gtg    1968
His Thr Gln Thr Ala Ser Trp Met Phe Gly Val Pro Glu Glu Ala Val
                645                 650                 655 gac ccc ctg atg cgc cgg gcg gcc aag acg gtg aac ttc ggc gtc ctc    2016
Asp Pro Leu Met Arg Arg Ala Ala Lys Thr Val Asn Phe Gly Val Leu
            660                 665                 670 tac ggc atg tcc gcc cat agg ctc tcc cag gag ctt gcc atc ccc tac    2064
Tyr Gly Met Ser Ala His Arg Leu Ser Gln Glu Leu Ala Ile Pro Tyr
        675                 680                 685 gag gag gcg gtg gcc ttt ata gag cgc tac ttc caa agc ttc ccc aag    2112
Glu Glu Ala Val Ala Phe Ile Glu Arg Tyr Phe Gln Ser Phe Pro Lys
    690                 695                 700 gtg cgg gcc tgg ata gaa aag acc ctg gag gag ggg agg aag cgg ggc    2160
Val Arg Ala Trp Ile Glu Lys Thr Leu Glu Glu Gly Arg Lys Arg Gly
705                 710                 715                 720 tac gtg gaa acc ctc ttc gga aga agg cgc tac gtg ccc gac ctc aac    2208
Tyr Val Glu Thr Leu Phe Gly Arg Arg Arg Tyr Val Pro Asp Leu Asn
                725                 730                 735 gcc cgg gtg aag agc gtc agg gag gcc gcg gag cgc atg gcc ttc aac    2256
Ala Arg Val Lys Ser Val Arg Glu Ala Ala Glu Arg Met Ala Phe Asn
            740                 745                 750 atg ccc gtc cag ggc acc gcc gcc gac ctc atg aag ctc gcc atg gtg    2304
Met Pro Val Gln Gly Thr Ala Ala Asp Leu Met Lys Leu Ala Met Val
        755                 760                 765 aag ctc ttc ccc cgc ctc cgg gag atg ggg gcc cgc atg ctc ctc cag    2352
Lys Leu Phe Pro Arg Leu Arg Glu Met Gly Ala Arg Met Leu Leu Gln
    770                 775                 780 gtc cac gac gag ctc ctc ctg gag gcc ccc caa gcg cgg gcc gag gag    2400
Val His Asp Glu Leu Leu Leu Glu Ala Pro Gln Ala Arg Ala Glu Glu
785                 790                 795                 800 gtg gcg gct ttg gcc aag gag gcc atg gag aag gcc tat ccc ctc gcc    2448
Val Ala Ala Leu Ala Lys Glu Ala Met Glu Lys Ala Tyr Pro Leu Ala
                805                 810                 815 gtg ccc ctg gag gtg gag gtg ggg atg ggg gag gac tgg ctt tcc gcc    2496
Val Pro Leu Glu Val Glu Val Gly Met Gly Glu Asp Trp Leu Ser Ala
            820                 825                 830 aag ggt tag                                                         2505
Lys Gly

<210> SEQ ID NO 22
<211> LENGTH: 834
<212> TYPE: PRT
```

<213> ORGANISM: Artificial Sequence
<220> FEATURE:
<223> OTHER INFORMATION: Synthetic Construct

<400> SEQUENCE: 22

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
```

```
            385                 390                 395                 400
Thr Glu Asp Ala Ala His Arg Ala Leu Leu Ser Glu Arg Leu His Arg
                    405                 410                 415

Asn Leu Leu Lys Arg Leu Glu Gly Glu Lys Leu Leu Trp Leu Tyr
            420                 425                 430

His Glu Val Glu Lys Pro Leu Ser Arg Val Leu Ala His Met Glu Ala
                435                 440                 445

Thr Gly Val Arg Arg Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                    485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                    565                 570                 575

Ser Ser Ser Asp Pro Asn Leu Gln Asn Ile Pro Val Arg Thr Pro Leu
                580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
        610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Glu Glu Ala Val
                    645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                    725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
        770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                    805                 810                 815
```

Val Pro Leu Glu Val Glu Val Gly Met Gly Glu Asp Trp Leu Ser Ala
        820                 825                 830

Lys Gly

<210> SEQ ID NO 23
<211> LENGTH: 832
<212> TYPE: PRT
<213> ORGANISM: Thermus aquaticus

<400> SEQUENCE: 23

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Ala Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

```
Ala Lys Asp Leu Ser Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
            755                 760                 765
```

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 24
<211> LENGTH: 834
<212> TYPE: PRT
<213> ORGANISM: Thermus thermophilus HB-8

<400> SEQUENCE: 24

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
              325                 330                 335

Ala Ala Asp Pro Leu Ala Gly Leu Lys Asp Leu Lys Glu Val Arg Gly
              340                 345                 350

Leu Leu Ala Lys Asp Leu Ala Val Leu Ala Ser Arg Glu Gly Leu Asp
              355                 360                 365

Leu Val Pro Gly Asp Asp Pro Met Leu Leu Ala Tyr Leu Leu Asp Pro
        370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
              405                 410                 415

Asn Leu Leu Lys Arg Leu Glu Gly Glu Lys Leu Leu Trp Leu Tyr
              420                 425                 430

His Glu Val Glu Lys Pro Leu Ser Arg Val Leu Ala His Met Glu Ala
              435                 440                 445

Thr Gly Val Arg Arg Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
              485                 490                 495

Phe Asp Glu Leu Arg Leu Pro Ala Leu Gly Lys Thr Gln Lys Thr Gly
              500                 505                 510

Lys Arg Ser Thr Ser Ala Ala Val Leu Glu Ala Leu Arg Glu Ala His
              515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
              565                 570                 575

Ser Ser Ser Asp Pro Asn Leu Gln Asn Ile Pro Val Arg Thr Pro Leu
              580                 585                 590

Gly Gln Arg Ile Arg Arg Ala Phe Val Ala Glu Ala Gly Trp Ala Leu
              595                 600                 605

Val Ala Leu Asp Tyr Ser Gln Ile Glu Leu Arg Val Leu Ala His Leu
        610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
              645                 650                 655

Asp Pro Leu Met Arg Arg Ala Ala Lys Thr Val Asn Phe Gly Val Leu
              660                 665                 670

Tyr Gly Met Ser Ala His Arg Leu Ser Gln Glu Leu Ala Ile Pro Tyr
              675                 680                 685

Glu Glu Ala Val Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
              725                 730                 735

-continued

```
Ala Arg Val Lys Ser Val Arg Glu Ala Glu Arg Met Ala Phe Asn
            740                 745                 750
Met Pro Val Gln Gly Thr Ala Ala Asp Leu Met Lys Leu Ala Met Val
        755                 760                 765
Lys Leu Phe Pro Arg Leu Arg Glu Met Gly Ala Arg Met Leu Leu Gln
    770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
            820                 825                 830
Lys Gly
```

<210> SEQ ID NO 25
<211> LENGTH: 841
<212> TYPE: PRT
<213> ORGANISM: Thermus aquaticus

<400> SEQUENCE: 25

```
Met Arg Gly Met Leu Pro Leu Phe Glu Pro Lys Gly Arg Val Leu Leu
1               5                   10                  15
Val Asp Gly His His Leu Ala Tyr Arg Thr Phe His Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Asp Ala Val Ile Val
    50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
```

```
Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
```

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
            725                 730                 735

Gly Pro Arg Arg Ala Pro Arg Arg Leu Val Lys Ser Val Arg Glu Ala
                740                 745                 750

Ala Glu Arg Met Ala Phe Asn Met Pro Val Gln Gly Thr Ala Ala Asp
            755                 760                 765

Leu Met Lys Leu Ala Met Val Lys Leu Phe Pro Arg Leu Glu Glu Met
        770                 775                 780

Gly Ala Arg Met Leu Leu Gln Val His Asp Glu Leu Val Leu Glu Ala
785                 790                 795                 800

Pro Lys Glu Arg Ala Glu Ala Val Ala Arg Leu Ala Lys Glu Val Met
                805                 810                 815

Glu Gly Val Tyr Pro Leu Ala Val Pro Leu Glu Val Glu Val Gly Ile
            820                 825                 830

Gly Glu Asp Trp Leu Ser Ala Lys Glu
        835                 840

<210> SEQ ID NO 26
<211> LENGTH: 893
<212> TYPE: PRT
<213> ORGANISM: Thermotoga maritima

<400> SEQUENCE: 26

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
        35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
    130                 135                 140

Asn Glu Lys Ile Lys Met Leu Gln Leu Val Asn Glu Lys Ile Lys Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Glu Lys Tyr Lys Asp Leu Glu Asp Ile Leu Asn His Val Arg Glu Leu
    210                 215                 220

-continued

```
Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
            245                 250                 255

Asn Trp Glu Glu Leu Arg Tyr Gln Gly Tyr Asp Arg Glu Lys Leu Leu
        260                 265                 270

Pro Leu Leu Lys Glu Leu Glu Phe Ala Ser Ile Met Lys Glu Leu Gln
            275                 280                 285

Leu Tyr Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
            325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
    355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
            405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
    435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
            485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
    515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
            565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
    595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
```

```
                  645                 650                 655
Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Glu Gly Ile Asp Val His Thr Leu
            690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
                755                 760                 765

Tyr Ile Gln Arg Val Val Ser Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
            850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 27
<211> LENGTH: 866
<212> TYPE: PRT
<213> ORGANISM: Thermodesulfobacterium sp.

<400> SEQUENCE: 27

Met Val Ser Ser Tyr Leu Lys Lys Ile Pro Lys Asp Thr Val Ile Leu
1               5                   10                  15

Ile Asp Gly Ser Ser Phe Ile Tyr Arg Ala Tyr Phe Ala Ile Pro Gly
                20                  25                  30

Tyr Leu Ala Thr Thr Lys Gly Phe Pro Thr Lys Ala Ile Phe Gly Val
            35                  40                  45

Thr Gln Met Val Leu Lys Ile Leu Lys Glu Trp Asp Pro Glu Tyr Ile
        50                  55                  60

Ile Trp Phe Met Asp Glu Lys Glu Pro Thr Phe Arg His Glu Ile Tyr
65                  70                  75                  80

Glu Asn Tyr Lys Ala Thr Arg Pro Lys Met Pro Asp Asp Leu Lys Ile
                85                  90                  95

Gln Ile Pro Tyr Ile Arg Asn Ile Ile His Ser Leu Gly Ile Pro Val
            100                 105                 110

Leu Ser His Pro Gly Tyr Glu Gly Asp Asp Leu Ile Ala Ser Phe Ile
        115                 120                 125
```

```
Lys Asn Ile Ile Lys Lys Gln Asn Leu Ser Ala Ile Ile Val Ala Gly
    130                 135                 140

Asp Lys Asp Leu Tyr Ser Leu Ile Asp Lys Asn Ile Ala Ile Tyr Asp
145                 150                 155                 160

Pro Val Arg Glu Lys Phe Leu Asp Leu Asp Ala Phe Leu Glu Lys Tyr
                165                 170                 175

Gln Phe Pro Pro Gln Val Phe Pro Glu Phe Arg Ala Leu Thr Gly Asp
            180                 185                 190

Pro Ser Asp Asn Ile Pro Gly Val Pro Gly Ile Gly Lys Thr Ala
            195                 200                 205

Lys Glu Leu Leu Ile Lys Phe Lys Asn Leu Glu Asn Leu Tyr Gln Asn
    210                 215                 220

Ile Lys Gln Val Ser Leu Ser Lys Leu Arg Glu Ser Leu Leu Lys Tyr
225                 230                 235                 240

Lys Asp Gln Val Leu Asn Asn Leu Ser Leu Leu Thr Leu Asn Tyr Asn
                245                 250                 255

Ala Pro Leu Pro Ser Leu Asp Ile Ile Tyr Tyr Lys Arg Lys Glu Pro
            260                 265                 270

Asp Tyr Ser Thr Leu Arg Lys Ile Phe Lys Glu Leu Glu Phe Arg Lys
    275                 280                 285

Leu Leu Ser Glu Ile Lys Tyr Thr Pro Pro Glu Phe Lys Pro Leu Leu
    290                 295                 300

Ile Glu Asn Lys Asp Leu Ser Gln Ile Pro Glu Arg Asp Tyr Leu Ser
305                 310                 315                 320

Leu Phe Pro Leu Gln Tyr Gln Gly Tyr Ile Phe Asn Leu Ala His Ala
                325                 330                 335

Pro Glu Ile Ala Val Ala Phe Ser Lys Glu Ala Tyr Lys Leu Ser
            340                 345                 350

Thr Ser Cys Leu Lys Asp Leu Ile Ser Lys Phe Thr Lys Thr Lys Phe
    355                 360                 365

Ile Leu His Asp Tyr Lys Asn Phe Leu Lys Leu Phe Gly Phe Ser Leu
    370                 375                 380

Asn Lys Val Phe Asp Thr Lys Leu Ala Ser Tyr Leu Leu Asn Pro Ser
385                 390                 395                 400

Leu Lys Lys Tyr Glu Leu Glu Phe Leu Leu Gln Glu Tyr Leu Asp Ile
                405                 410                 415

Ser Leu Gly Ser Ser Lys Ile Ser Glu Asp Glu Ile Ala Ile Lys
            420                 425                 430

Thr Cys Ser Leu Phe Leu Leu Gly Lys Glu Leu Ile Asn Arg Ile Glu
    435                 440                 445

Glu Glu Gly Leu Ser Glu Trp Leu Glu Lys Val Glu Ile Pro Leu Ser
    450                 455                 460

Glu Val Leu Phe Glu Met Glu Lys Lys Gly Phe Lys Ile Asp Leu Glu
465                 470                 475                 480

Tyr Val Arg Thr Leu Asn Gln Glu Tyr Gln Lys Thr Leu Lys Glu Leu
                485                 490                 495

Glu Asp Lys Leu Phe Glu Ile Ala Gly Cys Arg Phe Asn Pro Lys Ser
            500                 505                 510

Ser Gln Glu Val Ser Asn Ile Leu Phe Lys Lys Leu Asn Leu Pro Ser
    515                 520                 525

Ile Lys Lys Thr Pro Lys Ser Ser Leu Pro Ser Thr Asp Ala Glu Val
    530                 535                 540

Leu Glu Glu Leu Ala Pro Leu His Pro Phe Val Arg Leu Leu Ile Gln
```

```
                545                 550                 555                 560
Tyr Arg Thr Leu Tyr Lys Ile Lys Ser Thr Tyr Leu Glu Ala Phe Leu
                    565                 570                 575
Lys Tyr Ala Glu Thr Lys Thr His Arg Leu His Thr Glu Phe Asn Gln
                580                 585                 590
Thr Gly Thr Ala Thr Gly Arg Leu Ser Ser Gln Asn Pro Asn Leu Gln
            595                 600                 605
Asn Ile Pro Ile Lys Gly Glu Glu Gly Leu Ser Ile Arg Arg Ala Phe
        610                 615                 620
Ile Ala Glu Asp Gly Cys Met Leu Cys Ser Leu Asp Tyr Ser Gln Ile
625                 630                 635                 640
Glu Leu Arg Ile Leu Ala His Phe Ser Glu Asp Lys Asn Leu Ile Ser
                645                 650                 655
Ala Phe Glu Lys Gly Glu Asp Ile His Thr Phe Thr Ala Cys Glu Val
                660                 665                 670
Phe Gly Val Thr Pro Glu Lys Val Thr Pro Glu Met Arg Arg Met Ser
            675                 680                 685
Lys Ala Ile Asn Phe Gly Ile Ala Tyr Gly Met Ser Ala Tyr Gly Leu
        690                 695                 700
Ala Lys Glu Leu Lys Ile Ser Pro Lys Glu Ala Glu Ile Ile Ile Asn
705                 710                 715                 720
Arg Tyr Phe Ser Arg Tyr Pro Gly Ile Lys Glu Tyr Ile Gln Lys Thr
                725                 730                 735
Ile Glu Phe Ala Lys Glu Asn Gly Tyr Val Lys Thr Leu Val Gly Arg
                740                 745                 750
Lys Arg Tyr Ile Pro Glu Leu Phe Ser Pro Asn Lys Ser Ile Lys Glu
            755                 760                 765
Leu Gly Gln Arg Met Ala Ile Asn Thr Pro Ile Gln Gly Ser Ala Ala
        770                 775                 780
Asp Leu Ile Lys Cys Ala Met Val Ala Leu Gln Lys Glu Leu Lys Arg
785                 790                 795                 800
His Asn Leu Lys Thr Ala Ile Ile Leu Gln Val His Asp Glu Leu Val
                805                 810                 815
Leu Glu Val Pro Glu Glu Glu Ile Glu Ile Ile Lys Glu Leu Ala Pro
                820                 825                 830
Lys Ile Met Glu Asn Pro Phe Lys Tyr Leu Asn Leu Pro Tyr Lys Leu
            835                 840                 845
Asn Val Pro Ile Lys Val Asn Phe Ser Phe Gly Lys Asn Trp Ala Glu
        850                 855                 860
Cys Lys
865

<210> SEQ ID NO 28
<211> LENGTH: 289
<212> TYPE: PRT
<213> ORGANISM: Aquifex aeolicus VF5

<400> SEQUENCE: 28

Met Lys Thr Leu Tyr Ile Leu Asp Gly Ser Ser Phe Val Tyr Arg Ser
1               5                   10                  15
Phe Phe Ala Leu Pro Pro Leu Ser Thr Ser Lys Gly Phe Pro Thr Asn
                20                  25                  30
Ala Ile Tyr Gly Phe Leu Arg Met Leu Phe Ser Leu Ile Lys Lys Glu
            35                  40                  45
```

Arg Pro Gln Tyr Leu Val Val Phe Asp Ala Pro Ala Lys Thr Lys
    50              55                  60
Arg Glu Lys Ile Tyr Ala Asp Tyr Lys Gln Arg Pro Lys Ala Pro
65              70                  75                  80
Asp Pro Leu Lys Val Gln Ile Pro Val Ile Lys Glu Ile Leu Lys Leu
                85                  90                  95
Ala Gly Ile Pro Leu Leu Glu Leu Pro Gly Tyr Glu Ala Asp Asp Val
            100                 105                 110
Ile Ala Tyr Leu Ala Glu Lys Phe Ser Gln Lys Gly Phe Lys Val Lys
            115                 120                 125
Ile Tyr Ser Pro Asp Lys Asp Leu Leu Gln Leu Val Ser Glu Asn Val
    130                 135                 140
Leu Val Ile Asn Pro Met Asn Asp Glu Val Phe Thr Lys Glu Arg Val
145                 150                 155                 160
Ile Lys Lys Phe Gly Val Glu Pro Gln Lys Ile Pro Asp Tyr Leu Ala
                165                 170                 175
Leu Val Gly Asp Lys Val Asp Asn Val Pro Gly Ile Glu Gly Val Gly
            180                 185                 190
Pro Lys Thr Ala Ile Asn Ile Leu Lys Lys Tyr Gly Ser Val Glu Asn
            195                 200                 205
Ile Leu Lys Asn Trp Glu Lys Phe Gln Arg Glu Phe Pro Arg Ala Lys
    210                 215                 220
Lys Glu Asp Leu Glu Leu Ser Tyr Lys Leu Val Lys Leu Tyr Thr Asp
225                 230                 235                 240
Leu Asp Ile Glu Leu Ser Glu Asp Leu Lys Ile Lys Arg Pro Asp
                245                 250                 255
Leu Asn Lys Leu Lys Gln Lys Leu Gln Glu Leu Glu Met Lys Ser Leu
            260                 265                 270
Leu Lys Glu Val Asp Lys Ile Phe Arg Gln Ala Ser Gln Arg Ser Leu
            275                 280                 285
Phe

<210> SEQ ID NO 29
<211> LENGTH: 574
<212> TYPE: PRT
<213> ORGANISM: Aquifex aeolicus VF5

<400> SEQUENCE: 29

Met Asp Phe Glu Tyr Val Thr Gly Glu Glu Gly Leu Lys Lys Ala Ile
1               5                   10                  15
Lys Arg Leu Glu Asn Ser Pro Tyr Leu Tyr Leu Asp Thr Glu Thr Thr
                20                  25                  30
Gly Asp Arg Ile Arg Leu Val Gln Ile Gly Asp Glu Glu Asn Thr Tyr
            35                  40                  45
Val Ile Asp Leu Tyr Glu Ile Gln Asp Ile Glu Pro Leu Arg Lys Leu
    50                  55                  60
Ile Asn Glu Arg Gly Ile Val Gly His Asn Leu Lys Phe Asp Leu Lys
65              70                  75                  80
Tyr Leu Tyr Arg Tyr Gly Ile Phe Pro Ser Ala Thr Phe Asp Thr Met
                85                  90                  95
Ile Ala Ser Tyr Leu Leu Gly Tyr Glu Arg His Ser Leu Asn His Ile
            100                 105                 110
Val Ser Asn Leu Leu Gly Tyr Ser Met Asp Lys Ser Tyr Gln Thr Ser
            115                 120                 125

-continued

```
Asp Trp Gly Ala Ser Val Leu Ser Asp Ala Gln Leu Lys Tyr Ala Ala
            130                 135                 140

Asn Asp Val Ile Val Leu Arg Glu Leu Phe Pro Lys Met Arg Asp Met
145                 150                 155                 160

Leu Asn Glu Leu Asp Ala Glu Arg Gly Glu Glu Leu Leu Lys Thr Arg
                165                 170                 175

Thr Ala Lys Ile Phe Asp Leu Lys Ser Pro Val Ala Ile Val Glu Met
            180                 185                 190

Ala Phe Val Arg Glu Val Ala Lys Leu Glu Ile Asn Gly Phe Pro Val
                195                 200                 205

Asp Val Glu Glu Leu Thr Asn Lys Leu Lys Ala Val Glu Arg Glu Thr
210                 215                 220

Gln Lys Arg Ile Gln Glu Phe Tyr Ile Lys Tyr Arg Val Asp Pro Leu
225                 230                 235                 240

Ser Pro Lys Gln Leu Ala Ser Leu Leu Thr Lys Lys Phe Lys Leu Asn
                245                 250                 255

Leu Pro Lys Thr Pro Lys Gly Asn Val Ser Thr Asp Asp Lys Ala Leu
            260                 265                 270

Thr Ser Tyr Gln Asp Val Glu Pro Val Lys Leu Val Leu Glu Ile Arg
            275                 280                 285

Lys Leu Lys Lys Ile Ala Asp Lys Leu Lys Glu Leu Lys Glu His Leu
290                 295                 300

Lys Asn Gly Arg Val Tyr Pro Glu Phe Lys Gln Ile Gly Ala Val Thr
305                 310                 315                 320

Gly Arg Met Ser Ser Ala His Pro Asn Ile Gln Asn Ile His Arg Asp
                325                 330                 335

Met Arg Gly Ile Phe Lys Ala Glu Gly Asn Thr Phe Val Ile Ser
            340                 345                 350

Asp Phe Ser Gln Ile Glu Leu Arg Ile Ala Ala Glu Tyr Val Lys Asp
            355                 360                 365

Pro Leu Met Leu Asp Ala Phe Lys Lys Gly Lys Asp Met His Arg Tyr
370                 375                 380

Thr Ala Ser Val Val Leu Gly Lys Lys Glu Glu Ile Thr Lys Glu
385                 390                 395                 400

Glu Arg Gln Leu Ala Lys Ala Ile Asn Phe Gly Leu Ile Tyr Gly Ile
                405                 410                 415

Ser Ala Lys Gly Leu Ala Glu Tyr Ala Lys Leu Gly Tyr Gly Val Glu
            420                 425                 430

Ile Ser Leu Glu Glu Ala Gln Val Leu Arg Glu Arg Phe Phe Lys Asn
            435                 440                 445

Phe Lys Ala Phe Lys Glu Trp His Asp Arg Val Lys Lys Glu Leu Lys
            450                 455                 460

Glu Lys Gly Glu Val Lys Gly His Thr Leu Leu Gly Arg Arg Phe Ser
465                 470                 475                 480

Ala Asn Thr Phe Asn Asp Ala Val Asn Tyr Pro Ile Gln Gly Thr Gly
                485                 490                 495

Ala Asp Leu Leu Lys Leu Ala Val Leu Leu Phe Asp Ala Asn Leu Gln
            500                 505                 510

Lys Lys Gly Ile Asp Ala Lys Leu Val Asn Leu Val His Asp Glu Ile
            515                 520                 525

Val Val Glu Cys Glu Lys Glu Lys Ala Glu Glu Val Lys Glu Ile Leu
530                 535                 540
```

```
Glu Lys Ser Met Lys Thr Ala Gly Lys Ile Ile Leu Lys Glu Val Pro
545                 550                 555                 560

Val Glu Val Glu Ser Val Ile Asn Glu Arg Trp Thr Lys Asp
                565                 570
```

DNA POLYMERASE

CROSS REFERENCE TO RELATED APPLICATIONS

This application is a Continuation of co-pending U.S. application Ser. No. 14/130,636 filed on Aug. 22, 2014, which is a National Stage of PCT/JP2012/067872 filed on Jul. 12, 2012, which claims priority to Application No. 2011-153410 filed in Japan, on Jul. 12, 2011. The entire contents of all of the above applications are hereby incorporated by reference.

REFERENCE TO SEQUENCE LISTING SUBMITTED VIA EFS-WEB

This application includes an electronically submitted sequence listing in .txt format. The .txt file contains a sequence listing entitled "2016-10-18 0230-0324PUS1_ST25.txt" created on Oct. 18, 2016 and is 162,956 bytes in size. The sequence listing contained in this .txt file is part of the specification and is hereby incorporated by reference herein in its entirety.

TECHNICAL FIELD

The present invention relates to novel DNA polymerases. The DNA polymerases of this invention are particularly useful for PCR.

BACKGROUND ART

DNA polymerases are enzymes that can synthesize new DNA strands along template DNA strands in vitro. DNA polymerases can synthesize new DNA strands from a template DNA, an oligonucleotide serving as a primer, and four types of deoxynucleotides (dATP, dGTP, dCTP, and dTTP). DNA polymerases are also used in many genetic engineering techniques, including nucleotide sequencing and PCR.

Thermostability of polymerases is essential for PCR, and the current protocol of nucleotide sequencing generally uses the cycle sequencing method using a thermostable DNA polymerase as a standard technique. In order to find a thermostable enzyme, one would usually search enzymes produced by thermophilic microorganisms. Among thermophilic bacteria, those which proliferate at an optimum growth temperature of at least 80° C. are particularly referred to as "hyperthermophilic bacteria" and serve as excellent resources for thermostable enzymes. Taq DNA polymerases (also referred to as "Taq polymerases") which are currently widely used in PCR were originally isolated from the thermophilic eubacterium *Thermus aquaticus.*

Based on the similarity in amino acid sequences, DNA polymerases are categorized into seven groups: Families A, B, C, D, E, X and Y. Enzymes belonging to the same family basically exhibit very similar properties. The enzymes that are in practical use are those belonging to Families A and B.

Family A enzymes have superior performance in recognizing dideoxynucleotides as substrates and are most appropriate for nucleotide sequencing. Thus, the enzymes contained in currently commercially available sequencing kits are all those which belong to Family A and are derived from thermophilic eubacteria. In PCR, Family A and B enzymes are selectively used depending on the purpose.

Family B enzymes are not suitable for nucleotide sequencing because of poor incorporation of dideoxynucleotides but have 3'-5' exonuclease activity which is involved in the accuracy in synthesizing DNA strands according to the sequences of template strands—during amplification, the enzymes of this family produce less errors than Family A enzymes such as Taq polymerases with no exonuclease activity. The Family B enzymes that are commercialized are those derived from hyperthermophilic archaea. In order to perform PCR more accurately, it is advisable to use Family B enzymes, whereas in order to amplify long-chain DNA, Family A enzymes can be selected due to their superior extensibility and superior DNA synthesis efficiency.

Comparison between the two DNA polymerases that are derived from bacteria belonging to the genus *Thermus* and which have been up to now widely used as PCR enzymes shows that Taq DNA polymerase only has weak reverse transcriptional activity, while Tth DNA polymerase ("Tth polymerase") derived from *Thermus thermophilus* has significantly strong reverse transcriptional activity. This property of Tth polymerase is utilized in a simple RT-PCR technology in which a single enzyme is used in a single reaction tube to synthesize cDNA from mRNA by reverse transcription and then amplify the synthesized cDNA. Since the optimum temperature of this enzyme is high, the enzyme makes it possible to perform a reverse transcription reaction at relatively high temperatures (around 60° C.) and is also effective for the reverse transcription of RNA which easily forms a three-dimensional structure, but the enzyme is not suitable for the synthesis of long cDNAs like those reaching as long as several kilo bases in length.

PCR is a gene analysis technology that is widely used throughout the world as a routinely utilized technique. Accordingly, there is a need for a DNA polymerase that is more convenient, easier-to-use, and more reliable, and it is also desired to provide various DNA polymerases that can amplify various DNAs appropriately depending on the template to be used as well as the purpose to be needed for PCR such as extensibility, rapidity, and accuracy.

As regards modification of Taq polymerases, there have been hitherto reports stating that primers were designed based on the segments of an amino acid sequence highly conserved in Family A DNA polymerases, each of which contains an active site, gene fragments were amplified by PCR using DNA samples derived from hot spring soil as templates, and the corresponding segments of a wild-type Taq polymerase gene were substituted by the amplified fragments, whereby obtained were chimeric DNA polymerases with higher extension activity than Taq polymerases (Patent Documents 1 and 2). Another report showed that on the basis of metagenomic analysis and the three-dimensional structure information of DNA polymerases, one or more mutations were introduced that produce an increased the total electric charges of glutamic acid at position 742 and alanine at position 743 in an amino acid sequence of a Taq polymerase, whereby obtained was a modified Taq polymerase that is superior to the Taq polymerase in at least one of: primer extension activity; binding activity on a primer annealed to a template DNA; and PCR performance (Patent Document 3).

CITATION LIST

Patent Documents

Patent Document 1: Japanese Patent Application Publication No. JP 2006-101791
Patent Document 2: Japanese Patent Application Publication No. JP 2006-204267

Patent Document 3: Japanese Patent No. JP 4193997

SUMMARY OF THE INVENTION

Technical Problem

The present inventors made detailed comparison between the amino acid sequences of Taq polymerases and Tth polymerases, focusing on the difference in the properties associated with their amino acid sequence identity (about 80%) and reverse transcriptional activity. However, based on this comparison alone, it was difficult to predict on what the difference in their properties depends.

On the other hand, the inventors have accumulated the results of the study in which the properties of DNA polymerases derived from a diverse range of organisms are reflected as those of chimeric Taq polymerases by the following method: hot spring soil samples are collected from various places, DNAs are directly extracted from the samples, fragments of DNA polymerase genes possessed by various kinds of organisms contained in the samples are amplified by PCR based on the obtained DNAs (metagenomes), and the resulting fragments are recombined in vitro with the homologous regions of Taq polymerase genes, whereby chimeric enzymes are constructed. It is, of course, ideal that the gene obtained from a metagenomic DNA contains a full-length sequence, but many metagenomic DNAs extracted from environmental samples are often fragmented or damaged; thus, it is a very difficult task to obtain a full-length gene directly. Therefore, we constructed the following study system: a gene segment encoding an active center that significantly affects the activity of a DNA polymerase and peripheral regions thereof is obtained from a metagenome, and the obtained segment is substituted with the homologous region of a Taq polymerase gene to create a chimeric enzyme gene, so that the obtained gene fragment could directly affect the basic properties of a DNA polymerase.

We created a phylogenetic tree (not shown in the present application) by checking the results of determining the activities of many chimeric Taq polymerases constructed in such a way as described above, against each other, and comparing the sequences of the gene fragments that are derived from metagenomic DNAs and which were introduced into wild-type Taq polymerases. As a result of predicting the factors that might change the activities of the chimeric Taq polymerases, we found the chimeric Taq polymerases 8-16, 18-7, 1-8, and 3-7 which have significantly strong reverse transcriptional activity as compared with the wild-type Taq polymerases.

First, we compared the sequences of 8-16, a Taq polymerase, and a Tth polymerase with each other and, as a result, did not find any amino acid residue that is common between 8-16 and the Tth polymerase but is different between 8-16 and the Taq polymerase. However, among ten amino acid residues that are different between the Taq and Tth polymerases, there were three amino acid residues that are completely different in nature between these three polymerases. Thus, we focused on these three amino acid residues and decided to introduce mutations to them.

Next, we compared the sequence of 18-7 with each of the sequences of a Taq polymerase and a Tth polymerase to thereby search for an amino acid residue that is common between 18-7 and the Tth polymerase which both have reverse transcriptional activity but not common between 18-7 and the Taq polymerase, and, as a result, four amino acid residues were found. Among them, there was one amino acid residue that is greatly different in nature between 18-7/Tth polymerase and the Taq polymerase; thus, we decided to introduce a mutation to this amino acid residue.

Further, as regards 1-8 and 3-7, these chimeric polymerases have strong primer extension activity and reverse transcriptional activity, whereas there was a chimeric enzyme (1-20) that has almost the same sequence as said polymerases but is extremely weak in activity. We compared the sequences of the three enzymes: 1-8, 3-7 as well as 1-20 mentioned above. As a result, we found two amino acids that are completely inconsistent between these sequences, and selected the one that is only inconsistent in 1-20, which is greatly different in activity, and decided to introduce a mutation to it.

We compared the mutant proteins of the site-specific mutated Taq polymerase and Tth polymerase constructed according to the above-noted strategy, with the wild-type enzymes. First, the mutant proteins were evaluated for nucleotide incorporation activity using an activated DNA as a template, whereupon the respective specific activities of the mutants which are relative to those of the wild-type Taq polymerase taken as 100% demonstrated that there is in principle no significant change in DNA polymerase activity. Next, these enzymes were determined for reverse transcriptional activity by a nucleotide incorporation assay using RNA as a template, whereupon there were found a mutant Taq polymerase (Taq R651E) and a mutant Tth polymerase (Tth P653E), which respectively have a reverse transcriptional activity 1.4 and 1.7 times greater than that of the wild-type Tth polymerase. Comparison of the sequences showed that the amino acid at position 653 in the Tth polymerase corresponds to that at position 651 in the Taq polymerase (refer to FIG. 1). The inventors thus created mutant DNA polymerases having presumably very useful properties, and completed the present invention.

The present invention provides the following:

[1] A DNA polymerase which is any one of (a) to (c) mentioned below:

(a) a DNA polymerase comprising: an amino acid sequence modified from the amino acid sequence of SEQ ID NO: 12, which has a substitution of the arginine residue at position 651 by an amino acid residue having a negatively charged side chain; or an amino acid sequence that is modified from an amino acid sequence of a Family A DNA polymerase derived from a thermophilic eubacterium, which has a substitution of an amino acid residue corresponding to position 651 in SEQ ID NO: 12 by an amino acid residue having a negatively charged side chain;

(b) a DNA polymerase comprising an amino acid sequence modified from the amino acid sequence of the DNA polymerase as recited in (a), which has a substitution, deletion, insertion and/or addition of one to nine amino acid residues which exclude the amino acid residue substituted in (a); and (c) a DNA polymerase comprising an amino acid sequence that is at least 95% identical to the amino acid sequence of the DNA polymerase as recited in (a), with the proviso that the amino acid residue substituted in (a) is the same as the amino acid residue in (a);

[2] The DNA polymerase as recited in [1], wherein the Family A DNA polymerase derived from a thermophilic eubacterium is selected from the group consisting of DNA polymerases derived from *Thermus aquaticus* or DNA polymerases derived from *Thermus thermophilus*;

[3] The DNA polymerase as recited in [1] or [2], wherein the DNA polymerase of (a) is:

(a1) a DNA polymerase comprising an amino acid sequence modified from the amino acid sequence of SEQ ID NO: 12, which has a substitution of the arginine residue at position 651 by an amino acid residue having a negatively charged side chain;

[4] The DNA polymerase as recited in [3], wherein the DNA polymerase of (a1) comprises the amino acid sequence of SEQ ID NO: 20;

[5] The DNA polymerase as recited in [3] or [4], wherein the DNA polymerase of (b) or (c) has a reverse transcriptional activity of at least $16.0 \times 10^3$ U/mg;

[6] A polynucleotide which is any one of (A1) to (D1) mentioned below:
(A1) a polynucleotide comprising the nucleotide sequence of SEQ ID NO: 19;
(B1) a polynucleotide comprising a nucleotide sequence encoding the DNA polymerase as recited in [3];
(C1) a polynucleotide that hybridizes under stringent conditions with a polynucleotide comprising a complementary sequence to the nucleotide sequence of SEQ ID NO: 19, and which encodes a DNA polymerase; and
(D1) a polynucleotide encoding a DNA polymerase comprising a sequence at least 95% identical to the nucleotide sequence of SEQ ID NO: 19;

[7] The polynucleotide as recited in [6], wherein the DNA polymerase in (C1) or (D1) has a reverse transcriptional activity of at least $16.0 \times 10^3$ U/mg;

[8] The DNA polymerase as recited in [1] or [2], wherein the DNA polymerase of (a) is:
(a2) a DNA polymerase comprising an amino acid sequence modified from the amino acid sequence of SEQ ID NO: 14, which has a substitution of the proline residue at position 653 by an amino acid residue having a negatively charged side chain;

[9] The DNA polymerase as recited in [8], wherein the DNA polymerase of (a2) comprises the amino acid sequence of SEQ ID NO: 22;

[10] The DNA polymerase as recited in [8] or [9], wherein the DNA polymerase of (b) or (c) has a reverse transcriptional activity of at least $16.0 \times 10^3$ U/mg;

[11] A polynucleotide which is any one of (A2) to (D2) mentioned below:
(A2) a polynucleotide comprising the nucleotide sequence of SEQ ID NO: 21;
(B2) a polynucleotide comprising a nucleotide sequence encoding the DNA polymerase as recited in [8];
(C2) a polynucleotide that hybridizes under stringent conditions with a polynucleotide comprising a complementary sequence to the nucleotide sequence of SEQ ID NO: 21, and which encodes a DNA polymerase; and
(D2) a polynucleotide encoding a DNA polymerase comprising a sequence at least 95% identical to the nucleotide sequence of SEQ ID NO: 21;

[12] The polynucleotide as recited in [11], wherein the DNA polymerase in (C2) or (D2) has a reverse transcriptional activity of at least $16.0 \times 10^3$ U/mg;

[13] A DNA polymerase which is any one of (a3) to (c3) mentioned below:
(a3) a DNA polymerases comprising an amino acid sequence modified from the amino acid sequence of SEQ ID NO: 12, which has a substitution of at least one selected from the glutamic acid residue at position 117, the asparatic acid residue at position 119, the asparatic acid residue at position 142, and the asparatic acid residue at position 144 by an amino acid residue having a non-polar aliphatic side chain;

(b3) a DNA polymerase comprising an amino acid sequence modified from the amino acid sequence of the DNA polymerase as recited in (a3), which has a substitution, deletion, insertion and/or addition of one to nine amino acid residues, with the proviso that at least one amino acid residue corresponding to at least one selected from positions 117, 119, 142 and 144 in the amino acid sequence of the DNA polymerase as recited in (a3) remains the same; and (c3) a DNA polymerase comprising an amino acid sequence that is at least 95% identical to the amino acid sequence of the DNA polymerase as recited in (a3), with the proviso that at least one amino acid residue corresponding to at least one selected from positions 117, 119, 142 and 144 in the amino acid sequence of the DNA polymerase as recited in (a3) remains the same;

[14] The DNA polymerase as recited in [13], wherein the DNA polymerase of (a3) comprises the amino acid sequence of SEQ ID NO: 16;

[15] The DNA polymerase as recited in [13] or [14], wherein the DNA polymerase of (b3) or (c3) has a primer extension activity using DNA as a template, of at least 4.00 kb/U·min.

[16] A polynucleotide which is any one of (A3) to (D3) mentioned below:
(A3) a polynucleotide comprising the nucleotide sequence of SEQ ID NO: 15;
(B3) a polynucleotide comprising a nucleotide sequence encoding the DNA polymerase as recited in [13];
(C3) a polynucleotide that hybridizes under stringent conditions with a polynucleotide comprising a complementary sequence to the nucleotide sequence of SEQ ID NO: 15, and which encodes a DNA polymerase; and
(D3) a polynucleotide encoding a DNA polymerase comprising a sequence at least 95% identical to the nucleotide sequence of SEQ ID NO: 15;

[17] The polynucleotide as recited in [16], wherein the DNA polymerase of (C3) or (D3) has a primer extension activity using DNA as a template, of at least 4.00 kb/U·min.

[18] A DNA polymerase which is any one of (a4) to (c4) mentioned below:
(a4) a DNA polymerases comprising an amino acid sequence modified from the amino acid sequence of SEQ ID NO: 12, which has a substitution of at least one selected from the glutamic acid residue at position 117, the asparatic acid residue at position 119, the asparatic acid residue at position 142, and the asparatic acid residue at position 144, as well as the glutamic acid residue at position 742 by an amino acid residue having a non-polar aliphatic side chain;

(b4) a DNA polymerase comprising an amino acid sequence modified from the amino acid sequence of the DNA polymerase as recited in (a4), which has a substitution, deletion, insertion and/or addition of one to nine amino acid residues, with the proviso that amino acid residues corresponding to at least one selected from positions 117, 119, 142 and 144, as well as position 742, in the amino acid sequence of the DNA polymerase as recited in (a4) remain the same; and (c4) a DNA polymerase comprising an amino acid sequence that is at least 95% identical to the amino acid sequence of the DNA polymerase as recited in (a4), with the proviso that amino acid residues corresponding to at least one selected from positions 117, 119, 142 and 144, as well as position 742, in the amino acid sequence of the DNA polymerase as recited in (a4) remain the same;

[19] The DNA polymerase as recited in [18], wherein the DNA polymerase of (a4) comprises the amino acid sequence of SEQ ID NO: 18;

[20] The DNA polymerase as recited in [18] or [19], wherein the DNA polymerase of (b4) or (c4) has a primer extension activity using DNA as a template, of at least 4.00 kb/U·min.

[21] A polynucleotide which is any one of (A4) to (D4) mentioned below:

(A3) a polynucleotide comprising the nucleotide sequence of SEQ ID NO: 17;

(B4) a polynucleotide comprising a nucleotide sequence encoding the DNA polymerase as recited in [18];

(C4) a polynucleotide that hybridizes under stringent conditions with a polynucleotide comprising a complementary sequence to the nucleotide sequence of SEQ ID NO: 17, and which encodes a DNA polymerase; and (D4) a polynucleotide encoding a DNA polymerase comprising a sequence at least 95% identical to the nucleotide sequence of SEQ ID NO: 17;

[22] The polynucleotide as recited in [21], wherein the DNA polymerase of (C4) or (D4) has a primer extension activity using DNA as a template, of at least 4.00 kb/U·min.

[23] A recombinant vector comprising the polynucleotide as recited in any one of [7], [12], [17] and [22];

[24] A transformant comprising the recombinant vector as recited in [23]; and

[25] A process for preparing the DNA polymerase as recited in any one of [1] to [5], [8] to [10], [13] to [15], and [18] to [20], the process comprising a step of culturing the transformant as recited in [24].

BRIEF DESCRIPTION OF THE DRAWINGS

FIG. 1-1 shows a comparison and alignment of the amino acid sequences of Taq and Tth DNA polymerases (SEQ ID NOS: 23 and 24, respectively). The mark "▼" indicates the correspondence between the amino acid at position 651 in the Taq DNA polymerase and the amino acid at position 653 in the Tth DNA polymerase.

FIG. 1-2 (SEQ ID NOS: 25-29, respectively) shows a comparison and alignment of the amino acid sequences of Taq DNA polymerase and other family A DNA polymerases from thermophilic bacteria. The mark "▼" indicates the amino acid at position 651 in the Taq DNA polymerase.

FIG. 1-3 (SEQ ID NOS: 25-29, respectively) shows a comparison and alignment of the amino acid sequences of Taq DNA polymerase and other family A DNA polymerases from thermophilic bacteria. The mark "▼" indicates the amino acid at position 651 in the Taq DNA polymerase.

FIG. 2 shows a photograph of the SDS-PAGE gels concerning purification of Taq DNA polymerase mutants. The purity of each of the prepared Taq DNA polymerase mutants was confirmed by SDS-PAGE analysis (refer to Example 1).

FIG. 3 shows a graph of an actual example of enzymatic activity determination by nucleotide incorporation assay (refer to Example 2). Under the conditions of this test, Taq showed an activity of $3.9 \times 10^5$ U/mg.

FIG. 6 shows the Taq WT amino acid sequence of SEQ ID NO: 12 and the Taq WT nucleotide sequence of SEQ ID NO: 11.

FIG. 7 shows the Tth WT amino acid sequence of SEQ ID NO: 14 and the Tth WT nucleotide sequence of SEQ ID NO: 13.

FIG. 8 shows the Taq Exo⁻ amino acid sequence of SEQ ID NO: 16 and the Taq Exo⁻ nucleotide sequence of SEQ ID NO: 15.

FIG. 9 shows the Taq Exo⁻+E742A amino acid sequence of SEQ ID NO: 18 and the Taq Exo⁻+E742A nucleotide sequence of SEQ ID NO: 17

FIG. 10 shows the Taq R651E amino acid sequence of SEQ ID NO: 20 and the Taq R651E nucleotide sequence of SEQ ID NO: 19.

FIG. 11 shows the Tth P653E amino acid sequence of SEQ ID NO: 22 and the Tth P653E nucleotide sequence of SEQ ID NO: 21.

DESCRIPTION OF EMBODIMENTS

Figure 2:
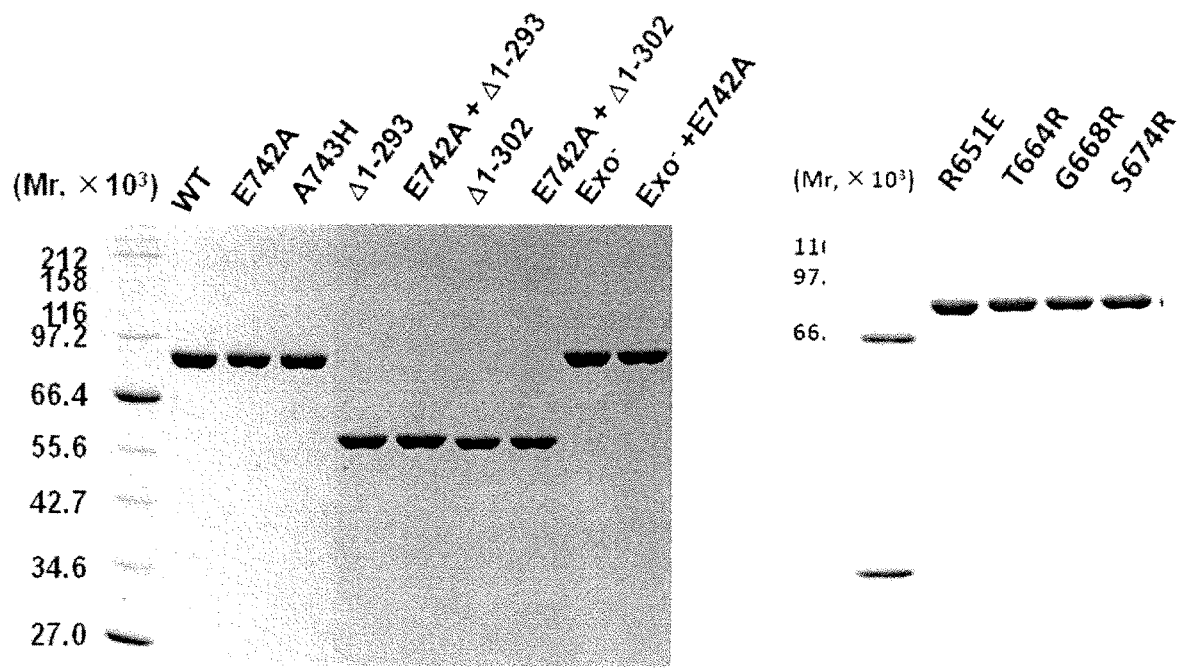
Figure 3:
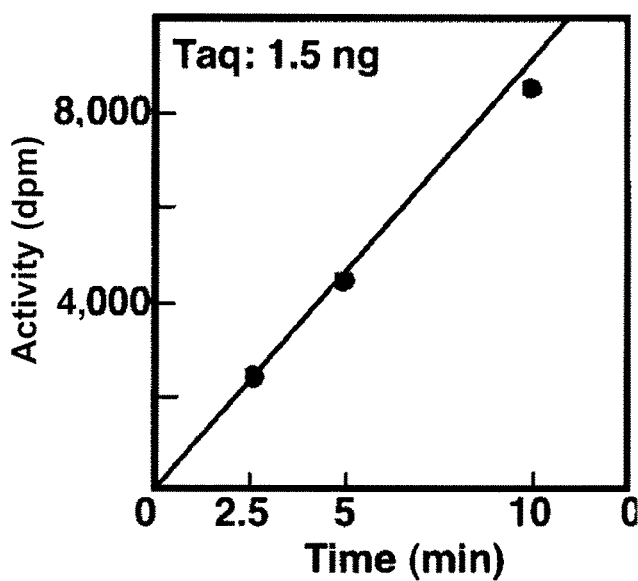
Figure 4:
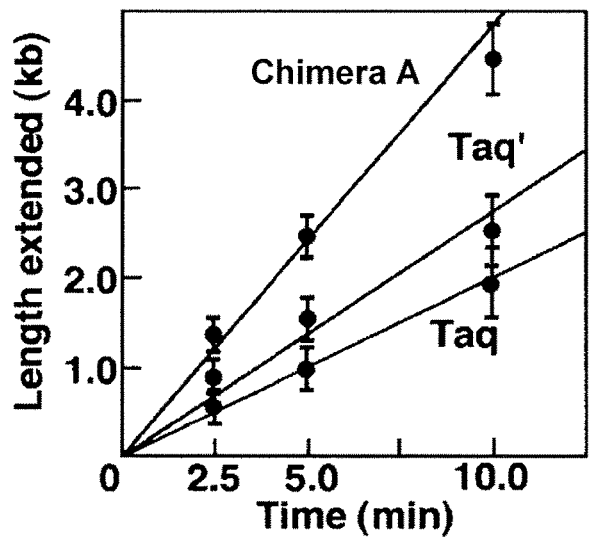
FIG. 4 shows an example of a graph for determining primer extension rate. With the amount of enzyme kept constant, a time course of primer extension reaction is taken and the extension rate can be determined by measuring the length of strand extended per unit time through alkaline agarose electrophoresis in a region where the plots lie on a straight line (refer to Example 2). Under the conditions of this test, Taq showed a rate of 4.67 kb/min/U, Taq' (Taq mutant) showed a rate of 6.67 kb/min/U, and Chimera A (the chimera created by recombining a segment of the Taq gene with a homologous region obtained from the metagenome) showed a rate of 11.20 kb/min/U.

Definitions, Etc.

The "DNA polymerase" as referred to in the present invention, unless otherwise specified, means a protein having the activity of extending a complementary DNA strand to a template nucleic acid (DNA or RNA) using deoxyribonucleoside triphosphate as a substrate. The "Taq polymerase" or "Taq DNA polymerase" as referred to in this invention, unless otherwise specified, means a DNA polymerase derived from *Thermus aquaticus*. The amino acid sequence and the nucleotide sequence are respectively shown in SEQ ID NOs: 12 and 11 in the Sequence Listing, which constitutes a part of the present specification. The "Tth polymerase" or "Tth DNA polymerase" as referred to in this invention means a DNA polymerase derived from *Thermus thermophilus*. The amino acid sequence and the nucleotide sequence are respectively shown in SEQ ID NOs: 14 and 13 in the Sequence Listing, which constitutes a part of the present specification.

DNA Polymerase Activity:

The "activity" as referred to in the present invention in connection with a DNA polymerase includes transcriptional activity and primer extension activity.

The transcriptional activity includes transcriptional activity using DNA as a template, and transcriptional activity using RNA as a template. As well known to those skilled in the art, the transcriptional activity can be determined as the activity of incorporating deoxyribonucleoside triphosphate (dNTP) as a substrate. More specifically, a calf thymus DNA, a salmon sperm DNA, or the like is partially digested with DNase I to provide a nicked or gapped double-strand DNA as a template, and a radioisotope-labeled dNTP is mixed with a substrate dNTP; then, the DNA polymerase of interest is caused to act, so that the amount of nucleotides incorporated into nicks by nick translation or into gaps by primer extension activity can be determined using radioactivity as an indicator. This determination method, which is called nucleotide incorporation assay, is a standard method for determining DNA polymerase activity.

The "transcriptional activity" or "basic DNA polymerase activity" as referred to in the present invention, unless otherwise specified, means the activity of incorporating dNTP when DNA strand is used as a template. When the "transcriptional activity" or "basic DNA polymerase activity" is represented by numerical value in this invention, unless otherwise specified, the amount of enzyme, i.e., DNA polymerase, required to incorporate 10 nmol of nucleotides at 72° C. for 30 minutes is defined as 1 unit (U), and such activity is expressed as a value for specific activity (activity per protein amount) in U/mg or the like. Unless otherwise specified, the conditions for this determination are set as disclosed in the Examples section of the present application.

The "reverse transcriptional activity" as referred to in the present invention, unless otherwise specified, means the activity of incorporating dNTP when RNA strand is used as a template. When the "reverse transcriptional activity" is represented by numerical value in this invention, unless otherwise specified, the amount of enzyme, i.e., DNA polymerase, required to incorporate 10 nmols of nucleotide at 72° C. for 30 minutes is defined as 1 unit (U), and such activity is expressed as a value for specific activity (activity per protein amount) in U/mg or the like. Unless otherwise specified, the conditions for this determination are set as disclosed in the Examples section of the present application.

The "primer extension activity" as referred to in the present invention, unless otherwise specified, means the length of strand extended per unit time when a DNA polymerase of interest is caused to act on a substrate dNTP using DNA or RNA as a template, and the length can be expressed in kb/U/min, bp/pmol/min, or the like. Unless otherwise specified, the conditions for this determination are set as disclosed in the Examples section of the present application.

DNA Polymerases of the Present Invention:

The present invention provides novel DNA polymerases, more specifically mutants of Family A DNA polymerases derived from thermophilic eubacteria, notably particular mutants of *Thermus aquaticus* polymerases (Taq polymerases) or mutants of homologues thereof.

The "thermophilic eubacteria" as referred to herein means eubacteria having an optimum growth temperature of at least 45° C. or at least 60° C. Examples include bacteria of the genus *Thermus*, such as *Thermus aquaticus* and *Thermus thermophilus*, those of the genus *Thermotoga*, such as *Thermotoga maritima*, those of the genus *Aquifex*, such as *Aquifex aeolicus*, and those of the genus *Thermodesulfobacterium*, such as *Thermodesulfobacterium commune*, with preference given to *Thermus aquaticus* and *Thermus thermophilus*.

Thus, examples of the DNA polymerase of the present invention that are preferably provided include not only mutants of *Thermus aquaticus*-derived DNA polymerases (Taq polymerases) or mutants of *Thermus thermophilus*-derived DNA polymerases (Tth polymerases), but also mutants of Family A DNA polymerases derived from other thermophilic eubacteria, in which an amino acid that is shown by sequence comparison to correspond to a mutation site of a Taq polymerase is mutated.

For example, it was found that when the amino acid sequences of a *Thermus aquaticus*-derived DNA polymerase (Taq polymerase) and a *Thermus thermophilus*-derived DNA polymerase (Tth polymerase) are compared and aligned, the amino acid at position 651 in the Taq polymerase and the amino acid at position 653 in the Tth polymerase correspond to each other (FIG. 1).

As a result of investigation about chimeric Taq polymerases, the present inventors found two chimeric enzymes having high primer extension activity and reverse transcriptional activity, and other chimeric enzymes which have almost the same sequences as said two enzymes but show extremely low activities. The inventors also selected from those sequences one residue that is only inconsistent in the low-activity enzymes, and introduced a mutation to this residue, whereby the inventors found a mutant Taq polymerase (Taq R651E) and a mutant Tth polymerase (Tth P653E), which respectively have a reverse transcriptional activity 1.4 and 1.7 times greater than that of the wild-type Tth polymerase.

Thus, in the first aspect, the present invention provides a DNA polymerase comprising an amino acid sequence modified from an amino acid sequence of a Family A DNA polymerase derived from a thermophilic eubacterium, which has a substitution of one corresponding amino acid residue by an amino acid residue having a negatively charged side chain (in respect of the first aspect, refer to [1] and [2] mentioned above). Specifically, this invention provides a DNA polymerase comprising: an amino acid sequence modified from the amino acid sequence of SEQ ID NO: 12, which has a substitution of the arginine residue at position 651 by an amino acid residue having a negatively charged side chain; or an amino acid sequence modified from an amino acid sequence of a Family A DNA polymerase derived from a thermophilic eubacterium, which has a substitution of an amino acid residue corresponding to position 651 in SEQ ID NO: 12 by an amino acid residue having a negatively charged side chain (in respect of the first aspect, refer to [1] and [2] mentioned above). More specifically, this invention provides a DNA polymerase comprising the mutant Taq R651E or a homologue thereof, or the mutant Tth P653E or a homologue thereof (in respect of the first aspect, refer to [3] to [7] mentioned above for the mutant Taq R651E, and [8] to [12] for mutant Tth P653E).

The amino acid sequence of Taq R651E and the nucleotide sequence encoding the same are respectively shown in SEQ ID NOs: 20 and 19 in the Sequence Listing which constitutes a part of the present specification. The amino acid sequence of Tth P653E and the nucleotide sequence encoding the same are respectively shown in SEQ ID NOs: 22 and 21 in the Sequence Listing which constitutes a part of the present specification.

The DNA polymerase according the first aspect of the present invention is characterized by having improved reverse transcriptional activity over the wild-type DNA polymerase. To be specific, the mutant Taq R651E and the homologues thereof have a reverse transcriptional activity of at least $5.00 \times 10^3$ U/mg, preferably at least $10.0 \times 10^3$ U/mg, more preferably at least $15.0 \times 10^3$ U/mg, and still more preferably at least $20.0 \times 10^3$ U/mg. The mutant Tth P653E and the homologues thereof have a reverse transcriptional activity of at least $16.0 \times 10^3$ U/mg, preferably at least $18.0 \times 10^3$ U/mg, and more preferably at least $20.0 \times 10^3$ U/mg.

The present inventors further made extensive studies for the purpose of creating a superior PCR enzyme by modifying a Taq polymerase, and as a result found that the mutant Taq Exo⁻ (E117A, D119A, D142A, D144A), in which four amino acid residues presumably important for the 5'→3' exonuclease activity inherent in a Taq polymerase are converted at the same time, are superior to the wild-type Taq polymerase in terms of primer extension activity using DNA as a template. Thus, in the second aspect, this invention provides the mutant Taq Exo⁻ and homologues thereof, polypeptides encoding the same and homologues thereof (in respect of the second aspect, refer to [13] to [17] mentioned above).

The amino acid sequence of Taq Exo⁻ and the nucleotide sequence encoding the same are respectively shown in SEQ ID NOs: 16 and 15 in the Sequence Listing which constitutes a part of the present specification.

In Taq Exo⁻, all of the glutamic acid residue at position 117, the asparatic acid residue at position 119, the asparatic acid residue at position 142, and the asparatic acid residue at position 144 in the amino acid sequence of SEQ ID NO: 12 are substituted, but the homologues of said mutant, which have an amino acid sequence in which at least one, preferably two, more preferably three, selected from these residues are each independently substituted by an amino acid having a non-polar aliphatic side chain, preferably by an amino acid selected from the group consisting of glycine, alanine, valine, leucine, isoleucine and proline, and more preferably by alanine, are also encompassed by the present invention.

The mutant Taq Exo⁻ and the homologues thereof according to the second aspect of the present invention have a primer extension activity using DNA as a template, at least 4.00 kb/U·min, preferably at least 8.00 kb/U·min, more preferably 9.00 kb/U·min, and still more preferably 14.0 kb/U·min.

Furthermore, the present inventors found that the mutant Taq Exo⁻ to which the mutation of Patent Document 3 mentioned above is further introduced achieves further improvement in extension activity. Thus, in the third aspect, the present invention provides the mutant Taq Exo⁻+E742A and homologues thereof, polypeptides encoding the same and homologues thereof (in respect of the third aspect, refer to [18] to [22] mentioned above).

The amino acid sequence of Taq Exo⁻+E742A and the nucleotide sequence encoding the same are respectively shown in SEQ ID NOs: 18 and 17 in the Sequence Listing, which constitutes a part of the present specification.

In Taq Exo⁻+E742A, all of the glutamic acid residue at position 117, the asparatic acid residue at position 119, the asparatic acid residue at position 142, and the asparatic acid residue at position 144, as well as the glutamic acid residue at position 742, in the amino acid sequence of SEQ ID NO: 12 are substituted, but the homologues of said mutant, which have an amino acid sequence in which at least one, preferably two, more preferably three, still more preferably four, selected from these residues are each independently substituted by an amino acid having a non-polar aliphatic side chain, preferably by an amino acid selected from the group consisting of glycine, alanine, valine, leucine, isoleucine and proline, and more preferably by alanine, are also encompassed by the present invention.

The mutant Taq Exo⁻+E742A and the homologues thereof according to the third aspect of the present invention have a primer extension activity using DNA as a template, at least 4.00 kb/U·min, preferably at least 8.00 kb/U·min, more preferably 9.00 kb/U·min, and still more preferably 14.0 kb/U·min.

Any of the above-mentioned mutants of the present invention encompasses their variants in which a segment having exonuclease activity and consisting of multiple consecutive amino acid residues starting from the N terminal side is deleted. The N-terminal segment that may be deleted can be designed as appropriate by those skilled in the art. In the case of mutant Taq polymerases, the segment typically consists of the residues at positions 1-233, positions 1-293, or positions 1-302, in the amino acid sequence of SEQ ID NO: 12. In the case of mutant Tth polymerases, the segment typically consists of the residues at positions 1-237 in the amino acid sequence of SEQ ID NO: 14, which correspond to positions 1-233 in the Taq sequence. In every case, the mutant DNA polymerase of this invention even encompasses those variants in which a segment of a shorter amino acid residue length than in the above-mentioned deletion variants is deleted as long as the length is within the segment ranges mentioned above.

When the phrase "which has a substitution, deletion, insertion and/or addition of one to nine amino acid residues" is used in the present invention, the number of amino acids to be substituted or otherwise modified is not particularly limited as long as the protein (DNA polymerase) having the modified amino acid sequence has a desired function, and 1-9 or about 1-4 amino acids may be substituted or otherwise modified, or even more amino acids may be substituted or otherwise modified if said substitution or the like is intended to encode the same or similar amino acid sequence. Means for obtaining a protein having such an amino acid sequence are well known to those skilled in the art.

The substitution or the like of an amino acid(s) may be such a substitution or the like that does not cause an electrostatic change, for example, a substitution by an amino acid(s) that is(are) similar in electric charge and/or polarity. Examples of such a substitution include: substitution between amino acids having such an aliphatic side chain that the side chain (also expressed as "R group") is non-polar around physiological pH (7.0) (e.g., glycine, alanine, valine, leucine, isoleucine, and proline); substitution between amino acids having a polar uncharged side chain (e.g., serine, threonine, cysteine, methionine, asparagine, and glutamine); substitution between amino acids having a side chain that is positively charged around physiological pH (e.g., lysine, arginine, and histidine); substitution between amino acids having a negatively charged side chain (e.g., asparatic acid, glutamic acid); substitution between polar amino acids; and substitution between non-polar amino acids.

Figure 5:
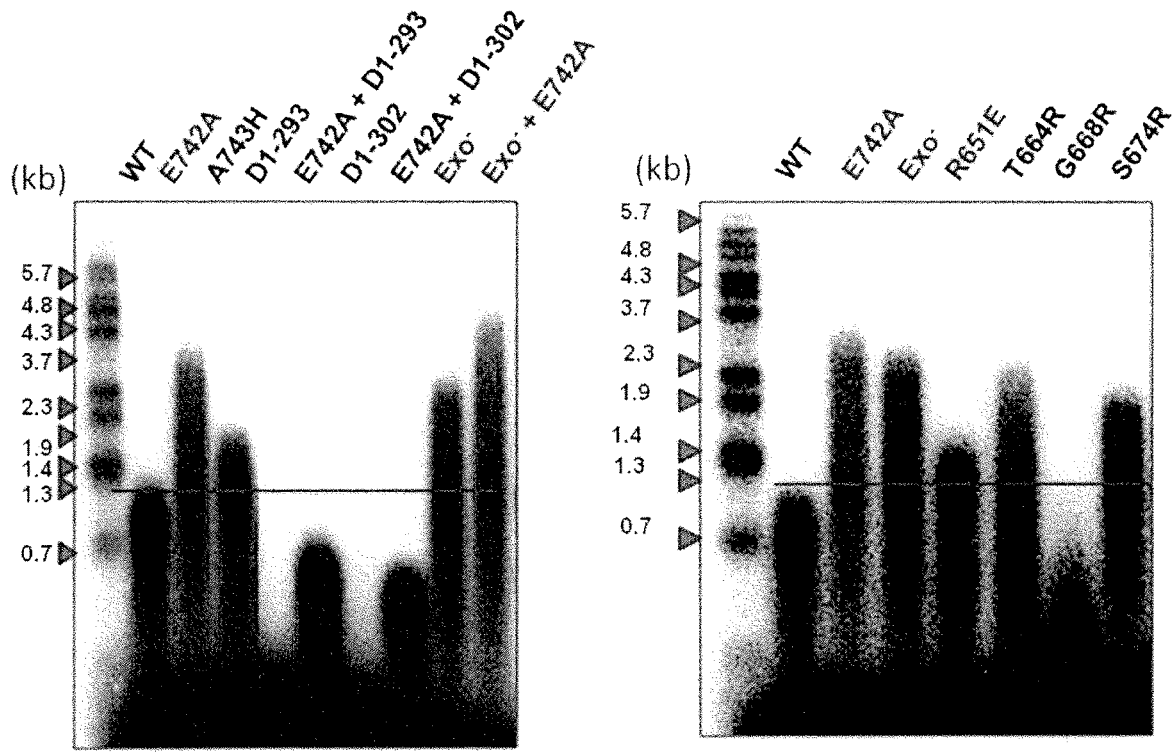
FIG. 5 shows a photograph of the alkaline agarose electrophoresis gels for comparing primer extension rates.

Examples of DNA polymerases preferred in the present invention include not only the mutant DNA polymerases encompassed by the above-mentioned first to third aspects of the invention, but also variants of wild-type Taq polymerases (SEQ ID NO: 12) or wild-type Tth polymerases (SEQ ID NO: 14) which have such an amino acid substitution as characterized above at position 651, 664, 674 or the like. Specific examples include a mutant of a wild-type Taq polymerase (SEQ ID NO: 12), which has a substitution of an arginine residue at position 651 by a glutamic acid residue, a mutant of the same polymerase having a substitution of a threonine residue at position 664 by an arginine residue, and a mutant of the same polymerase having a substitution of a serine residue at position 674 by an arginine residue (refer to FIG. 5).

The "stringent conditions" as referred to in the present invention can be determined as appropriate by those skilled in the art on the basis of the reference data such as polynucleotide length. As to the stringent conditions, those skilled in the art can make reference to the conditions described in Sambrook, et al., *Molecular Cloning: A Laboratory Manual,* 3rd Edition (Cold Spring Harbor Laboratory Press, 2001). The stringent conditions refer to, for example, the hybridization conditions of about 50% formamide, 2×SSC to 6×SSC at about 40-50° C. (or those conditions for other similar hybridization solutions such as Stark's solution in about 50% formamide at about 42° C.). The pre-washing conditions of 5×SSC, 0.5% SDS, 1.0 mM EDTA (pH 8.0), and/or the washing conditions of 0.5×SSC, 0.1% SDS at about 60° C. may also be applied. The stringent conditions more preferably involve not only the hybridization conditions of about 50% formamide, 2×SSC to 6×SSC at about 40-50° C. (or those conditions for other similar hybridization solutions such as Stark's solution in about 50% formamide at about 42° C.), but also the washing conditions of 0.2×SSC, 0.1% SDS at about 68° C.

The high identity as referred to in the present invention in connection with an amino acid sequence, unless otherwise specified, means a sequence identity of at least 80%, preferably at least 90%, more preferably at least 95%, still more preferably at least 96%, and most preferably at least 97%. The high identity as referred to in the present invention in connection with a nucleotide sequence, unless otherwise specified, also means a sequence identity of at least 80%, preferably at least 90%, more preferably at least 95%, still more preferably at least 96%, and most preferably 97%. Search and analysis of polynucleotide or amino acid sequence identity can be made using an algorithm or program well known to those skilled in the art (e.g., BLASTN, BLASTP, BLASTX, ClustalW). When the program is used, parameters can be appropriately set by those skilled in the art, or the default parameters of each program may also be used. Specific procedures for such analyses are also well known to those skilled in the art.

Of both amino acid and nucleotide sequences, an important site for performance of an intended function is described in the present specification. Accordingly, those skilled in the art can design, prepare and use different mutants in which the sequences of other segments than such an important site are modified as appropriate. Such mutants can also fall within the scope of the present invention.

The DNA polymerases of the present invention can be prepared by a method well known to those skilled in the art. In order to construct a recombinant vector, a DNA fragment of an appropriate length, which contains the coding region of a protein of interest, is prepared as a first step. In the nucleotide sequence of the coding region of the protein of interest, nucleotides may be so substituted as to give optimal codons for expression in host cells. Next, the prepared DNA fragment is inserted downstream of a promoter in an appropriate expression vector to construct a recombinant vector. It is necessary that said DNA fragment be incorporated into the vector so as to perform its function. The vector may contain not only promoters but also cis elements (e.g., enhancers), splicing signals, polyadenylation signals, selective markers (e.g., dihydrofolate reductase gene, ampicillin resistance gene, neomycin resistance gene), ribosome binding sequences (SD sequences), and/or the like. A transformant capable of producing a protein of interest can be obtained by introducing a recombinant vector into an appropriate host cell.

The expression vector is not particularly limited as long as it is capable of autonomous replication in a host cell, and examples of the vector that can be used include plasmid vectors, phage vectors, and viral vectors. Examples of the plasmid vectors that can be used include *E. coli*-derived plasmids (e.g., pRSET, pBR322, pBR325, pUC118, pUC119, pUC18, and pUC19), *Bacillus subtilis*-derived plasmids (e.g., pUB110 and pTP5), and yeast-derived plasmids (e.g., YEp13, YEp24, and YCp50). Examples of the phage vectors that can be used include λ phages (e.g., Charon4A, Charon21A, EMBL3, EMBL4, λgt10, λgt11, and λZAP). Examples of the viral vectors that can be used include animal viruses such as retroviruses and vaccinia viruses, and insect viruses such as baculoviruses.

As the host cell, there can be used any of prokaryocytes, yeasts, animal cells, insect cells, plant cells, and other cells, as long as the cell is capable of expressing a DNA encoding a protein of interest. Animal individuals, plant individuals, silkworms, and the like may also be used.

When a bacterium is used as a host cell, examples of the bacterium that can be used as a host cell include bacteria of the genus *Escherichia*, such as *Escherichia coli*, those of the genus *Bacillus*, such as *Bacillus subtilis*, those of the genus *Pseudomonas*, such as *Pseudomonas putida*, and those of the genus *Rhizobium*, such as *Rhizobium meliloti*. Specific examples of the bacterium that can be used as a host cell include *Escherichia coli* such as *Escherichia coli* BL21, *Escherichia coli* XL1-Blue, *Escherichia coli* XL2-Blue, *Escherichia coli* DH1, *Escherichia coli* K12, *Escherichia coli* JM109, and *Escherichia coli* HB101, and *Bacillus subtilis* such as *Bacillus subtilis* MI 114, and *Bacillus subtilis* 207-21. The promoter used in this case is not particularly limited as long as it can be expressed in a bacterium such as *E. coli*, and examples of the promoter that can be use include those derived from *E. coli*, phages and the like, such as trp promoter, lac promoter, $P_L$ promoter, and $P_R$ promoter. Artificially designed and modified promoters such as tac promoter, lacT7 promoter, and let I promoter can also be used. When a yeast is used as a host cell, examples of the yeast that can be used as a host cell include *Saccharomyces cerevisiae, Schizosaccharomyces pombe*, and *Pichia pastoris*. The promoter used in this case is not particularly limited as long as it can be expressed in a yeast, and examples of the promoter that can be used include gal1 promoter, gal10 promoter, heat shock protein promoter, MFα1 promoter, PHO5 promoter, PGK promoter, GAP promoter, ADH promoter, and AOX1 promoter. When an insect cell is used as a host, examples of the insect cell that can be used as a host cell include *Spodoptera frugiperda* ovarian cells, *Trichoplusia ni* ovarian cells, and cultured cells derived from silkworm ovaries. Examples of the *Spodoptera frugiperda* ovarian cells that can be used include Sf9 and Sf21; examples of the *Trichoplusia ni* ovarian cells that can be used include High 5 and BTI-TN-5B1-4 (Invitrogen); and examples of the cultured cells derived from silkworm ovaries that can be used include *Bombyx mori* N4.

The method for introducing a recombinant vector into a host is not particularly limited, as long as the method allows introduction of a DNA into the host, and examples of the method that can be used include a calcium ion method, electroporation, a spheroplast method, and a lithium acetate method. The method for introducing a recombinant vector into an insect cell is not particularly limited, as long as the method allows introduction of a DNA into the insect cell, and examples of the method that can be used include a calcium phosphate method, lipofection, and electroporation.

A transformant having introduced therein a recombinant vector incorporating a DNA encoding a protein of interest is cultured. Culturing of the transformant can be carried out according to a conventional method used for culture of host cells.

The protein of interest can be obtained by collecting it from the culture of the transformant. The "culture" as referred to herein encompasses all of culture supernatants, cultured cells, cultured microorganisms, and disrupted products of cells or microorganisms. In the case where the protein of interest is accumulated in transformant cells, the culture is centrifuged to collect the cells from the culture, and the collected cells are washed and disrupted to extract the protein of interest. In the case where the protein of interest is excreted outside the transformant cells, the culture supernatant is used as it is, or cells or microorganisms are removed from the culture supernatant by centrifugation or the like. The extracted protein can be purified by solvent extraction, salting-out/desalting with ammonium sulfate or the like, precipitation with an organic solvent, diethylaminoethyl (DEAE)-sepharose, ion exchange chromatography, hydrophobic chromatography, gel filtration, affinity chromatography, or the like.

The mutants of the present invention are useful for DNA amplification (particularly, PCR) and can be used as a component of a DNA amplification (particularly, PCR) kit. In addition to the inventive mutant Taq polymerases or fragments thereof, the DNA amplification (particularly, PCR) kit can contain reagents (e.g., four types of dNTPs, $Mg^{2+}$, buffer, additives), a vessel, an apparatus, and the like which are necessary for DNA amplification (particularly, PCR). The inventive DNA amplification method and kit are suitable for a variety of applications, including DNA sequencing, gene diagnosis, individual identification in paternity test and criminal investigation, variety identification, SNP (single nucleotide polymorphism) analysis for constitutional study, and archaeological excavation

EXAMPLES

Example 1: Construction of Mutants

1. Introduction of Mutations:

In order to construct each of amino acid substitution mutants of a Taq polymerase, one or more site-specific mutations were introduced in a primer dependent manner by PCR using one or more sets of primers having sequences designed to ensure that a mutation is applied to a position of interest, with an expression plasmid having a Taq polymerase gene inserted therein being used as a template. The introduction of one or more site-specific mutations into a Taq polymerase was performed using one or more sets of primers shown below. The amino acid substitution sites employed to construct the respective mutants are underlined.

[Formula 1]
Exo⁻
Taq117119A-F
(SEQ ID NO: 1)
CTCGAGGTCCCGGGCTACGCGGCGGCCGACGTCCTGGCCAGCCTG Taq117119A-R
(SEQ ID NO: 2)
CAGGCTGGCCAGGACGTCGGCCGCCGCGTAGCCCGGGACCTCGAG Taq142144A-F
(SEQ ID NO: 3)
GTCCGCATCCTCACCGCCGCCAAAGCCCTTTACCAGCTCCTTTCC Taq142144A R
(SEQ ID NO: 4)
GGAAAGGAGCTGGTAAAGGGCTTTGGCGGCGGTGAGGATGCGGAC

[Formula 2]
Exo⁻ + E742A
Taq117119A-F
(SEQ ID NO: 1)
CTCGAGGTCCCGGGCTACGCGGCGGCCGACGTCCTGGCCAGCCTG Taq117119A-R
(SEQ ID NO: 2)
CAGGCTGGCCAGGACGTCGGCCGCCGCGTAGCCCGGGACCTCGAG Taq142144A-F
(SEQ ID NO: 3)
GTCCGCATCCTCACCGCCGCCAAAGCCCTTTACCAGCTCCTTTCC Taq142144A-R
(SEQ ID NO: 4)
GGAAAGGAGCTGGTAAAGGGCTTTGGCGGCGGTGAGGATGCGGAC

E742A-F
(SEQ ID NO: 5)
GTGAAGAGCGTGCGGGCGGCGGCCGAGCGCATG

E742A-R
(SEQ ID NO: 6)
CATGCGCTCGGCCGCCGCCCGCACGCTCTTCAC

[Formula 3]
TaqR651E
R651E-F
(SEQ ID NO: 7)
ATGTTCGGCGTCCCCGAGGAGGCCGTGGAC

R651E-R
(SEQ ID NO: 8)
GTCCACGGCCTCCTCGGGGACGCCGAACAT

[Formula 4]
TthP653E
P653E-F
(SEQ ID NO: 9)
ATGTTCGCCGTCCCCGAGGAGGCCGTGGAC

P653E-R
(SEQ ID NO: 10)
GTCCACGGCCTCCTCGGGGACGCCGAACAT

Fifty microliters of a PCR reaction mixture (20 ng of pTV-Taq plasmid DNA, 0.5 µM each primer set, 0.2 mM dNTP, and 1 U of Pyrobest DNA polymerase (Takara Bio)) was subjected to initial denaturation in a Pyrobest buffer at 98° C. for 10 seconds, which was followed by PCR under the conditions of 16 cycles (98° C. for 10 seconds, 55° C. for 30 seconds, and 72° C. for 8 minutes). 5 U of the restriction enzyme DpnI was added to the resulting PCR product, and the mixture was incubated at 37° C. for 2 hours. Then, the reaction mixture was introduced into the *E. coli* JM109 strain, and the resulting strain was cultured. By using the procedure described in the next section, a plasmid was extracted from the resulting transformant clone, and then a check was made to see that the mutation(s) was(were) introduced in the position(s) of interest.

2. Preparation of Plasmids and Confirmation of Nucleotide Sequences:

With a drug resistance gene in the plasmid being used as a marker, selection was made of an *E. coli* transformant that was seeded onto an LB plate medium containing 50 µg/mL of ampicillin and cultured at 37° C. for 15 hours. The colony that has grown was inoculated into 4 mL of an LB liquid medium containing 50 µg/mL of ampicillin and cultured at 37° C. for 15 hours. A plasmid was extracted from the harvested microorganisms using a QIAprep Spin Miniprep Kit (QIAGEN) according to the kit's protocol. With the DNA of the resulting plasmid being used as a template, dideoxy reaction was performed using a DTCS Quick Start Master Mix (Beckman Coulter), so that the nucleotide sequence was confirmed using a multi-capillary DNA analysis system CEQ2000XL (BECKMAN COULTER).

The novel DNA polymerases constructed in the present study are listed in the following table.

TABLE 1

| DNA Polymerase | number of amino acids | Theoretical pI | Mw. | characteristics |
|---|---|---|---|---|
| Taq WT (SEQ ID NO: 12) | 832 | 6.04 | 93910.1 | Taq Pol wild type |
| Taq8 E742A | 832 | 6.06 | 93852.1 | E742A |
| Taq8 A743H | 832 | 6.10 | 93976.2 | A743H |
| 294L WT | 540 | 5.88 | 60914.1 | Deletion (293 aa of N-ter) |
| 294L E742A | 540 | 5.97 | 60856.1 | Deletion (293 aa of N-ter), E742A |
| 303E WT | 531 | 6.07 | 59896.9 | Deletion (302 aa of N-ter) |
| 303E E742A | 531 | 6.18 | 59838.9 | Deletion (302 aa of N-ter), E742A |
| Exo·WT (SEQ ID NO: 16) | 832 | 6.31 | 93720.0 | E117A, D119A, D142A, D144A |
| Exo·E742A (SEQ ID NO: 18) | 832 | 6.31 | 93662.0 | E117A, D119A, D142A, D144A, E742A |
| Taq R651E (SEQ ID NO: 20) | 832 | 5.92 | 94785.2 | R651E |
| Taq T664R | 832 | 6.10 | 93965.2 | T664R |
| Taq G668R | 832 | 6.10 | 94009.2 | G668R |
| Taq S674R | 832 | 6.10 | 93979.2 | S674R |
| Tth WT (SEQ ID NO: 14) | 834 | 6.30 | 94049.4 | Tth Pol Wild type |
| Tth P653E (SEQ ID NO: 22) | 834 | 6.23 | 94081.4 | Tth Pol P653E |

3. Expression and Purification of DNA Polymerases:

Production of each of wild-type and mutant Taq polymerases was performed under the following conditions: the JM109 strain was transformed by a standard method using a plasmid that incorporated the gene of each polymerase into the pTV-118N vector, and the resulting transformant was cultured at 37° C. for 24 hours in 500 mL of an LB liquid medium containing 50 μg/mL of ampicillin. Production of each of wild-type and mutant Tth polymerases was performed under the following conditions: the BL21 (DE3) CodonPlus-RIPL strain (Stratagene) was transformed by a standard method using pET-3C as an expression vector, and the resulting transformant was cultured at 37° C. for 24 hours in 500 mL of an LB liquid medium containing 50 μg/mL of ampicillin and 33 μg/mL of chloramphenicol. Thereafter, the culture was centrifuged at 6,000 rpm for 15 minutes to harvest microorganisms, and the harvested microorganisms were suspended in 25 mL of Buffer A (50 mM Tris-HCl (pH 8.0), 0.1 mM EDTA, 0.5 mM DTT, 10% glycerol) supplemented with 1 mM PMSF, and were subjected to ultrasonication and centrifuged at 14,500 rpm for 15 minutes to obtain a crude cell extract. The crude extract was left to stand at 80° C. for 20-30 minutes to denature a non-thermostable protein, and was centrifuged at 14,500 rpm for 15 minutes to obtain a thermostable fraction in the supernatant. Polyethyleneimine was added to the fraction on ice so as to give a concentration of 0.15%, and the precipitate (nucleic acid) was removed by centrifugation at 14,500 rpm for 15 minutes. Next, ammonium sulfate was added to the supernatant on ice so as to give 80% saturation, and the suspension was stirred for at least 1 hour to effect salting-out. The suspension was centrifuged at 14,500 rpm for 15 minutes to effect protein precipitation, and the precipitate was suspended in Buffer A supplemented with 0.8 M ammonium sulfate; thereafter, the suspension was subjected to chromatography by passing it through a Hi Trap Phenyl column (5 mL) using an ÄKTA Explorer (GE Healthcare). After passage of the sample, a gradient from 1 M to 0 M ammonium sulfate was created and ultrapure water was passed through the column to thereby elute an enzyme of interest. The fraction was recovered and passed through a Hi Trap Heparin column (1 mL). Elution was performed with a gradient from 0 M to 800 mM sodium chloride as dissolved in Buffer A. The enzymes of interest thus obtained were each analyzed by SDS-PAGE to confirm their purity.

Example 2: Evaluation of Mutants

1. Transcriptional Activity:

In order to determine the basic DNA polymerase activity of each of the purified enzymes, a world-wide standard method was used. More specifically, the intensity of the activity of incorporating deoxyribonucleotides on a DNA template strand was determined, and the activity per unit protein amount was calculated in units. To perform a nucleotide incorporation reaction, a reaction mixture was prepared by adding 0.2 mg/mL of activated DNA (obtained by treating a calf thymus DNA with DNase I to partially nick or gap a double-strand DNA), 0.2 mM dNTP, 440 nM [$^3$H]-dTTP, 50 mM Tris-HCl (pH 8.0), 1.5 mM MgCl$_2$, 50 mM KCl, 0.1% TritonX-100, 100 μg/mL of BSA, and 1 nM DNA polymerase, and the mixture was reacted at 72° C.; then, 10 μL of the mixture was spotted onto DE81 paper. After air-dried for 10 minutes, the paper was washed with an aqueous 5% disodium hydrogenphosphate solution to remove unreacted nucleotides. The washing was repeated three times each for 10 minutes. After the DE81 paper was dried, radiation was measured by a liquid scintillation counter, whereby the amount of [$^3$H]-dTMP incorporated in the activated DNA due to the DNA polymerase activity was calculated to determine enzyme activity (in unit). One unit is defined as the amount of enzyme, i.e., DNA polymerase, required to incorporate 10 nmol of nucleotides at 72° C. for 30 minutes. The specific activity was calculated for each enzyme.

2. Extension Activity (Extension Rate):

Primer extension activity per unit was determined based on each of the calculated specific activity values. The primer extension reaction was performed using a substrate (primed DNA) obtained by annealing a $^{32}$P-radiolabeled oligonucleotide to an M13 phage single-strand DNA (7 kb). After 10 μL of a reaction mixture (5 nM M13 primed DNA, 0.2 mM dNTP, 50 mM Tris-HCl (pH 8.0), 1.5 mM MgCl$_2$, 50 mM KCl, 0.1% TritonX-100, and 100 μg/mL BSA) was reacted at 72° C. for 5 minutes, the reaction was terminated by adding 2.5 μL of 6× loading buffer (300 nM NaOH, 6 mM EDTA, 18% Ficol 400, 0.15% BCG, and 0.25% XC). The reaction product was separated by agarose gel electrophoresis (agarose gel was prepared at a concentration of 1% in 50 mM NaOH and 1 mM EDTA) under alkaline conditions, and after the electrophoresis, the product was detected by autoradiography (using an image analyzer (FLA-5000, Fujifilm)).

The strand length of the reaction product was determined from the obtained image by comparing it with a size marker, whereby the strand length of the synthetic product obtained per unit time (1 min) was calculated. As a result, it was shown that whereas the wild-type Taq polymerase had an extension rate of 3.89 kb/min, Taq E742A (refer to Patent Document 3: JP 4193997 given above) had an extension rate of 10.7 kb/min, the mutant Exo⁻ whose 5'-3' exonuclease activity residues were substituted in a site-specific manner had an extension rate of 9.17 kb/min, and Exo⁻+E742A produced by crossing Taq E742A with Exo⁻ had a rate of 15.4 kb/min.

3. Reverse Transcriptional Activity:

The intensity of the activity of incorporating deoxyribonucleotides on a RNA template strand was determined for each of the purified DNA polymerases. In order to perform the reaction, the DNA polymerase was added to a solution containing 20 ng/μL of poly(rA)•p(dT), 10 μM dTTP, 440 nM [$^3$H]-dTTP, 50 mM Tris-HCl (pH 8.0), 1 mM MnCl$_2$, 50 mM KCl, 0.1% TritonX-100, and 100 μg/mL of BSA, and the mixture was reacted at 60° C. for 10 minutes; then, 10 μL of the mixture was spotted onto DE81 paper. After air-dried, the paper was washed with an aqueous 5% disodium hydrogenphosphate solution to remove unreacted nucleotides. The washing was repeated three times each for 10 minutes. After the DE81 paper was dried, radiation was measured by a liquid scintillation counter, whereby the amount of [$^3$H]-dTMP incorporated in the poly(rA)•p(dT) due to the DNA polymerase activity was calculated to determine enzyme activity (in unit). One unit is defined as the amount of enzyme, i.e., DNA polymerase, required to incorporate 10 nmol of nucleotides at 72° C. for 30 minutes. The specific activity was calculated for each enzyme.

First, a Tth polymerase with strong reverse transcriptional activity was prepared for use as a positive control. It was revealed that the Tth polymerase purified by the present inventors showed a reverse transcriptional activity of $1.54 \times 10^4$ U/mg, while the wild-type Taq DNA polymerase which was also purified by the inventors showed a reverse transcriptional activity of $0.42 \times 10^4$ U/mg (corresponding to a relative activity of 27% with respect to the Tth polymerase in the present study).

The reverse transcriptional activity of each of the mutants constructed according to the present invention was determined using the same conditions on the basis of its nucleotide incorporation activity. As a result, it was shown that Taq R651E and Tth P653E showed a reverse transcriptional activity of $2.09 \times 10^4$ U/mg and $2.54 \times 10^4$ U/mg, respectively. These results mean that Taq R651E and Tth P653E showed activities 1.36 and 1.65 times, respectively, greater than the wild-type Tth polymerase, whose reverse transcriptional activity is taken as 1.

The properties of the mutant Taq polymerases are summarized in the following table.

TABLE 2

| DNA Polymerase | Purified Protein from 500 mL culture (mg) | DNA-DNA Specific Activity (×10³ U/mg) | Relative activity (%) | RNA-DNA Specific Activity (×10³ U/mg) | Relative activity (%) | Extension rate DNA (kb/U · min) | Extension rate RNA (bp/pmol · min) |
|---|---|---|---|---|---|---|---|
| Taq WT (SEQ ID NO: 12) | 1.65 | 5.11 | 100 | 4.24 | 27.5 | 3.89 | 14.0 |
| Taq E742A | 0.67 | 5.00 | 97.7 | | | 10.7 | |
| Taq A743H | 0.89 | 3.94 | 77.1 | | | 5.80 | |
| 294L WT | 0.48 | 6.67 | 131 | | | 0.11 | |
| 294L E742A | 0.56 | 12.7 | 249 | | | 0.29 | |
| 303E WT | 0.71 | 6.50 | 127 | | | 0.11 | |
| 303E E742A | 0.63 | 13.5 | 264 | | | 0.26 | |
| Exo·WT (SEQ ID NO: 16) | 0.54 | 3.79 | 74.2 | | | 9.17 | |
| Exo·E742A (SEQ ID NO: 18) | 0.27 | 3.90 | 76.3 | | | 15.4 | |
| Taq R651E (SEQ ID NO: 20) | 1.12 | 3.44 | 67.3 | 20.9 | 136 | 4.36 | 45.4 |
| Taq T664R | 0.65 | 2.03 | 39.8 | | | 7.74 | |
| Taq G668R | 0.21 | 2.98 | 58.2 | | | 2.03 | |
| Taq S674R | 0.31 | 4.56 | 89.3 | | | 6.00 | |
| Tth WT (SEQ ID NO: 14) | 0.68 | 3.66 | 71.5 | 15.4 | 100 | 14.6 | 117 |
| Tth P653E (SEQ ID NO: 22) | 0.66 | 3.37 | 66.0 | 25.4 | 165 | 13.3 | 181 |

SEQUENCE LISTING FREE TEXT

SEQ ID NO: 1 PCR primer Taq117119A-F
SEQ ID NO: 2 PCR primer Taq117119A-R
SEQ ID NO: 3 PCR primer Taq142144A-F
SEQ ID NO: 4 PCR primer Taq142144A-R
SEQ ID NO: 5 PCR primer E742A-F
SEQ ID NO: 6 PCR primer E742A-R
SEQ ID NO: 7 PCR primer R651E-F
SEQ ID NO: 8 PCR primer R651E-R
SEQ ID NO: 9 PCR primer P653E-F
SEQ ID NO: 10 PCR primer P653E-R
SEQ ID NO: 11 Taq WT nucleotide sequence
SEQ ID NO: 12 Taq WT amino acid sequence
SEQ ID NO: 13 Tth WT nucleotide sequence
SEQ ID NO: 14 Tth WT amino acid sequence
SEQ ID NO: 15 Taq Exo⁻ nucleotide sequence
SEQ ID NO: 16 Taq Exo⁻ amino acid sequence
SEQ ID NO: 17 Taq Exo⁻+E742A nucleotide sequence
SEQ ID NO: 18 Taq Exo⁻+E742A amino acid sequence
SEQ ID NO: 19 Taq R651E nucleotide sequence
SEQ ID NO: 20 Taq R651E amino acid sequence
SEQ ID NO: 21 Tth P653E nucleotide sequence
SEQ ID NO: 22 Tth P653E amino acid sequence

The invention claimed is:

1. A DNA polymerase which is any one of (a) to (c) below:
   (a) a DNA polymerase comprising the amino acid sequence of SEQ ID NO:12 with a substitution of the arginine residue at position 651 with a glutamic acid residue;
   (b) a DNA polymerase comprising the amino acid sequence of SEQ ID NO:12, which has a substitution, deletion, insertion and/or addition of one to nine amino acid residues in the amino acid sequence in addition to a substitution of the arginine residue at position 651 with a glutamic acid residue in the amino acid sequence, wherein the DNA polymerase has reverse transcription activity; and
   (c) a DNA polymerase having at least 95% sequence identity to the amino acid sequence of SEQ ID NO: 12, wherein the DNA polymerase comprises a substitution of the arginine residue at position 651 with a glutamic acid residue, and wherein the DNA polymerase has reverse transcription activity.

2. The DNA polymerase as recited in claim 1, which is (a).

3. The DNA polymerase as recited in claim 2, wherein the DNA polymerase consists of the amino acid sequence of SEQ ID NO:20.

4. The DNA polymerase as recited in claim 1, wherein the DNA polymerase of (b) or (c) has reverse transcription activity of at least $16.0 \times 10^3$ U/mg.

5. The DNA polymerase as recited in claim 1, which is (c), wherein the DNA polymerase has at least 97% sequence identity to the amino acid sequence of SEQ ID NO: 12.

* * * * *